(12) United States Patent
Herman et al.

(10) Patent No.: US 11,344,310 B2
(45) Date of Patent: May 31, 2022

(54) PERCUTANEOUS TISSUE ANCHOR TECHNIQUES

(71) Applicant: Valtech Cardio, Ltd., Or Yehuda (IL)

(72) Inventors: Yaron Herman, Givat Ada (IL); Yuval Zipory, Modi'in (IL); Slava Starobinsky, Netanya (IL); Tal Reich, Moledet (IL); Ehud Iflah, Tel Aviv-Jaffa (IL); Alexei Koifman, Melbourne (AU)

(73) Assignee: Valtech Cardio Ltd., Caesarea (IL)

(*) Notice: Subject to any disclaimer, the term of this patent is extended or adjusted under 35 U.S.C. 154(b) by 433 days.

(21) Appl. No.: 16/427,061

(22) Filed: May 30, 2019

(65) Prior Publication Data

US 2019/0321049 A1 Oct. 24, 2019

Related U.S. Application Data

(63) Continuation of application No. 14/437,062, filed as application No. PCT/IL2013/050861 on Oct. 23, 2013, now Pat. No. 10,376,266.
(Continued)

(51) Int. Cl.
*A61B 17/12* (2006.01)
*A61B 17/04* (2006.01)
(Continued)

(52) U.S. Cl.
CPC .... *A61B 17/12009* (2013.01); *A61B 17/0401* (2013.01); *A61B 2017/00477* (2013.01);
(Continued)

(58) Field of Classification Search
None
See application file for complete search history.

(56) References Cited

U.S. PATENT DOCUMENTS 3,604,488 A 9/1971 Wishart et al.
3,656,185 A 4/1972 Carpentier
(Continued)

FOREIGN PATENT DOCUMENTS

EP 1034753 A1 9/2000
EP 3531975 A1 9/2019
(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Thomas McEvoy
(74) *Attorney, Agent, or Firm* — Thomas C. Richardson

(57) ABSTRACT

An example anchor-manipulation tool includes (i) at a distal portion of the tool, an anchor-engaging element and an actuator, (ii) at an extracorporeal proximal portion of the tool, a controller, and (iii) a flexible longitudinal member extending between the proximal portion and the distal portion. The distal portion of the tool can be transluminally advanced to an anchor that is intracorporeally implanted in a subject. Subsequently, the anchor-engaging element can be engaged with an eyelet defined by a head of the anchor. Subsequently, the controller can be used to transition the tool into an articulatably-coupled state in which: (i) the eyelet at least in part inhibits movement of the anchor-engaging element away from the anchor, and (ii) the distal portion of the anchor-manipulation tool is deflectable with respect to the anchor. Subsequently, the anchor can be de-anchored by using the anchor-manipulation tool to apply a de-anchoring force to the eyelet.

24 Claims, 24 Drawing Sheets

Related U.S. Application Data

(60) Provisional application No. 61/820,979, filed on May 8, 2013, provisional application No. 61/784,042, filed on Mar. 14, 2013, provisional application No. 61/745,848, filed on Dec. 26, 2012, provisional application No. 61/717,303, filed on Oct. 23, 2012.

(51) Int. Cl.
*A61F 2/24* (2006.01)
*A61B 17/00* (2006.01)
*A61B 17/29* (2006.01)

(52) U.S. Cl.
CPC .............. *A61B 2017/00681* (2013.01); *A61B 2017/0409* (2013.01); *A61B 2017/0411* (2013.01); *A61B 2017/0441* (2013.01); *A61B 2017/0464* (2013.01); *A61B 2017/0496* (2013.01); *A61B 2017/2937* (2013.01); *A61F 2/2445* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taher |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,306,296 A | 4/1994 | Wright et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,501,683 A * | 3/1996 | Trott .............. A61B 17/0401 606/139 |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,674,279 A | 10/1997 | Wright et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Alien et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |

(56) References Cited

U.S. PATENT DOCUMENTS

| | | |
|---|---|---|
| 6,682,558 B2 | 1/2004 | Tu et al. |
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Aiferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Boiling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |

(56) References Cited

U.S. PATENT DOCUMENTS

| | | |
|---|---|---|
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webier et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,545,553 B2 | 10/2013 | Zipory et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,724,084 B2 | 8/2017 | Groothuis et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |

(56) References Cited

U.S. PATENT DOCUMENTS

| | | |
|---|---|---|
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webier et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Akiog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Saiahieh et al. |
| 2005/0137688 A1 | 6/2005 | Saiahieh et al. |
| 2005/0137695 A1 | 6/2005 | Saiahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0187613 A1 | 8/2005 | Bolduc et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0197858 A1 | 8/2007 | Goldfarb et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |

(56) References Cited

U.S. PATENT DOCUMENTS

| | | |
|---|---|---|
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1* | 9/2008 | Godin ............... A61B 17/0644 600/106 |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0222083 A1 | 9/2009 | Nguyen et al. |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashiri et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280604 A1 | 11/2010 | Zipory et al. |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser |
| 2012/0226349 A1 | 9/2012 | Tuval et al. |
| 2012/0239142 A1 | 9/2012 | Liu et al. |
| 2012/0245604 A1 | 9/2012 | Tegzes |
| 2012/0271198 A1 | 10/2012 | Whittaker et al. |
| 2012/0283757 A1 | 11/2012 | Miller et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |

(56) References Cited

U.S. PATENT DOCUMENTS

| | | |
|---|---|---|
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351906 A1 | 12/2015 | Hammer et al. |
| 2015/0351910 A1 | 12/2015 | Gilmore et al. |
| 2016/0008132 A1 | 1/2016 | Cabiri et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0224489 A1 | 8/2017 | Starksen et al. |
| 2017/0245993 A1 | 8/2017 | Gross et al. |
| 2017/0325959 A1 | 11/2017 | Sheps et al. |
| 2018/0008409 A1 | 1/2018 | Kutzik et al. |
| 2018/0049875 A1 | 2/2018 | Iflah et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |

FOREIGN PATENT DOCUMENTS

| | | |
|---|---|---|
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2010085649 A1 | 7/2010 |
| WO | 2011051942 A1 | 5/2011 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |

OTHER PUBLICATIONS

Ahmadi, A., G. Spiliner, and Th Johannessen. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band," The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Procees, (2000).

Alfieri et al."Novel Suture Device for Beating-Heart Mitral Leaflet Approximation", Ann Thorac Surg. 2002, 74:1488-1493.

(56) References Cited

OTHER PUBLICATIONS

Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral regurgitation, The Journal of Thoracic Cardiovascular surgery vol. 133 No. 1, Jan. 2007.
Langer et al. RING+STRING, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
Odell JA et al., "Early Results o4yf a Simplified Method of Mitral Valve Annuloplasty," Circulation 92:150-154 (1995).
O'Reilly S et al., "Heart valve surgery pushes the envelope," Medtech Insight 8(3): 73, 99-108 (2006).
Park, Sang C. et al. "A percutaneously adjustable device for banding of the pulmonary trunk," International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swensen, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

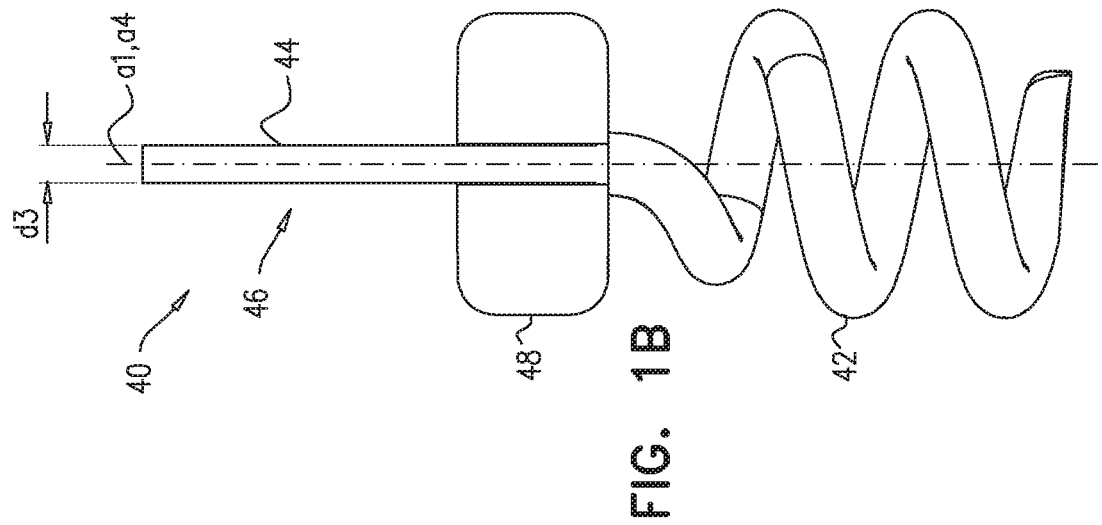
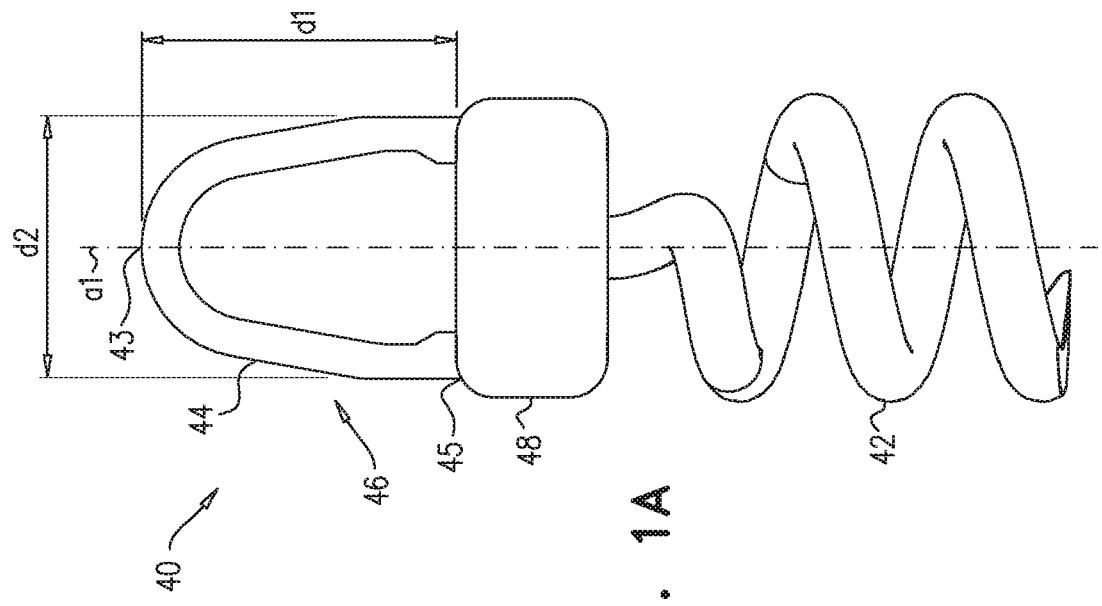

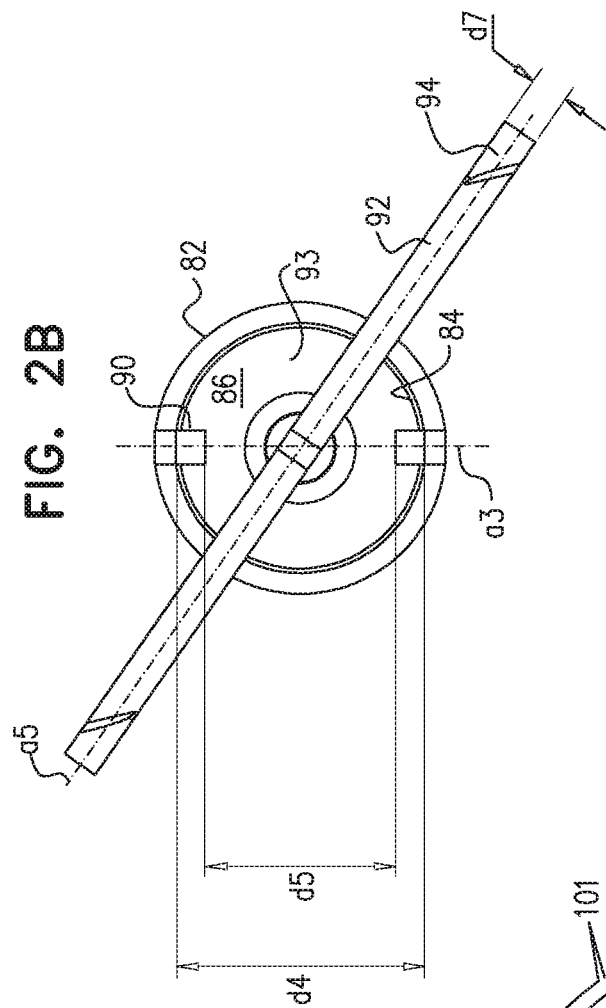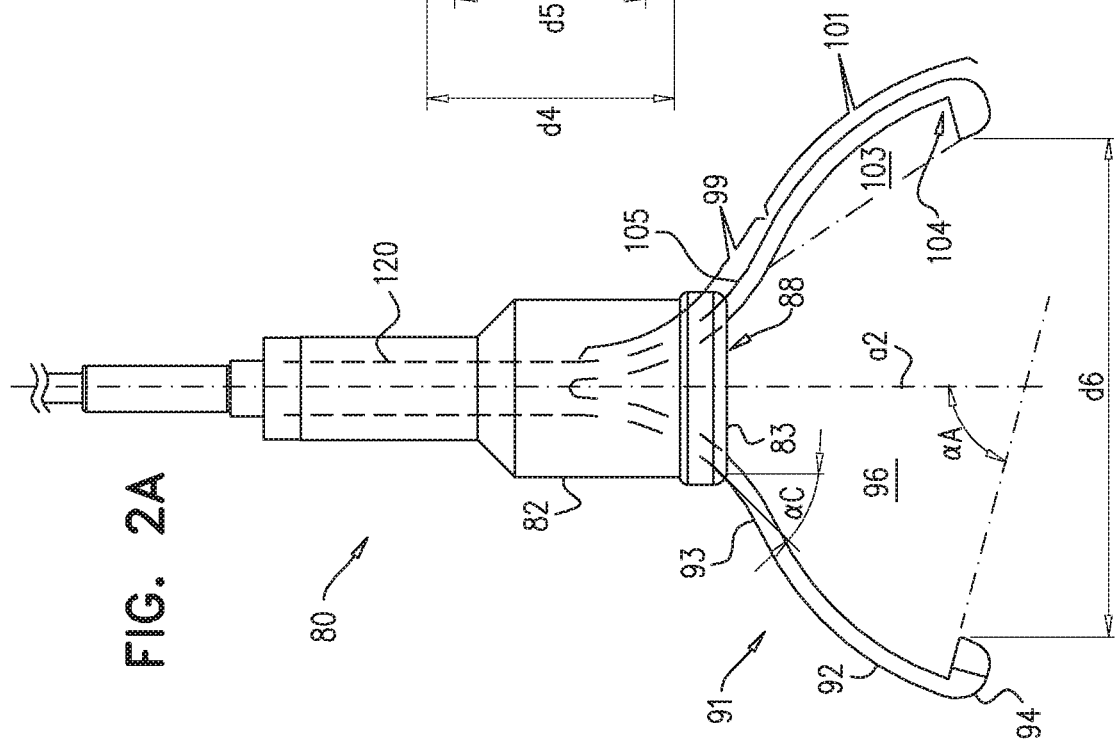

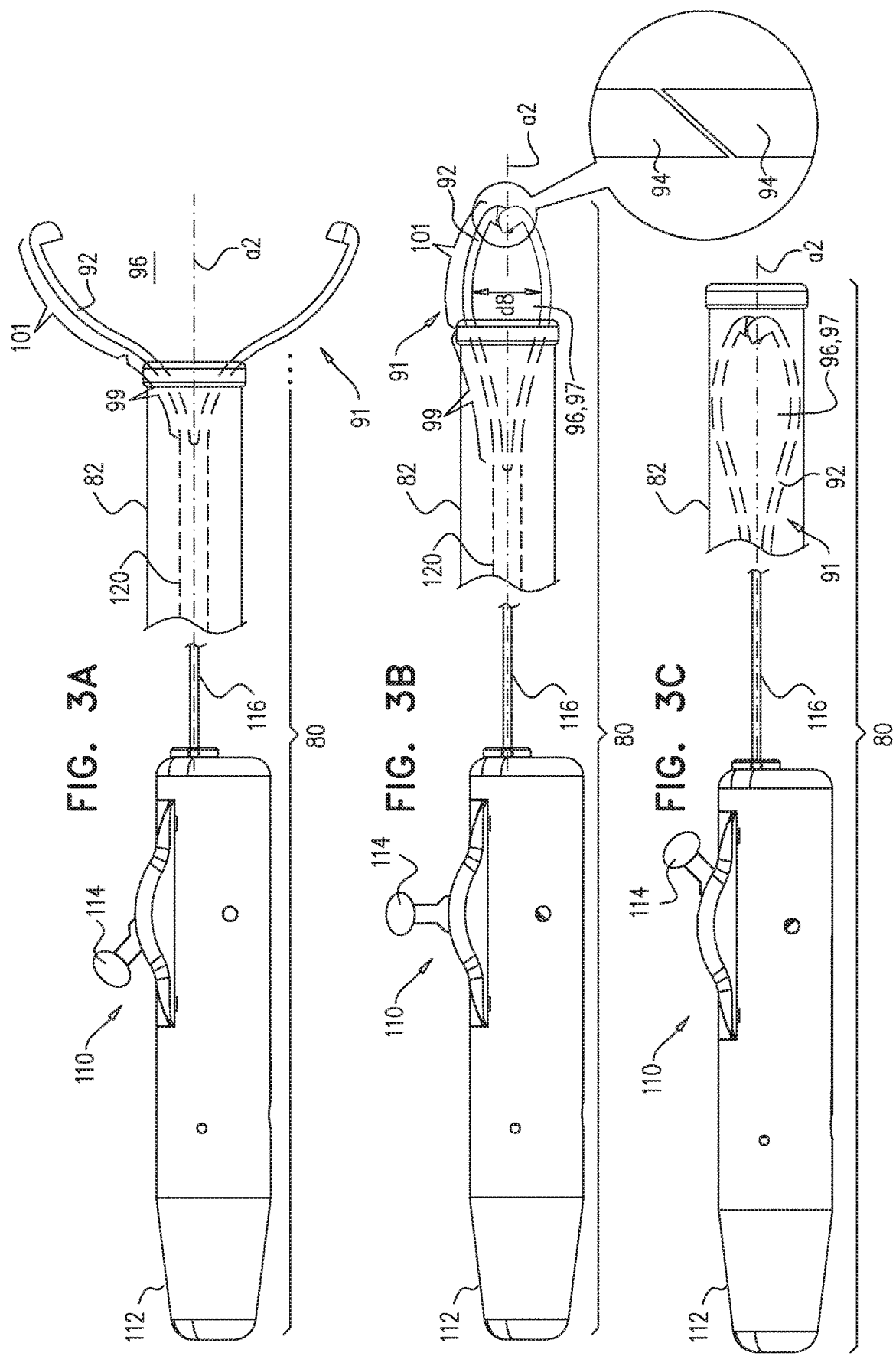

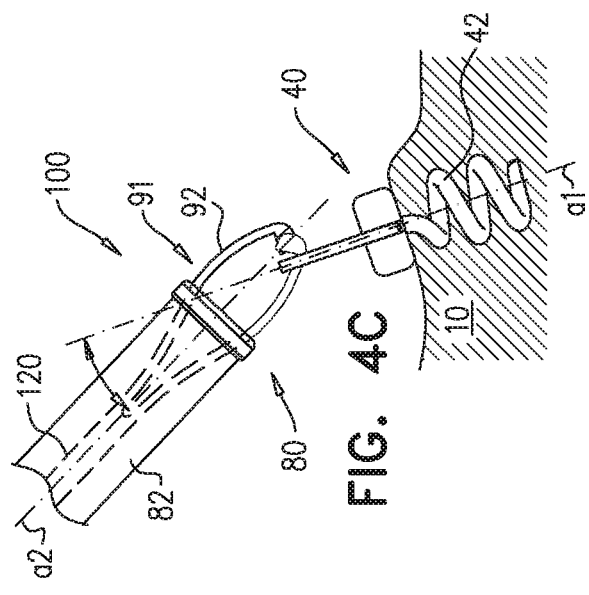
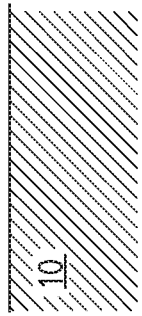
FIG. 4A
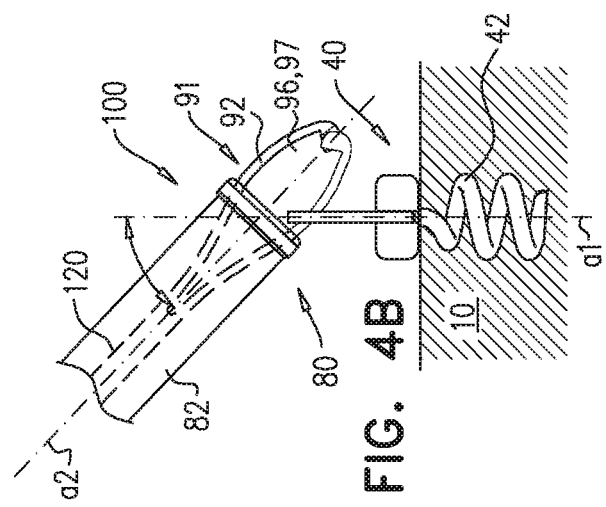
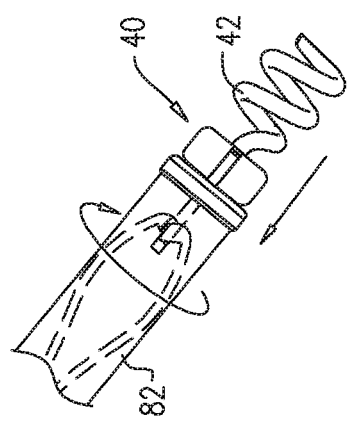
FIG. 4B
FIG. 4C
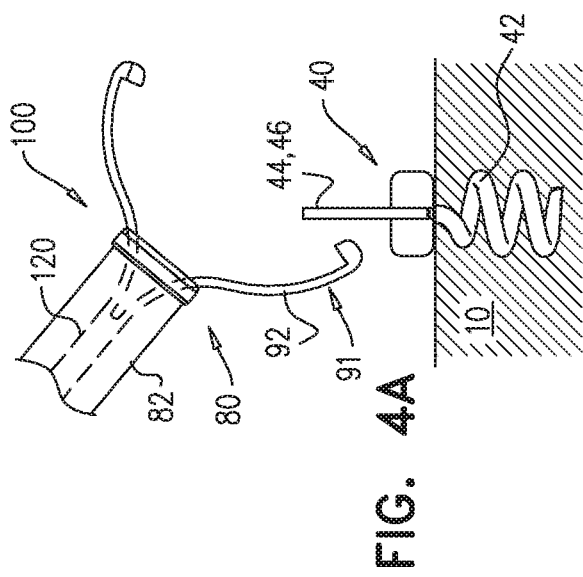
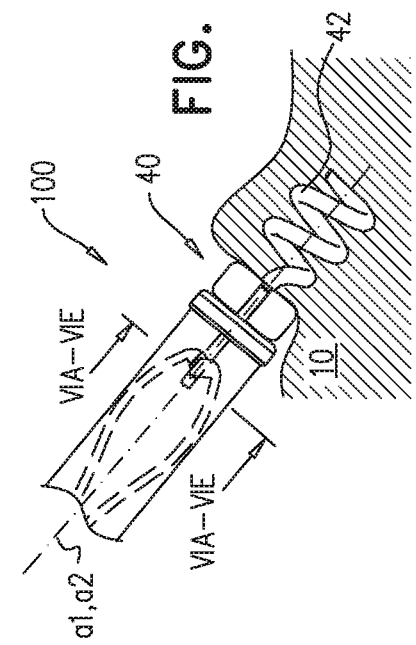
FIG. 4D
FIG. 4E

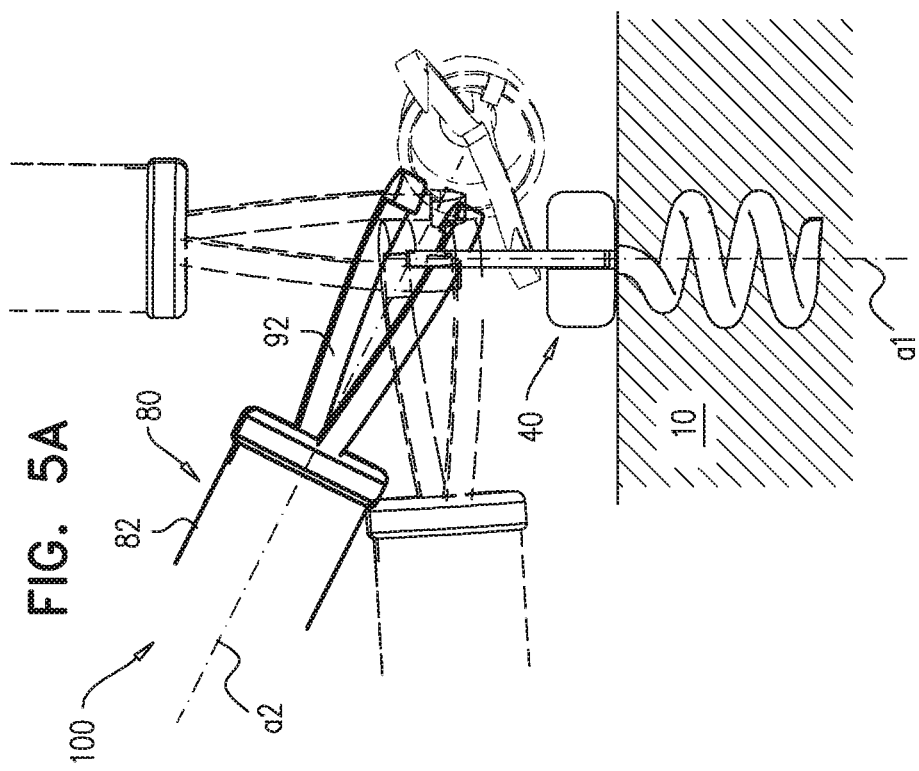
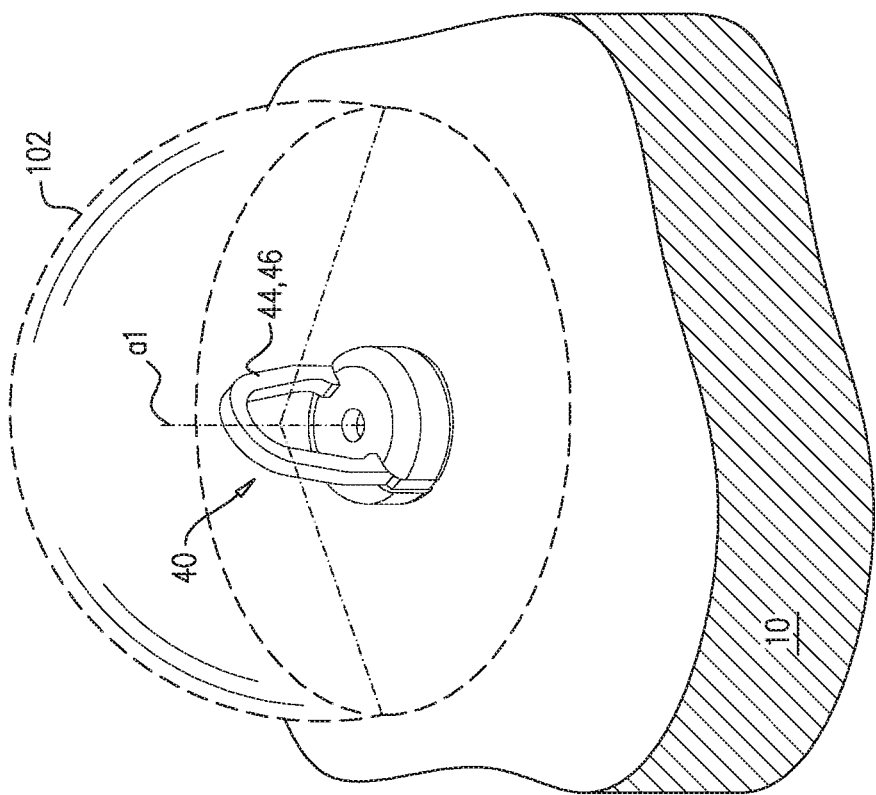

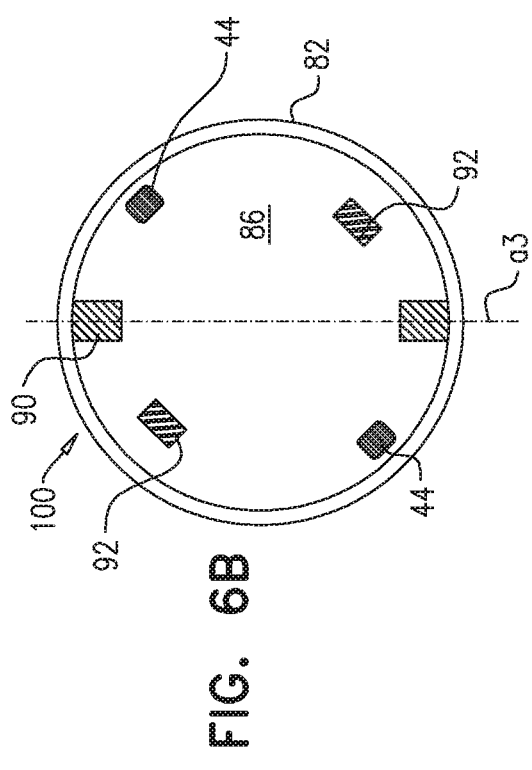
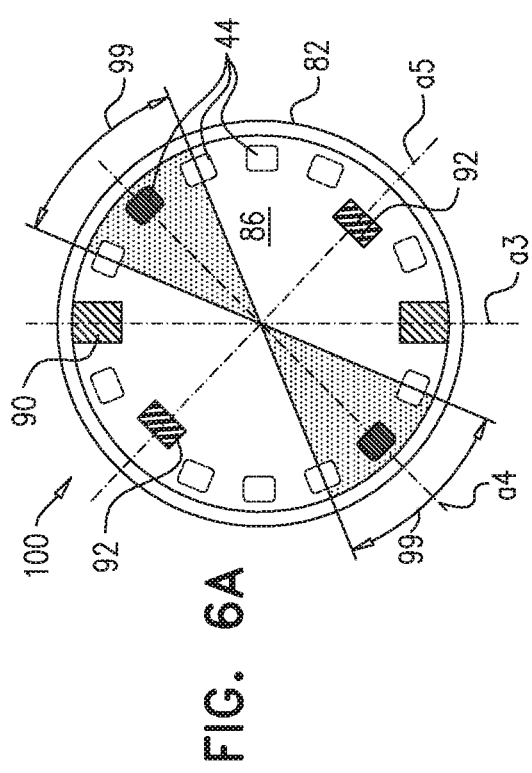
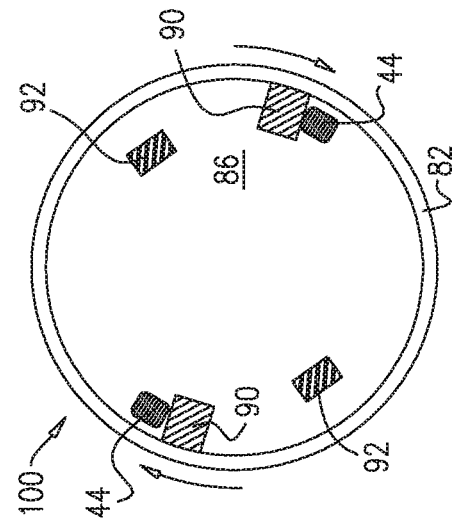
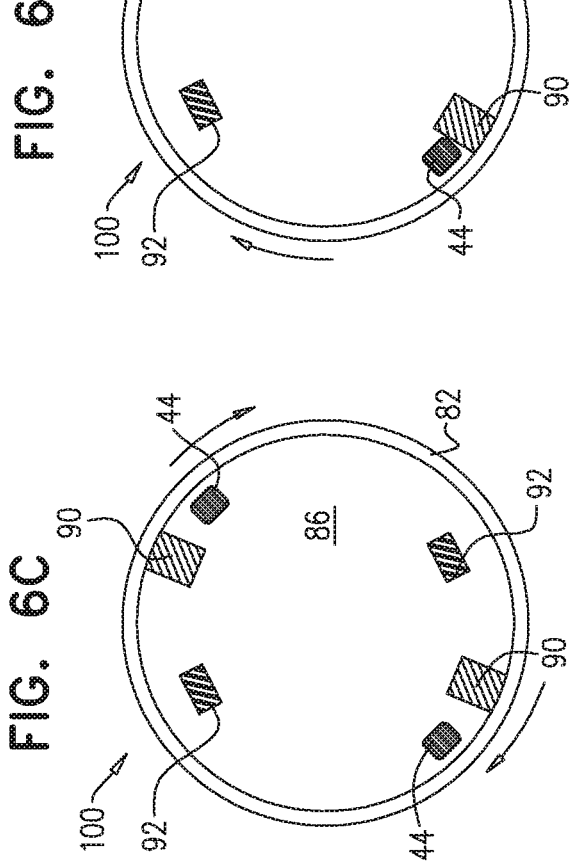

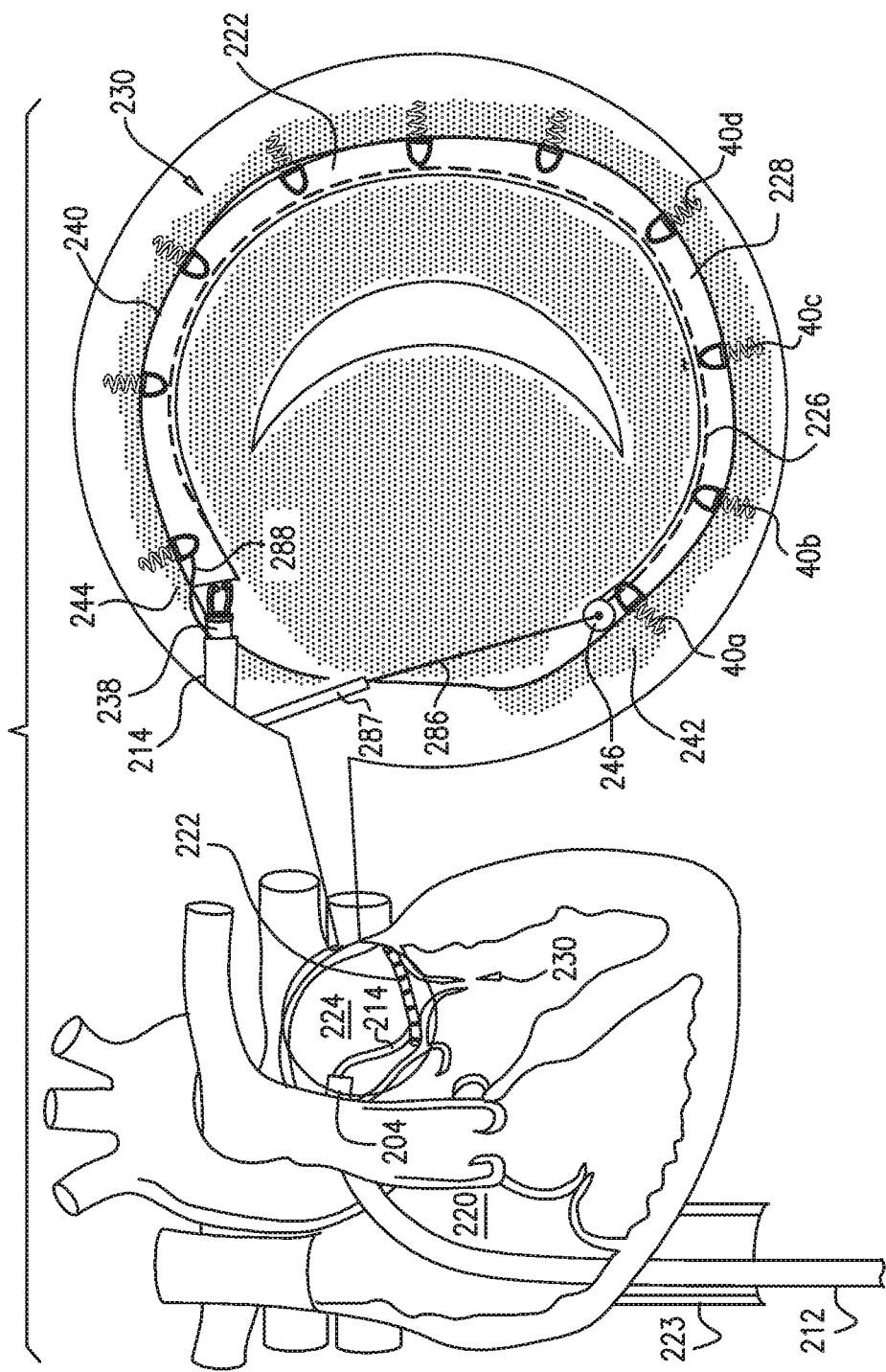

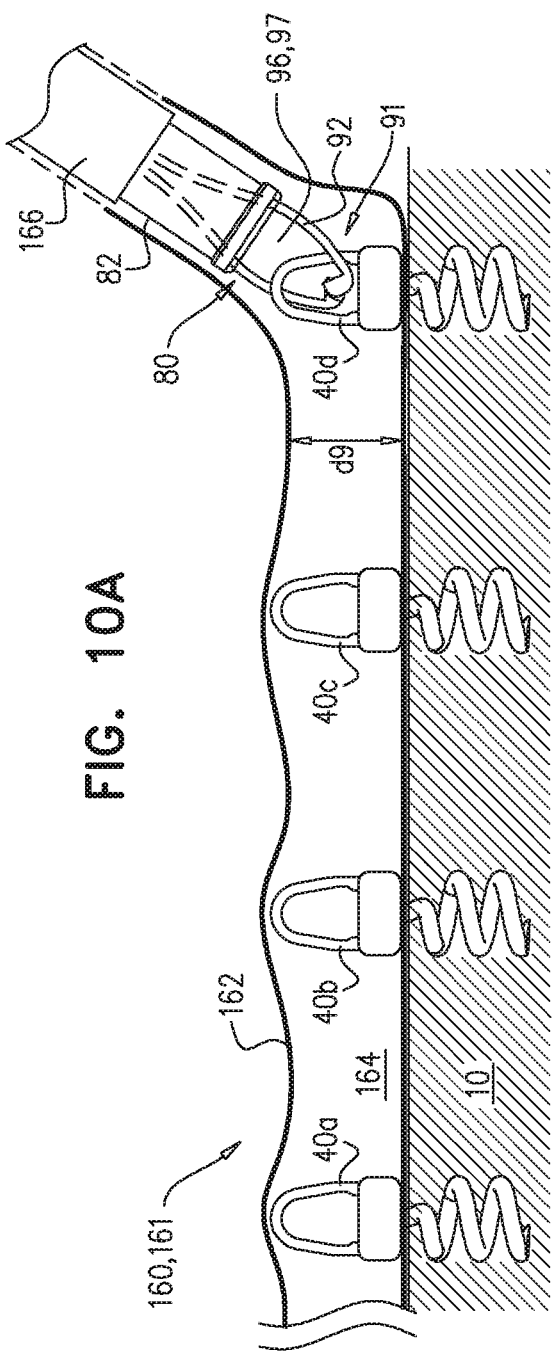
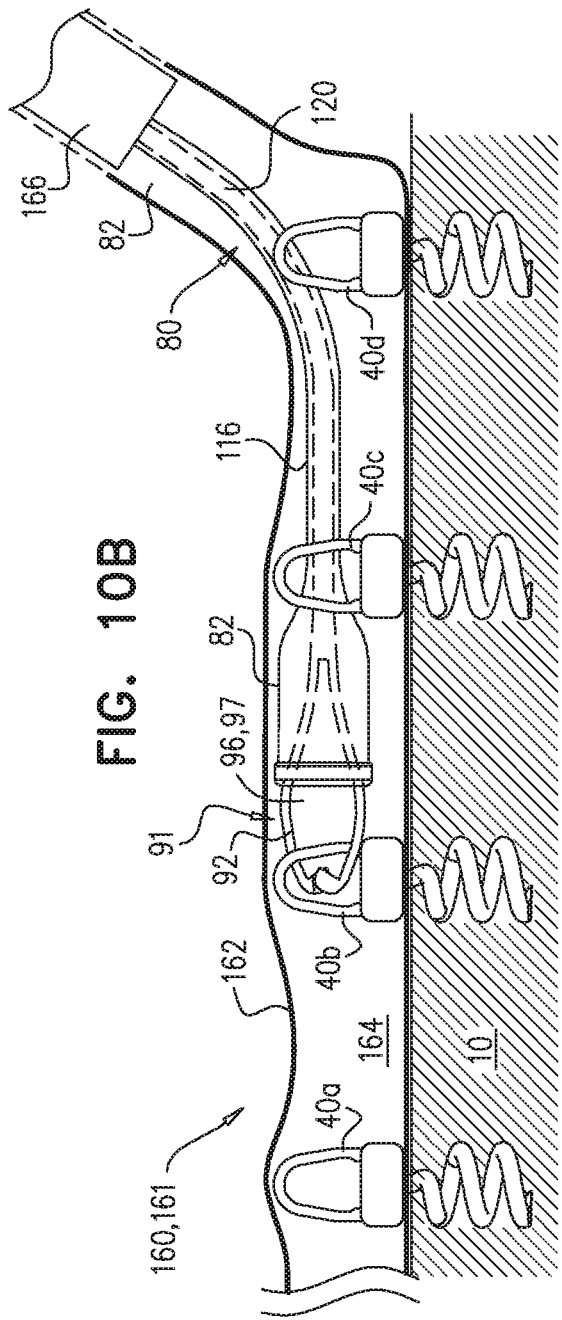

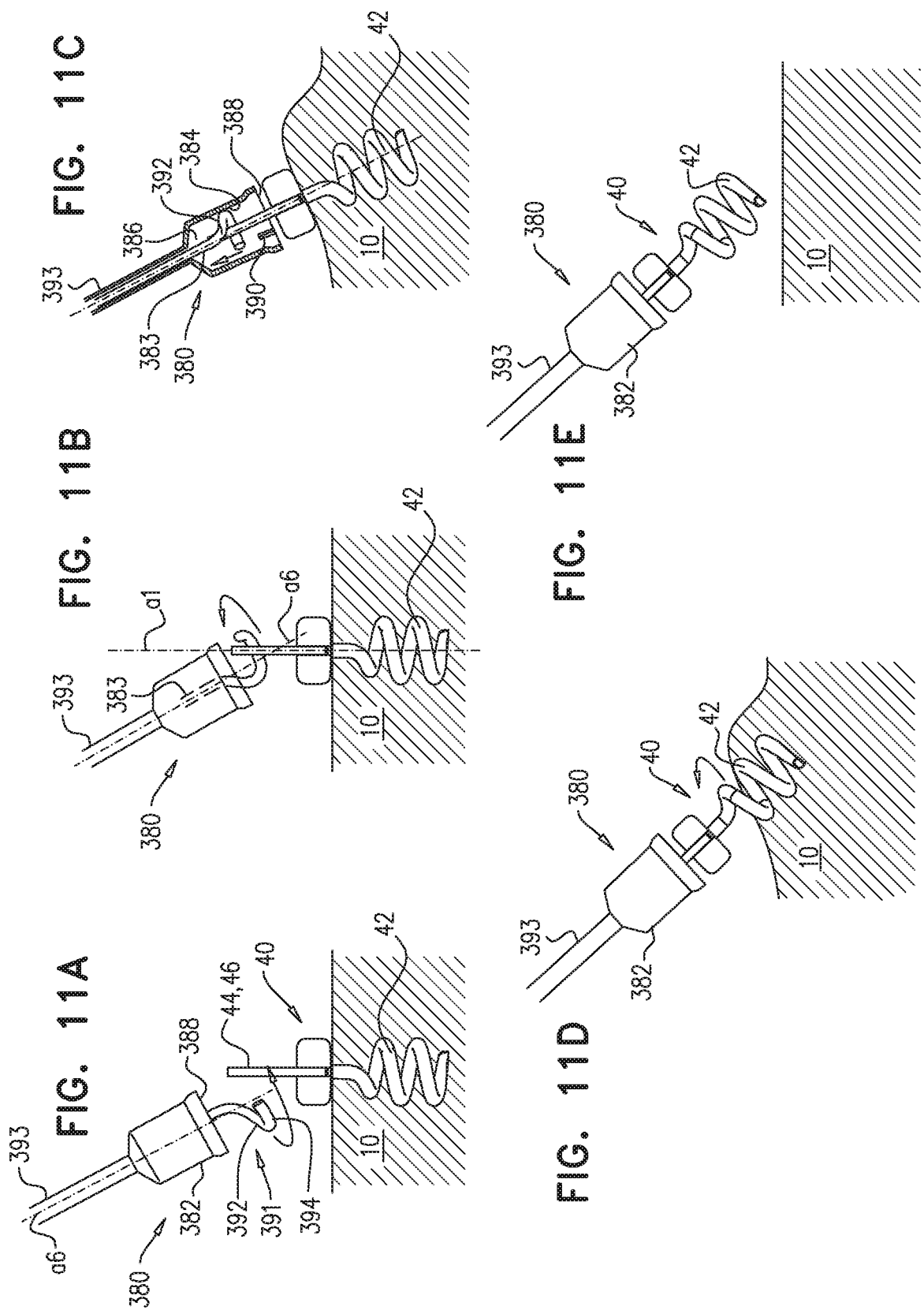

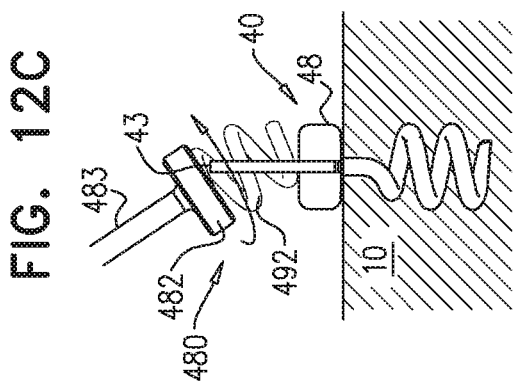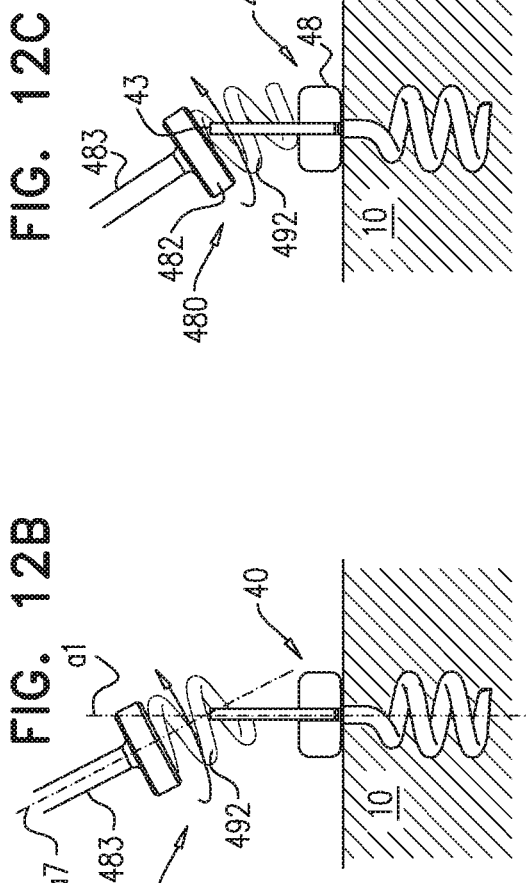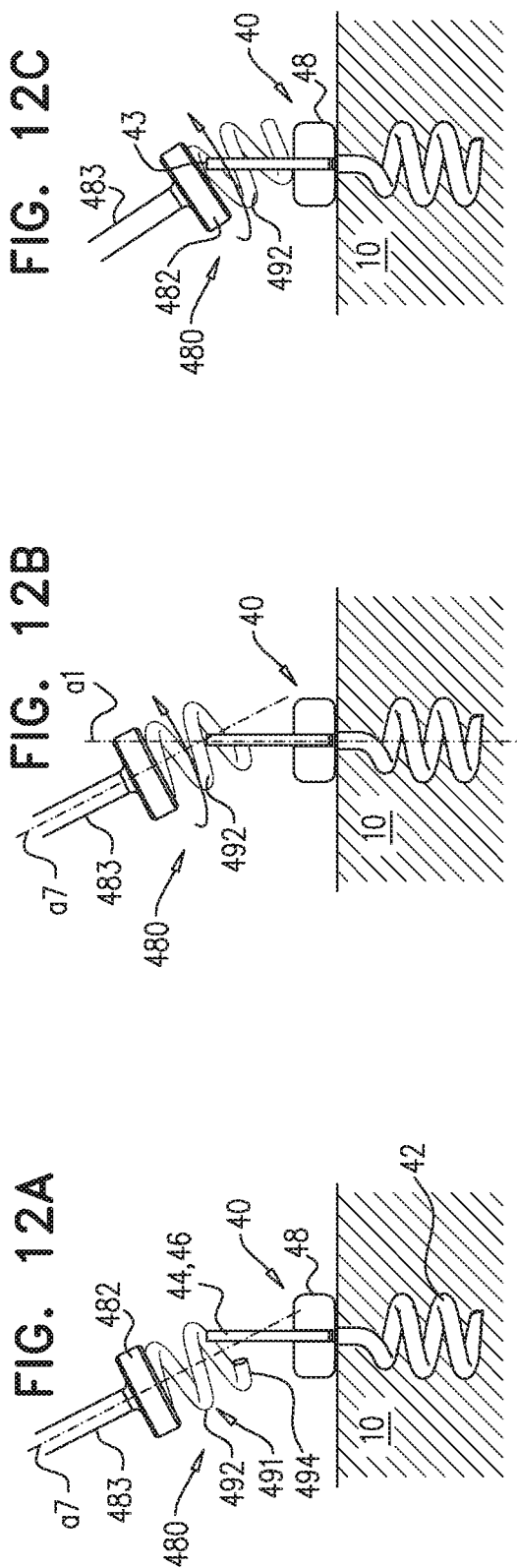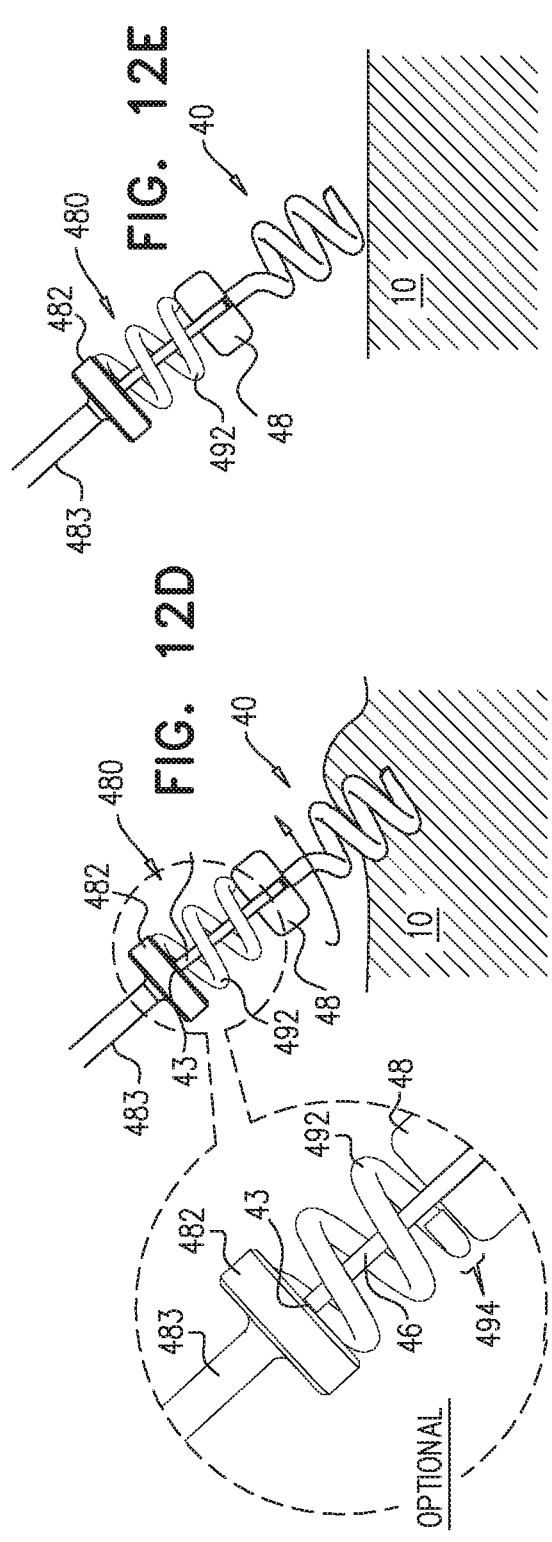

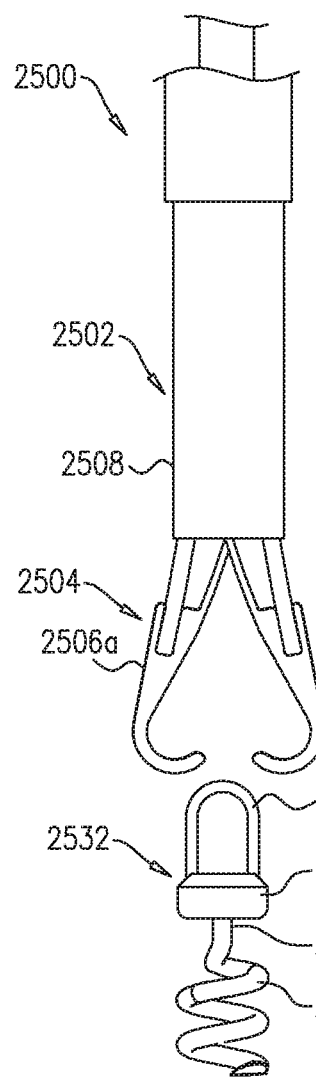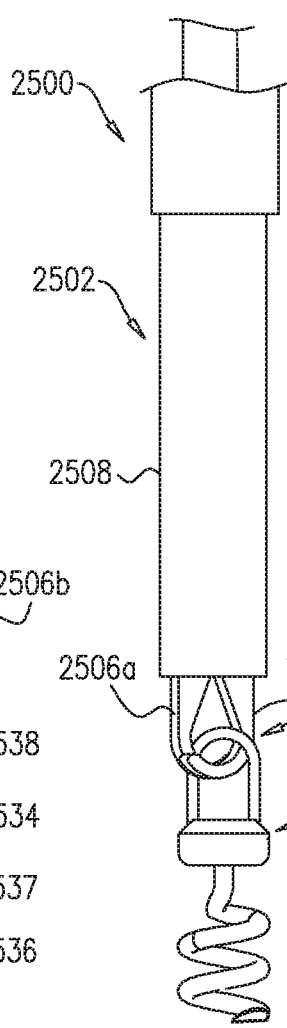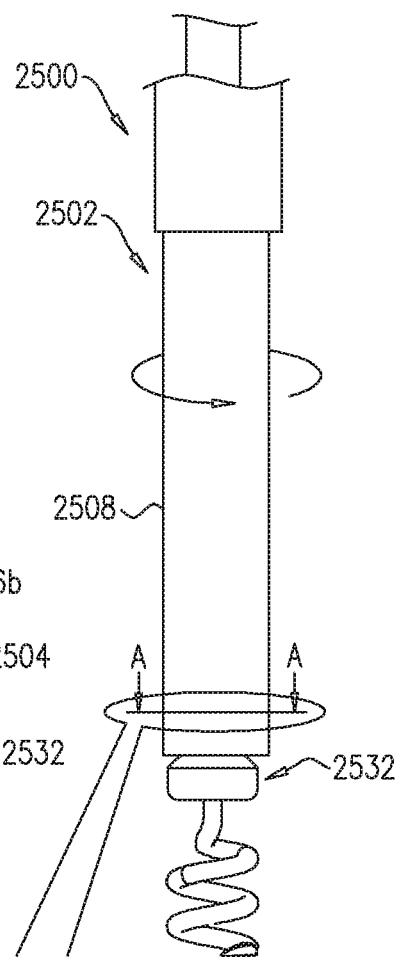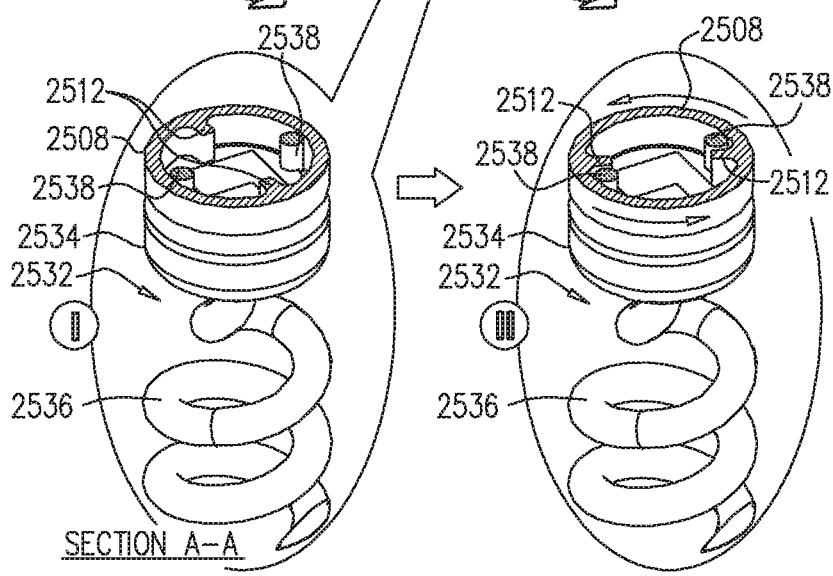

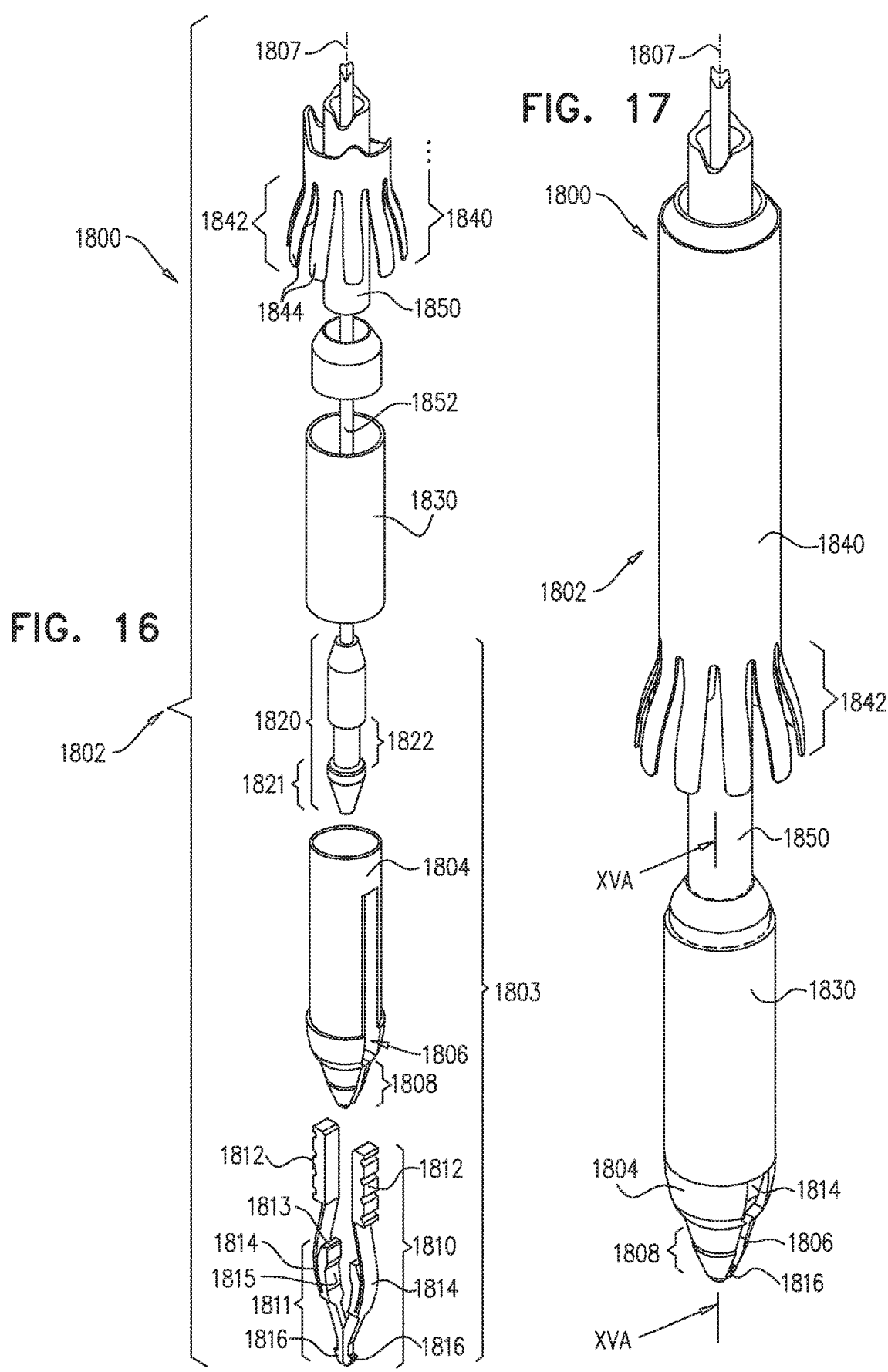

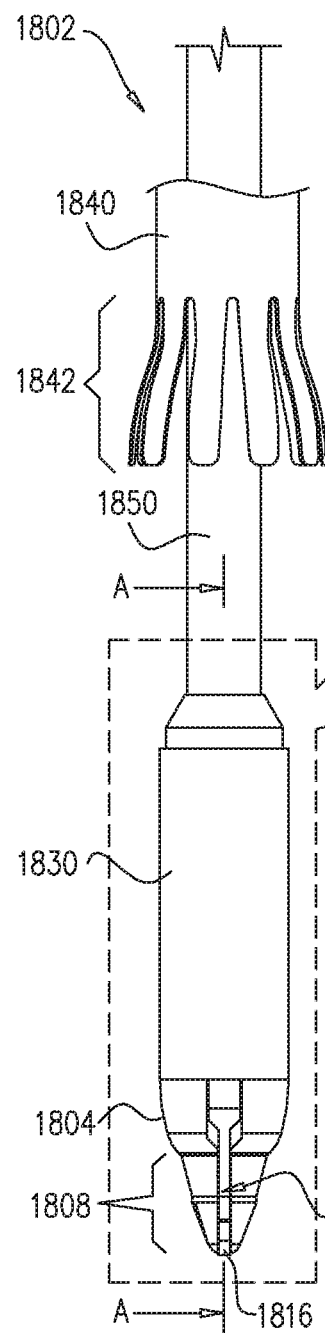
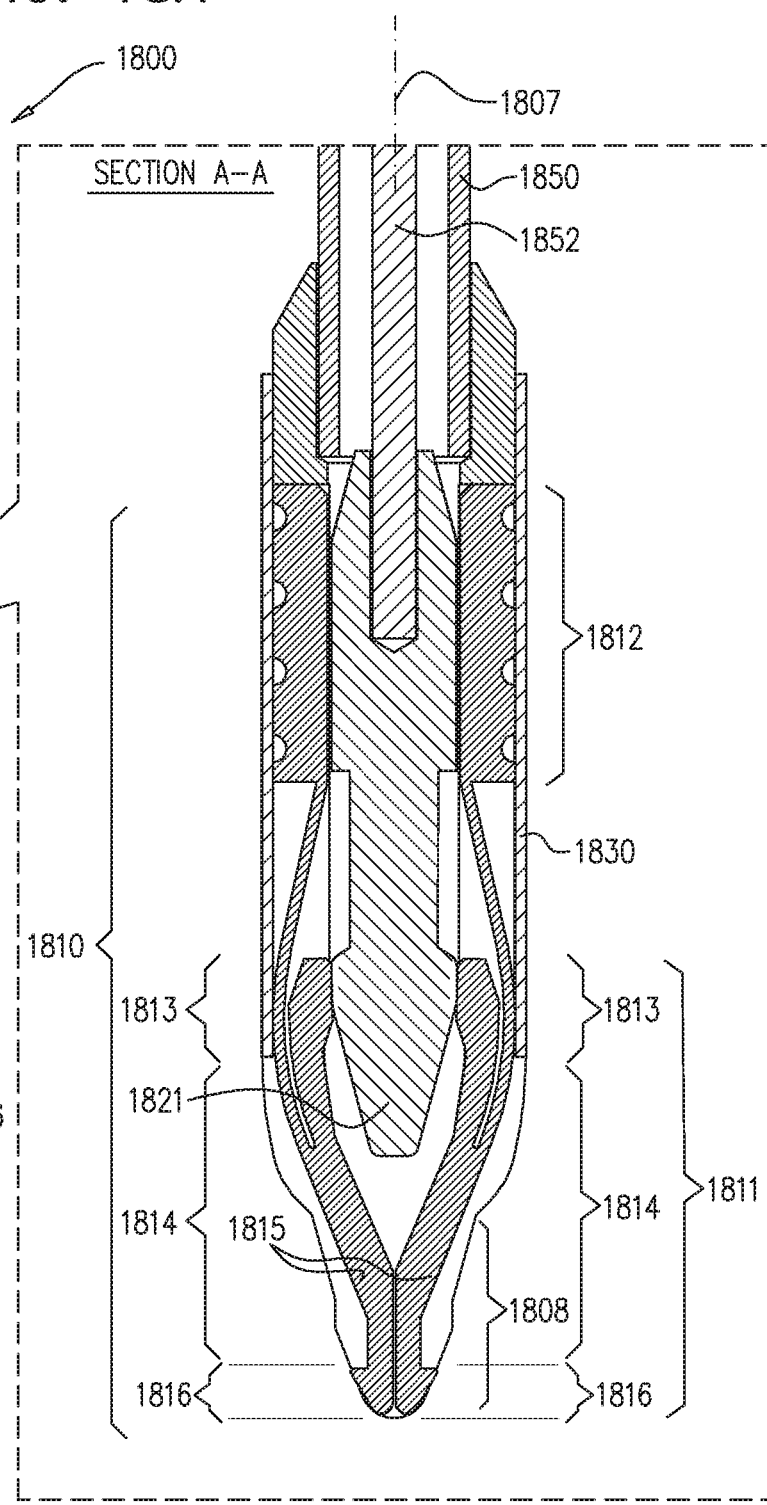
FIG. 18A

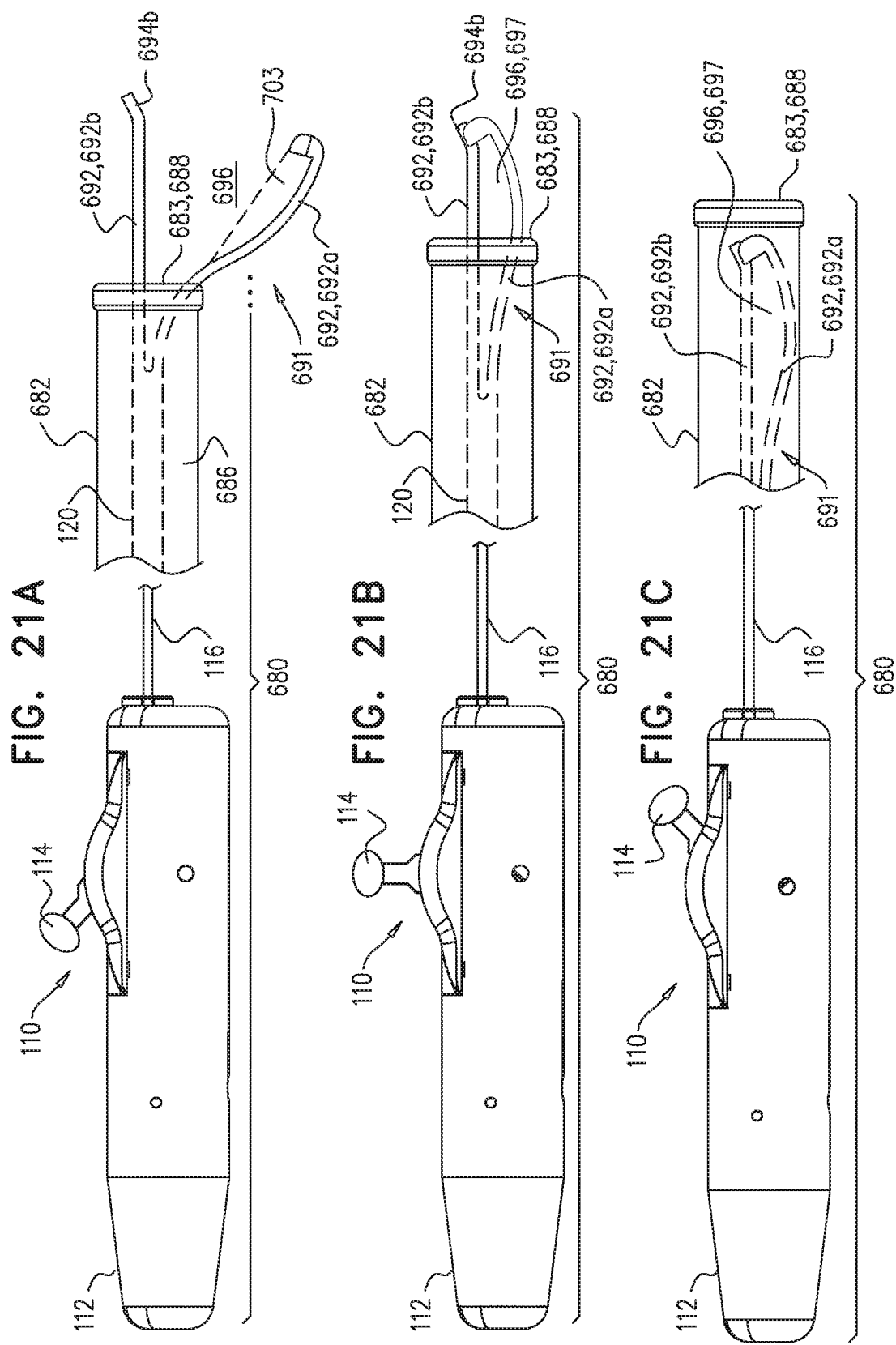

PERCUTANEOUS TISSUE ANCHOR TECHNIQUES

CROSS-REFERENCES TO RELATED APPLICATIONS

The present application is a Continuation of U.S. Ser. No. 14/437,062 to Herman et al., which published as US 2015/0272586, and which is the US National Phase of PCT application IL2013/050861 to Herman et al., filed Oct. 23, 2013, which published as WO 2014/064695, and which claims priority from:

U.S. Provisional Patent Application 61/717,303 to Sheps et al., titled "Controlled steering functionality for implant-delivery tool," filed Oct. 23, 2012;

U.S. Provisional Patent Application 61/745,848 to Sheps et al., titled "Controlled steering functionality for implant-delivery tool," filed Dec. 26, 2012;

U.S. Provisional Patent Application 61/784,042 to Herman et al., titled "Percutaneous tissue anchor techniques," filed Mar. 14, 2013; and U.S. Provisional Patent Application 61/820,979 to Sheps et al., titled "Controlled steering functionality for implant-delivery tool," filed May 8, 2013, all of which are incorporated herein by reference.

FIELD OF THE INVENTION

The present application relates in general to medical devices. More specifically, the present application relates to tissue anchors and tool for manipulation of tissue anchors, such as for percutaneous use.

BACKGROUND

Tissue anchors are used to facilitate implantation of medical implants, such as by coupling such implants to tissue. A tissue anchor may be driven through the implant and into the tissue while the implant is held in place. Alternatively, the tissue anchor may be implanted before introduction of the medical implant, and the medical implant subsequently coupled to the tissue anchor.

SUMMARY OF THE INVENTION

Tissue anchor apparatus, and techniques for use thereof, are described. For some applications, a tool is described for manipulating tissue anchors. For some applications, the tool is configured for retrieval of already-implanted tissue anchors. For some applications, the tool is configured to be coupled to a tissue anchor at a non-zero angle with respect to the tissue anchor, and to subsequently be aligned with the tissue anchor. For some applications, the tool is configured to be advanced through a sleeve of an implant that has been implanted using tissue anchors, and to de-anchor at least one of the tissue anchors, thereby de-anchoring at least part of the sleeve from the tissue.

For some applications, a tissue anchor is described having a helical tissue-coupling element and an engaging head that comprises an eyelet. For some such applications, the tool is configured to be initially articulatably coupled to the tissue anchor (e.g., to the eyelet), and to be subsequently rigidly-coupled to the tissue anchor. For some such applications, the tool is configured to couple to the eyelet such that, together, the eyelet and an anchor-engaging element of the tool resemble links in a chain.

For some applications, an anchor driver is described for implanting the tissue anchor.

There is therefore provided, in accordance with an application of the present invention, apparatus for use with a tissue anchor, the apparatus including:
a first element including:
a first arm; and
a second arm, shaped to define a concavity, and movably coupled to the first arm such that:
the concavity faces the first arm, and defines at least part of a space,
in an open state of the first element, a gap is defined between a distal portion of the first arm and a distal portion of the second arm through which a portion of the tissue anchor is movable into the space, and
in a closed state of the first element, the portion of the tissue anchor is not movable through the gap; and
a second element, movable with respect to the first element such that, while (1) the portion of the tissue anchor is disposed within the space, and (2) the first element is in the closed state thereof:
in a first position of the second element with respect to the first element, the portion of the tissue anchor is movable within the space, and
in a second position of the second element with respect to the first element, the second element is positioned to apply torque to the tissue anchor by rotation of the second element.

In an application, in the open state, the distal portion of at least the second arm is disposed at an angle between 60 degrees and 80 degrees with respect to a longitudinal axis of the second element.

In an application, in the open state, the distal portion of at least the second arm protrudes away from the second portion and toward a central longitudinal axis of the apparatus.

In an application, the first arm and the second arm are disposed on a plane, and are more resistant to bending in-plane than off-plane.

In an application:
the first arm is shaped to define another concavity that defines at least part of the space, and
the first arm is coupled to the second arm such that the concavity defined by the first arm faces the concavity defined by the second arm.

In an application, the portion of the tissue anchor includes a bar that has a thickness, and the gap has a width that is at least 5 times greater than the thickness of the bar.

In an application:
the portion of the tissue anchor includes a bar that has a thickness, and
in the first position of the second element with respect to the first element the first arm and the second arm shape the space to define an aperture having a width that is at least 3 times greater than the thickness of the bar.

In an application:
the portion of the tissue anchor includes a bar that has a transverse cross-sectional area, and
in the first position of the second element with respect to the first element the first arm and the second arm shape the space to define an aperture defining an area that is at least 10 times greater than the transverse cross-sectional area of the bar.

In an application, in the first position of the second element with respect to the first element, the first arm and the second arm shape the space to define an aperture having (1) a depth, and (2) a width that is greater than the depth of the aperture.

In an application, the apparatus is configured such that, while (1) the portion of the tissue anchor is disposed within the space, and (2) the first element is in the closed state thereof:

when the first element is moved proximally, the first element applies a proximally-directed pulling force to the tissue anchor via contact between the first element and the portion of the tissue anchor, and in the second position of the second element with respect to the first element, the second element is positioned to apply torque to the tissue anchor via contact between the first element and the tissue anchor.

In an application:

the second element includes a housing that defines a compartment, in the first position, at least part of the first element is disposed outside of the compartment, and the second element is movable from the first position to the second position such that at least part of the first element becomes disposed within the compartment.

In an application, in the open state of the first element, the gap is at least 1.5 times as great as a transverse width of the compartment.

In an application, the housing is configured to receive the portion of the tissue anchor at any of a plurality of rotational positions of the portion of the tissue anchor with respect to the housing.

In an application, the housing is configured to receive the portion of the tissue anchor at a continuum of rotational positions of the portion of the tissue anchor with respect to the housing, the continuum of rotational positions spanning at least 90 degrees.

In an application:

the portion of the tissue anchor includes a bar that defines at least part of an eyelet that defines a plane, the eyelet having a width on the plane, the compartment has a transverse width that is greater than the width of the eyelet, and the housing including one or more protrusions that protrude radially inward into the compartment such that a distance across the compartment between the protrusions is smaller than the width of the eyelet.

In an application:

the apparatus further includes an extracorporeal controller including a handle and an adjuster, the controller configured to move the second element with respect to the first element, the adjuster is coupled to the housing via a tubular longitudinal member and is configured to reversibly move the at least part of the first element into and out of the compartment by reversibly moving the housing further and closer from the handle, and the apparatus further includes a second longitudinal member that is disposed through tubular longitudinal member, and the handle is coupled to the first element via the second longitudinal member, such that a distance along the longitudinal member between the handle and the housing is fixed.

In an application, the housing is configured to move the first element from the open state to the closed state by moving with respect to the first element.

In an application, the apparatus is configured such that, when the second element moves from the first position to the second position, the housing inhibits movement of the portion of the tissue anchor within the space.

In an application:

the apparatus further includes:

the tissue anchor; and a tool for use with the tissue anchor, a distal portion of the tool including the first element and the second element, while (1) the portion of the tissue anchor is disposed within the space, and (2) the first element is in the closed state thereof:

in the first position of the second element with respect to the first element, the tissue anchor is in an articulatably-coupled state with respect to the tool, in which the distal portion of the tool is deflectable with respect to the tissue anchor, and in the second position of the second element with respect to the first element, the housing inhibits deflection of the distal portion of the tool with respect to the tissue anchor.

In an application, in the articulatably-coupled state, the distal portion of the tool is deflectable in at least 1 steradian with respect to the tissue anchor.

In an application, in the articulatably-coupled state, the distal portion of the tool is deflectable in at least 180 degrees with respect to the tissue anchor.

In an application, in the articulatably-coupled state, the tool is rotatable with respect to the tissue anchor.

In an application, the apparatus further includes (1) an implant including a sleeve, and (2) a tool for use with the tissue anchor, a distal portion of the tool including the first element and the second element, and:

the sleeve:

defines a lumen and a proximal opening that provides access to the lumen, is configured to be anchored to tissue of the subject by the tissue anchor in a manner in which (1) a tissue-engaging element of the tissue anchor is disposed in the tissue, and (2) the portion of the tissue anchor is disposed in the lumen, and the distal portion of the tool is:

configured to be transluminally advanced to the implant, dimensioned to access the lumen via the proximal opening, and configured to be coupled to the portion of the tissue anchor while within the lumen.

In an application, in the open state of the first element, the gap between the distal portion of the first arm and the distal portion of the second arm is at least 20 percent as great as a transverse cross-sectional width of the lumen.

In an application:

the tissue anchor is one of a plurality of tissue anchors, the apparatus is for use with the plurality of tissue anchors, the sleeve has a longitudinal axis, and is configured to be anchored to the tissue of the subject by the plurality of tissue anchors at a respective plurality of longitudinal sites of the sleeve, and the distal portion of the tool is dimensioned to access the tissue anchor while at least another one of the plurality of tissue anchors is disposed between the tissue anchor and the proximal opening of the sleeve.

In an application, the apparatus further includes the tissue anchor, and:

the portion of the tissue anchor includes a bar that defines at least part of an eyelet that defines a plane, the tissue anchor has a longitudinal axis that lies on the plane, and the eyelet has a height along the longitudinal axis of the tissue anchor that is greater than a width of the eyelet, the width of the eyelet being on the plane and orthogonal to the longitudinal axis.

In an application, the bar is shaped to define an arch portion of the eyelet, and the arch portion is generally parabolic.

In an application, at least the first arm is curved.

In an application:
the apparatus further includes a tool having a distal end that includes the first element and the second element, and
the at least first arm is generally sigmoid and has an inwardly-convex proximal portion that curves away from a longitudinal axis of the distal end of the apparatus.

In an application, the curvature of the at least first arm defines an inwardly-concave portion that defines the concavity.

There is further provided, in accordance with an application of the present invention, apparatus, including:
a tissue anchor including a tissue-engaging element and a head that includes a bar having a transverse cross-sectional area; and
a tool including (1) a first part that includes an arm, and (2) a second part coupled to the first part such that:
a space is defined between the first arm and the other part of the tool,
in an open state, a gap is defined between the arm and the second part of the tool, the bar being movable through the gap and into the space, and
in a closed state, the bar is not movable through the gap, and the space is shaped to define an aperture that has an area that is at least 10 times greater than the transverse cross-sectional area of the bar.

There is further provided, in accordance with an application of the present invention, a method including:
sliding, through a catheter, an anchor-manipulating tool, while the anchor-manipulating tool is coupled to a tissue anchor and articulatable with respect to the tissue anchor;
inhibiting articulation between the anchor-manipulation tool and the tissue anchor; and
while the articulation is inhibited, using the anchor-manipulating tool, performing an action selected from the group consisting of: driving the tissue anchor into tissue of a subject, and removing the tissue anchor from tissue of the subject.

In an application, the step of inhibiting is performed subsequently to the step of sliding.

In an application, the step of inhibiting is performed prior to the step of sliding.

There is further provided, in accordance with an application of the present invention, apparatus for use with a tissue of a subject, the apparatus including:
a tissue anchor, including an engaging head and a tissue-coupling element, reversibly anchorable to the tissue; and
an anchor-retrieval tool, including:
an anchor-engaging element including one or more arms, configured to be coupled to the engaging head,
a housing that defines a compartment therein, and
a controller, including an adjuster configured to move at least part of the anchor-engaging element into and out of the compartment.

In an application, the adjuster is configured to move at least part of the anchor-engaging element into and out of the compartment by reversibly moving the housing, with respect to the anchor-engaging element along a longitudinal axis of the anchor-manipulation tool.

In an application, the engaging head includes a bar that defines an eyelet that has a width, and the compartment has a transverse width that is greater than the width of the eyelet.

In an application:
the one or more arms include at least a first arm and a second arm that define a space therebetween, and
the controller is configured to reversibly move the first arm and the second arm between (1) a first state in which a gap between a distal portion of the first arm and a distal portion of the second arm is at least 5 times greater than a thickness of the bar, and (2) a second state in which the gap is smaller than the thickness of the bar, and the space between the first arm and the second arm defines an aperture that has a width that is at least 3 times greater than the thickness of the bar.

In an application, a thickness of the one or more arms defines a depth of the aperture, and the width of the aperture is greater than the depth of the aperture.

In an application, the anchor-retrieval tool has a distal end that includes the anchor-engaging element and the housing, and the apparatus has at least two states, including:
an uncoupled state in which the anchor-engaging element is not in contact with the tissue anchor, and
an articulatably-coupled state in which:
the engaging head inhibits movement of the anchor-engaging element away from the tissue anchor, and
the distal end of the anchor-retrieval tool is deflectable with respect to the tissue anchor,
the controller being configured to facilitate transition of the apparatus from the uncoupled state to the articulatably-coupled state.

In an application, the engaging head includes an eyelet, and the controller is configured to facilitate transition of the apparatus from the uncoupled state to the articulatably-coupled state by moving at least part of the one or more arms through the eyelet In an application, the at least two states further include a rigidly-coupled state in which the distal end of the anchor-retrieval tool is inhibited from deflecting with respect to the tissue anchor.

In an application, the adjuster is configured to move the apparatus from the articulatably-coupled state into the rigidly-coupled state by moving at least part of the engaging head into the compartment by moving the at least part of the anchor-engaging element into the compartment.

In an application, when the apparatus is in the rigidly-coupled state, the anchor-manipulation tool is configured to apply a de-anchoring force the tissue anchor.

In an application, the anchor-manipulation tool is configured to apply a rotational de-anchoring force to the anchor.

In an application, the anchor-manipulation tool is configured to apply the rotational de-anchoring force by the housing rotating around a longitudinal axis of the anchor-manipulation tool.

In an application, the one or more arms are curved.

In an application, the one or more arms include exactly one arm.

In an application, the exactly one arm is shaped to define a hook.

In an application, the controller is configured to move the housing, with respect to the hook, along a longitudinal axis of the anchor-manipulation tool.

There is further provided, in accordance with an application of the present invention, apparatus for use with a tissue of a subject, the apparatus including:

a tissue anchor including an engaging head including an eyelet, and a tissue-coupling element reversibly anchorable to the tissue; and an anchor-manipulation tool:
including, at a distal portion thereof, an anchor-engaging element including a curved arm, configured to be coupled to the tissue anchor by moving through the eyelet, and
being configured, while the anchor-engaging element is coupled to the tissue anchor, to apply a rotational de-anchoring force to the tissue anchor.

In an application, the curved arm is generally helical, and is configured to be coupled to the eyelet by being rotated with respect to the eyelet.

In an application, the tissue-coupling element is generally helical and has a handedness, and the curved arm has a handedness that is opposite to the handedness of the tissue-coupling element.

In an application, the anchor-engaging element includes at least a first arm and a second arm, the curve of each of the arms defining a respective concavity, and the arms positioned such that the concavity of the first arm faces the concavity of the second arm.

In an application, the anchor-engaging element further includes a housing that defines a compartment therein, and an adjuster that is configured to move at least part of each of the arms into and out of the compartment.

In an application,
when the anchor-engaging element is coupled to the tissue anchor, the anchor-manipulation tool is configured to move at least part of the eyelet into the compartment by the at least part of each of the arms moving into the compartment, and
the housing is configured to apply the rotational de-anchoring force to the tissue anchor by the housing being rotated while the at least part of the eyelet is disposed within the compartment.

In an application, the anchor-engaging element is configured to be coupled to the tissue anchor by being rotated with respect to the tissue anchor, and the anchor-manipulation tool is configured to apply the rotational de-anchoring force to the tissue anchor by at least part of the anchor-engaging element being rotated with respect to the tissue anchor.

In an application, the anchor-engaging element further includes a housing that defines a compartment therein, and an adjuster that is configured to move at least part of the arm into and out of the compartment.

In an application,
when the anchor-engaging element is coupled to the tissue anchor, the anchor-manipulation tool is configured to move at least part of the eyelet into the compartment by the at least part of the arm moving into the compartment, and
the housing is configured to apply the rotational de-anchoring force to the tissue anchor by the housing being rotated while the at least part of the eyelet is disposed within the compartment.

In an application, the curved arm is generally helical, is configured to be coupled to the eyelet by being rotated with respect to the eyelet, and is configured to apply the rotational de-anchoring force to the tissue anchor by being further rotated with respect to the eyelet.

There is further provided, in accordance with an application of the present invention, apparatus for use with a tissue of a subject, the apparatus including:
a tissue anchor, including:
an engaging head, including a coupling eyelet that defines a plane, and
a helical tissue-coupling element, reversibly anchorable to the tissue, and having a central helix axis that lies on the plane defined by the eyelet; and
an anchor driver, having a distal portion that is transluminally advanceable toward the tissue, and including:
a casing that defines a slot dimensioned to receive at least part of the eyelet therein, and
a detent, configured to reversibly inhibit movement of the eyelet with respect to the slot,
the anchor driver being configured to anchor the tissue anchor to the tissue by rotating the tissue anchor by applying a rotational force to the eyelet.

In an application, the slot is dimensioned to receive the at least part of the eyelet snugly.

In an application, the anchor driver further includes a controller, configured to move the detent between (i) a closed state in which the at least part of the eyelet is inhibited from exiting the slot, and (ii) an open state in which the at least part of the eyelet is slidable out of the slot.

In an application:
the casing defines a recess,
at least part of the detent moves into the recess when the detent moves into the open state thereof, and
the controller includes a rod, configured to move the detent into the closed state thereof by the rod being slid into at least part of the recess.

In an application, the apparatus further includes an anchor-retrieval tool, transluminally advanceable independently of the anchor driver.

In an application, the anchor-retrieval tool includes:
an anchor-engaging element including one or more arms, configured to be coupled to the engaging head,
a housing that defines a compartment therein, and
a retrieval-tool controller, including an adjuster configured to move at least part of the anchor-engaging element into and out of the compartment.

In an application, the anchor-retrieval tool:
includes, at a distal portion thereof, an anchor-engaging element including a curved arm, configured to be coupled to the tissue anchor by moving through the eyelet, and
is configured, while the anchor-engaging element is coupled to the tissue anchor, to apply a rotational de-anchoring force to the tissue anchor.

In an application:
the anchor-retrieval tool includes:
at a distal portion of the anchor-retrieval tool, an anchor-engaging element and an anchor-engaging-element actuator, and
at a proximal portion of the anchor-retrieval tool, a retrieval-tool controller configured to control the anchor-engaging-element actuator, the apparatus has at least two states:
(1) an uncoupled state in which the anchor-engaging element is not in contact with the tissue anchor, and
(2) an articulatably-coupled state in which:
the engaging head at least in part inhibits movement of the anchor-engaging element away from the tissue anchor, and
the distal portion of the anchor-retrieval tool is deflectable with respect to the tissue anchor,
the anchor-engaging-element actuator is configured to facilitate transition of the apparatus from the uncoupled state to the articulatably-coupled state, and
the anchor-retrieval tool, in at least one of the at least two states, being configured to apply a de-anchoring force the tissue anchor.

There is further provided, in accordance with an application of the present invention, apparatus, including:
an implant including a sleeve that includes a lateral wall that defines a lumen having a transverse cross-sectional diameter, and configured to be transluminally implanted in a subject;
at least one tissue anchor including a coupling head and a tissue-engaging element, configured to be transluminally advanced to the implant, and to anchor the implant in the subject by the tissue-engaging element being driven through the lateral wall and into a tissue of the subject; and
an anchor-retrieval tool including an anchor-engaging element including two arms, the anchor-engaging element configured:
to be transluminally advanced to the implant and into the lumen of the implant,
to be moved into a position in which a gap between respective distal portions of the two arms is at least 20 percent as great as the transverse cross-sectional diameter of the lumen,
to be subsequently coupled to the coupling head, and
to subsequently apply a de-anchoring force to the tissue anchor.
In an application, the anchor-engaging element is configured to be moved into a position in which a gap between respective distal portions of the two arms is at least 50 percent as great as the transverse cross-sectional diameter of the lumen.
In an application, the anchor-engaging element is configured to be moved into a position in which a gap between respective distal portions of the two arms is at least 80 percent as great as the transverse cross-sectional diameter of the lumen.
There is further provided, in accordance with an application of the present invention, apparatus for use with a tissue of a subject, the apparatus including:
a tissue anchor, including an engaging head and a tissue-coupling element, and reversibly anchorable to the tissue; and
an anchor-manipulation tool including:
at a distal portion of the tool, an anchor-engaging element and an anchor-engaging-element actuator, and
at a proximal portion of the tool, a controller configured to control the anchor-engaging-element actuator,
the apparatus having at least two states, including:
an uncoupled state in which the anchor-engaging element is not in contact with the tissue anchor, and
an articulatably-coupled state in which:
the engaging head at least in part inhibits movement of the anchor-engaging element away from the tissue anchor, and
the distal portion of the anchor-manipulation tool is deflectable with respect to the tissue anchor,
the anchor-engaging-element actuator being configured to facilitate transition of the apparatus from the uncoupled state to the articulatably-coupled state, and
the anchor-manipulation tool, in at least one of the at least two states, being configured to apply a de-anchoring force the tissue anchor.
In an application, in the articulatably-coupled state, the distal portion of the anchor-manipulation tool is rotatable with respect to the tissue anchor.
In an application, the anchor-manipulation tool is configured to rotate the tissue anchor by applying the de-anchoring force to the tissue anchor.

In an application, the at least two states further include a rigidly-coupled state in which the distal portion of the anchor-manipulation tool is inhibited from deflecting with respect to the tissue anchor.
In an application, the anchor-manipulation tool is configured to apply the de-anchoring force to the tissue anchor while the apparatus is in the rigidly-coupled state.
In an application, the anchor-engaging-element actuator is configured to transition the apparatus from the articulatably-coupled state to the rigidly-coupled state.
In an application, the anchor-engaging-element actuator is configured to transition the apparatus from the articulatably-coupled state to the rigidly-coupled state by sliding, with respect to the anchor-engaging element, along a longitudinal axis of the distal portion of the tool.
In an application, in the articulatably-coupled state, the distal portion of the anchor-manipulation tool is deflectable in at least 1 steradian with respect to the tissue anchor.
In an application, in the articulatably-coupled state, the distal portion of the anchor-manipulation tool is deflectable in at least 3 steradians with respect to the tissue anchor.
In an application, in the articulatably-coupled state, the distal portion of the anchor-manipulation tool is deflectable in at least 7 steradians with respect to the tissue anchor.
There is further provided, in accordance with an application of the present invention, a method for use with a tissue anchor that is implanted in a tissue of a subject, the method including:
advancing a tool toward the tissue anchor;
coupling the tool to the tissue anchor such that a longitudinal axis of the tool is disposed at a nonzero angle with respect to a longitudinal axis of the tissue anchor; and
subsequently aligning the longitudinal axis of the tool with the longitudinal axis of the tissue anchor.
In an application, at least a portion of the tissue anchor is disposed within a sleeve of an implant, and couples at least a portion of the implant to the tissue, and advancing the tool toward the tissue anchor includes advancing the tool at least partly through the sleeve of the implant.
In an application, aligning the longitudinal axis of the tool with the longitudinal axis of the tissue anchor includes aligning the longitudinal axis of the tool with the longitudinal axis of the tissue anchor by deforming the tissue of the subject.
In an application, deforming the tissue includes deforming the tissue by applying a force to the tissue anchor using the tool.
In an application, the tissue anchor includes an eyelet and the tool includes an anchor-engaging element and a housing that is slidable over the anchor-engaging element, and the method further includes facilitating aligning the longitudinal axis of the tool with the longitudinal axis of the tissue anchor by sliding the housing over at least part of the eyelet.
In an application, coupling the tool to the tissue anchor includes articulatably coupling the tool to the tissue anchor.
In an application, the method further includes, subsequently to aligning the longitudinal axis of the tool with the longitudinal axis of the tissue anchor, inhibiting articulation of the tissue anchor with respect to the tool.
In an application, inhibiting the articulation includes inhibiting the articulation by sliding a portion of the tool over a portion of the tissue anchor.
In an application, the tissue anchor includes an eyelet and the tool includes an anchor-engaging element and a housing that is slidable over the anchor-engaging element, and inhibiting the articulation includes inhibiting the articulation by sliding the housing over at least part of the eyelet.

In an application, the method further includes, subsequently to aligning the longitudinal axis of the tool with the longitudinal axis of the tissue anchor, applying a force to the anchor using the tool.

In an application, the method further includes de-anchoring the anchor from the tissue by applying the force to the anchor.

In an application, applying the force includes applying a rotational force to the anchor.

In an application, applying the rotational force to the anchor includes applying the rotational force to the anchor by rotating the tool, and the method further includes (1) after aligning the longitudinal axis of the tool with the longitudinal axis of the anchor, and (2) before applying the rotational force to the anchor, rotating the tool without applying the rotational force to the anchor.

There is further provided, in accordance with an application of the present invention, apparatus for use with a tissue anchor, the tissue anchor including a tissue-coupling element and a bar that defines at least part of a coupling eyelet coupled to the tissue-coupling element, the coupling eyelet having a width, the apparatus including:

a housing:
  having an inner surface that defines, within the housing, a compartment, the compartment having a transverse width that is greater than the width of the eyelet,
  including at least two protrusions that protrude radially inward from the inner surface into the compartment, such that a distance across the compartment between the protrusions is smaller than the width of the eyelet, and
  shaped to define, at a distal end of the housing, an opening into the compartment; and at least two arms including at least a first arm and a second arm, each of the arms defining a distal portion thereof, the arms defining a space therebetween, and being movable between:
  an extended position in which at least the distal portion of each arm is disposed outside the compartment, and the distal portion of the first arm and the distal portion of the second arm define a gap therebetween through which at least part of the bar is movable into the space, and
  a retracted position in which at least part of the distal portion of each arm is disposed inside the compartment, and the first arm and the second arm define a loop that shapes the space to define an aperture, the apparatus being configured such that as the arms move from the extended position toward the retracted position, the arms form the loop before reaching the retracted position.

In an application, the first arm and the second arm are disposed on a plane, and are more resistant to bending in-plane than off-plane.

In an application, the transverse width of the compartment is between 5 percent and 30 percent greater than the width of the eyelet.

In an application, the apparatus is configured to be advanced percutaneously into a subject.

In an application, in the extended position, the distal portion of each arm is disposed an angle between 60 degrees and 80 degrees with respect to the longitudinal axis.

In an application, the compartment defined by the inner surface of the housing is generally cylindrical, and the transverse width of the compartment includes a transverse diameter of the compartment.

In an application, the arms are configured to progressively form the loop responsively to being progressively moved into the compartment.

In an application, the compartment is generally cylindrical, and the transverse width includes a transverse diameter of the generally cylindrical compartment.

In an application, the tissue anchor has a longitudinal axis, the apparatus has a longitudinal axis, and the apparatus is configured to engage the coupling eyelet of the tissue anchor by the bar moving through the gap into the space, at any of at least 180 degrees of deflection of the longitudinal axis of the apparatus in a plane in which the longitudinal axis of the tissue anchor lies, and at any of at least 300 degrees of deflection of the longitudinal axis of the apparatus around the longitudinal axis of the tissue anchor.

In an application, the housing is configured to receive the eyelet at any of a plurality of rotational positions of the eyelet with respect to the housing.

In an application, the housing is configured to receive the eyelet at a continuum of rotational positions of the eyelet with respect to the housing.

In an application:
  the at least two protrusions include a first protrusion and a second protrusion,
  the apparatus has a longitudinal axis,
  the first protrusion and the second protrusion define a transverse axis therebetween, the transverse axis being orthogonal to the longitudinal axis of the apparatus,
  the eyelet defines a plane, and
  the housing is configured to receive the eyelet at a continuum of rotational positions of the plane of the eyelet with respect to the transverse axis, the continuum of rotational positions spanning at least 90 degrees around the longitudinal axis of the apparatus.

In an application, the housing is configured such that the continuum of rotational positions spans at least 150 degrees around the longitudinal axis of the apparatus.

In an application, the housing is configured to receive the eyelet at one or more continua of rotational positions of the plane of the eyelet, that span a total of at least 270 degrees around the longitudinal axis of the apparatus, with respect to the transverse axis.

In an application, the apparatus further includes an extracorporeal controller, including a handle and an adjuster, the adjuster being configured to move the arms between the extended position and the retracted position.

In an application:
  the adjuster is coupled to the housing via a tubular longitudinal member, and is configured to reversibly move the arms between the extended position and the retracted position by reversibly moving the housing further and closer from the handle, and
  the handle is coupled to the arms via a longitudinal member that passes through the tubular longitudinal member, such that a distance along the longitudinal member between the handle and the housing is fixed.

In an application, the handle is coupled to a proximal end of the longitudinal member that is exposed from a proximal end of the tubular longitudinal member.

In an application, the extracorporeal controller includes an indicator that indicates at least a state of the adjuster in which (1) the arms define the loop, and (2) the arms are not in the retracted position.

In an application, as the arms move from the extended position toward the retracted position, the arms deflect toward each other such that the distal portion of the first arm becomes closer to the distal portion of the second arm.

In an application, the distal portion of each arm defines a respective beveled edge, and the arms are configured such that when the arms move into the retracted position, the beveled edge of first arm mates with the beveled edge of the second arm.

In an application, a proximal portion of the first arm is coupled to a proximal portion of the second arm.

In an application, the arms are biased toward deflecting away from each other.

In an application, the proximal portion of the first arm is fixedly coupled to the proximal portion of the second arm, and each arm includes a resilient material, and is configured to progressively bend responsively to being progressively moved into the compartment.

In an application, in the extended position, the gap between the distal portion of the first arm and the distal portion of the second arm is greater than the transverse width of the compartment.

In an application, in the extended position, the gap between the distal portion of the first arm and the distal portion of the second arm is at least 1.5 times as great as the transverse width of the compartment.

In an application, the apparatus includes the tissue anchor.

In an application, the tissue anchor includes a base that couples the eyelet to the tissue-coupling element.

In an application, the tissue anchor has a longitudinal axis, and the eyelet has a height along the longitudinal axis that is at least 80 percent as great as the width of the eyelet.

In an application, the height of the eyelet is approximately equal to the width of the eyelet.

In an application, the height of the eyelet is greater than the width of the eyelet.

In an application, the height of the eyelet is at least 50 percent greater than the width of the eyelet.

In an application, the bar is shaped to define an arch portion of the eyelet, a crest of the arch portion being further from the tissue-coupling element than is a base of the arch portion.

In an application, the arch portion is generally parabolic.

In an application, the tissue anchor has a longitudinal axis, the eyelet has a height along the longitudinal axis, and any portion of the bar that is parallel to the longitudinal axis has a height along the longitudinal axis that is less than 50 percent of the height of the eyelet.

In an application, the arms are configured to be coupled to the coupling eyelet by trapping the at least part of the bar within the aperture by forming the loop while the at least part of the bar is disposed in the space between the arms.

In an application, the arms are configured to be articulatably coupled to the coupling eyelet.

In an application, the apparatus is configured such that, while the arms are coupled to the eyelet, when the arms move into the retracted position, at least part of the eyelet moves into the compartment.

In an application, the apparatus further includes the tissue anchor, the bar of the eyelet has a curvature, and the curvature of the bar of the eyelet facilitates the at least part of the eyelet moving into the compartment.

In an application, the apparatus further includes an overtube, slidable over the housing and, while the at least part of the eyelet is disposed within the compartment, slidable over at least part of the tissue anchor.

In an application, the apparatus is configured such that, when the at least part of the eyelet moves into the compartment, the housing inhibits articulation of the coupling eyelet with respect to the arms.

In an application, the apparatus is configured such that, while the at least part of the eyelet is disposed within the compartment, rotation of the housing with respect to the anchor presses the protrusions against the bar of the eyelet.

In an application, the apparatus is configured such that, while the at least part of the eyelet is disposed within the compartment, and the protrusions are pressed against the bar of the eyelet, further rotation of the housing with respect to the anchor rotates the anchor.

In an application, the apparatus includes the tissue anchor, and the tissue-coupling element of the tissue anchor includes a helical tissue-coupling element.

In an application, the apparatus is configured to facilitate screwing of the tissue-coupling element into tissue of a subject.

In an application, the apparatus is configured to facilitate unscrewing of the tissue-coupling element from tissue of a subject.

In an application, when the arms are coupled to the coupling eyelet, the loop and the eyelet resemble links in a chain.

In an application:
the arms each further define a proximal stem portion, a distal end of the proximal stem portion being coupled to the distal portion of the respective arm,
the housing has a central longitudinal axis from a proximal end to the distal end thereof,
in the extended position:
the proximal stem portion of each arm protrudes distally away from the housing and outward from the longitudinal axis, and
the distal portion of each arm protrudes from the distal end of the proximal stem portion and inward toward the longitudinal axis.

In an application, in the extended position, the distal portion of each arm protrudes from the distal end of the proximal stem portion distally away from the housing.

There is further provided, in accordance with an application of the present invention, apparatus, including:
a tissue anchor, having a longitudinal axis and including an engaging head, shaped to define an opening,
a tool having a longitudinal axis, and including:
a plurality of arms including at least a first arm and a second arm,
an arm actuator, configured to affect an angle of the arms with respect to the longitudinal axis of the tool by sliding along the longitudinal axis of the tool,
the apparatus having:
an articulatably-coupled state in which at least one of the arms of the tool is hooked through the opening, and the longitudinal axis of the tool is movable with respect to the longitudinal axis of the anchor, and
a rigidly-coupled state in which the arm actuator inhibits movement of the longitudinal axis of the tool with respect to the longitudinal axis of the anchor by pushing on the arms.

In an application, the engaging head is shaped to define an opening that has a first end and a second end, and is narrower at the first end than at the second end.

There is further provided, in accordance with an application of the present invention, a method for use with a tissue anchor that is implanted in a tissue of a subject, the method including:
advancing a tool toward the tissue anchor;
articulatably coupling the tool to the tissue anchor;
subsequently changing an alignment of a longitudinal axis of the tool with respect to a longitudinal axis of the tissue anchor; and subsequently rigidly coupling the tool to the tissue anchor.

There is further provided, in accordance with an application of the present invention, a tissue anchor for coupling to tissue of a subject using a tool, the tissue anchor including:
a helical tissue-coupling element:
configured to be coupled to the tissue by being screwed into the tissue, and
having a longitudinal axis; and
an eyelet:
defining a plane,
coupled to the helical tissue-coupling element such that the longitudinal axis lies on the plane, and
configured to be reversibly coupled to the tool, to accept a rotational force applied by the tool, and to transfer the rotational force to the helical tissue-coupling element.

There is further provided, in accordance with an application of the present invention, apparatus, including:
an anchor-manipulation tool including a tissue-anchor-engaging element, the tissue-anchor-engaging element including:
a plunger moveable proximally and distally along a central longitudinal axis of the tool, the plunger defining:
a distal tapered force applicator having a proximal portion that is wider than a distal portion of the force applicator, and
a proximal longitudinal element coupled to the proximal portion of the force applicator, the longitudinal element being narrower than the proximal portion of the force applicator; and
one or more engaging structures disposed adjacently to the plunger, each of the one or more engaging structures including:
a curved arm having an inner surface which defines a proximal portion which curves toward the longitudinal axis, and a central hook portion which curves away from the longitudinal axis, and
a distal hook that is a moveable in response to movement of the curved arm,
during a first period, the plunger is disposable in a proximal position in which the proximal portion of the force applicator pushes against the proximal portion of the curved arm in a manner in which the distal hook is maintained in a closed state,
during a second period, the plunger is slidable distally to a distal position in which the proximal portion of the force applicator is disposed adjacently to the central hook portion of the curved arm and the proximal portion of the curved arm inclines toward the longitudinal element in a manner in which the distal hook is moved away from the longitudinal axis by the curved arm to an opened state.

In an application, the apparatus further includes a tissue anchor including an engaging head having a wall shaped so as to define an opening shaped so as to define a funnel having a wide proximal end and a narrow distal end, and:
the engaging head is shaped to define an undercut at the narrow distal end, and
the engaging head is shaped so as to define one or more recesses at the narrow distal end in a vicinity of the undercut.

There is further provided, in accordance with an application of the present invention, a method, including:
providing an anchor-manipulation tool including:
a plunger including (1) a distal tapered force applicator having a proximal portion that is wider than a distal portion of the force applicator, and (2) a proximal longitudinal element coupled to the proximal portion of the force applicator, the longitudinal element being narrower than the proximal portion of the force applicator, and
one or more engaging structures disposed adjacently to the plunger, each of the one or more engaging structures including:
a curved arm having an inner surface which defines a proximal portion which curves toward the longitudinal axis, and a central hook portion which curves away from the longitudinal axis, and
a distal hook that is moveable in response to movement of the curved arm,
and, during the providing, the hook is in a closed state in which the plunger is disposed in a proximal position in which the proximal portion of the force applicator pushes against the proximal portion of the curved arm; and
moving the distal hook away from the longitudinal axis by the curved arm to an opened state by pushing the plunger distally to a distal position in which the proximal portion of the force applicator is disposed adjacently to the central hook portion of the curved arm and the proximal portion of the curved arm inclines toward the longitudinal element.

There is further provided, in accordance with an application of the present invention, apparatus, including:
a tissue anchor including an engaging head having a wall shaped so as to define an opening shaped so as to define a funnel having a wide proximal end and a narrow distal end, the engaging head being shaped to define an undercut at the narrow distal end, the wall of the engaging head being shaped so as to define one or more grooves at the narrow distal end proximal to the undercut;
an anchor manipulating tool having a tissue-anchor-engaging element configured to engage the wall of the engaging head, the tool having one or more engaging structures, each of the one or more engaging structures including:
a curved arm having an inner surface which defines a proximal portion which curves toward the longitudinal axis, and a central hook portion which curves away from the longitudinal axis, and
a distal hook that is moveable in response to movement of the curved arm; and
an annular element coupled to the distal end of the tool configured to facilitate positioning of the tissue-anchor-engaging element with respect to the wall of the engaging head.

The present invention will be more fully understood from the following detailed description of applications thereof, taken together with the drawings, in which:

BRIEF DESCRIPTION OF THE DRAWINGS

FIGS. 1A-B, 2A-B, and 3A-C are schematic illustrations of a tissue anchor and a tool for use with the tissue anchor, in accordance with some applications of the invention;

FIGS. 4A-E, 5A-B, and 6A-E are schematic illustrations of a system comprising the tissue anchor and the tool, and of use of the tool to retrieve the anchor from tissue of a subject, in accordance with some applications of the invention;

FIGS. 9A-C are schematic illustrations of a procedure for implanting an annuloplasty ring structure to repair a mitral valve, in accordance with an application of the present invention;

FIGS. 10A-B are schematic illustrations of the tool being used to retrieve an anchor from within a lumen of an implant, in accordance with some applications of the invention;

FIGS. 11A-E are schematic illustrations of another tool and techniques for use with a tissue anchor, in accordance with some applications of the invention;

FIGS. 12A-E are schematic illustrations of another tool and techniques for use with a tissue anchor, in accordance with some applications of the invention;

FIGS. 14 and 15A-C are schematic illustrations of a system for engaging an already-implanted anchor and facilitating extraction (e.g., retrieval) of the anchor from tissue, in accordance with some applications of the invention;

FIGS. 16, 17, 18A-C, and 19 are schematic illustrations of a system for engaging an already-implanted anchor and facilitating extraction (e.g., retrieval) of the anchor from tissue, in accordance with some applications of the invention;

FIGS. 21A-C are schematic illustrations of a tool for use with a tissue anchor, in accordance with some applications of the invention.

DETAILED DESCRIPTION OF EMBODIMENTS

Figure 7:
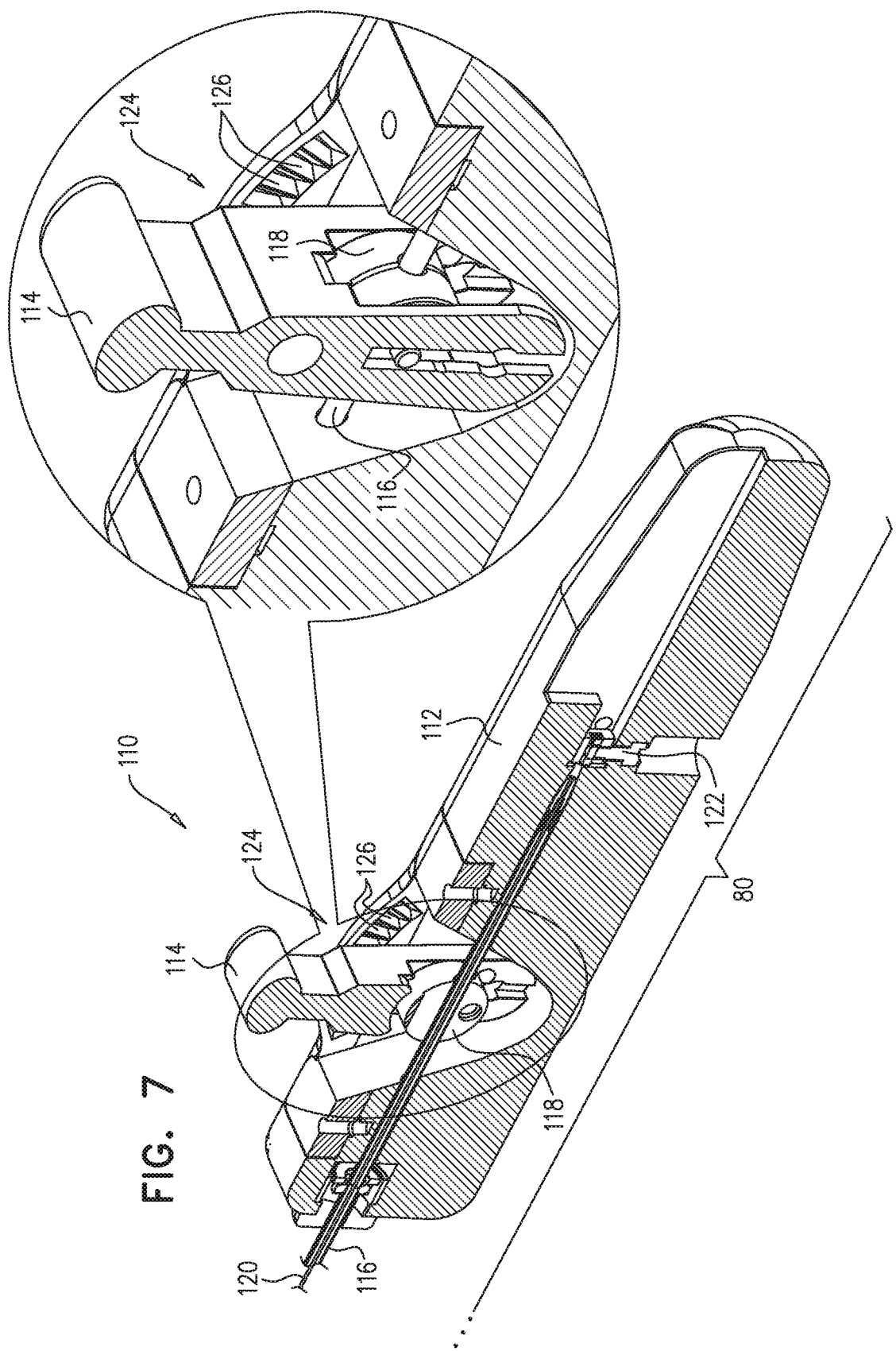
FIG. 7 is a schematic illustration of a proximal portion of the tool, including an extracorporeal controller, in accordance with some applications of the invention.

Reference is made to FIGS. 1A-3C, which are schematic illustrations of a tissue anchor 40 and a tool 80 for use with the tissue anchor, in accordance with some applications of the invention. Anchor 40 is shown in two rotational views in FIGS. 1A-B, respectively. Anchor 40 comprises a tissue-coupling element 42, and an engaging head comprising a coupling eyelet 46 defined by a bar (e.g., a shaft) 44. Typically, tissue-coupling element 42 comprises a helical tissue-coupling element, configured to be screwed into, and optionally screwed out of, tissue of a subject. Eyelet 46 provides a coupling interface for tool 80 and/or another tool. As described hereinbelow, tool 80 is typically configured, and used, to retrieve anchor 40 from tissue of the subject (e.g., after the anchor has been previously implanted and/or used to facilitate implantation of an implant). For some applications, tool 80 is also configured and/or used to implant anchor 40. For some applications, a different tool is used to implant anchor 40.

Anchor 40 has a central longitudinal axis a1, from a distal end of tissue-coupling element 42 to a proximal end of eyelet 46. Typically, a central helix axis of helical tissue-coupling element 42 is coaxial with axis a1. Eyelet 46 typically defines a plane a4 (see also FIG. 6A), on which the central helix axis and/or axis a1 typically lie. Typically, a height d1 of eyelet 46 is at least 80 percent as great as a width d2 of the eyelet (e.g., approximately equal to width d2, or greater than width d2, such as at least 50 percent greater than width d2). Typically, bar 44 defines an arch portion of eyelet 46, and anchor 40 (e.g., the engaging head thereof) comprises a base 48 that defines a base portion of the eyelet, and couples the eyelet to tissue-coupling element 42. The arch portion of the eyelet is thereby oriented such that a crest 43 of the arch portion is further from tissue-coupling element 42 than is a base 45 of the arch portion. The shape (e.g., curvature) of the arch is typically such that the arch continues to widen for most, if not all, of its length from crest 43 to base 45. Typically, any portion of bar 44 that is parallel to longitudinal axis a1 has a height along the longitudinal axis that is less than 50 percent (e.g., less than 20 percent, such as less than 10 percent) of height d1 of the eyelet. Such portions may be considered 'imposts' of the arch portion that are less than 50 percent (e.g., less than 20 percent, such as less than 10 percent) of the overall height of the arch portion. For some applications, the arch portion of the eyelet has a generally parabolic shape. Bar 44 has a thickness (e.g., a bore) d3.

FIGS. 2A-B show side and distal-end views, respectively, of a distal portion of tool 80. Tool 80 comprises a housing 82 that has an inner surface 84 that defines a generally cylindrical compartment 86 that has a transverse width (e.g., a diameter) d4. An opening 88 at a distal end 83 of the housing provides fluid communication between compartment 86 and the outside of the housing. Two or more protrusions 90 protrude radially inward from inner surface 84 into compartment 86, such that a distance d5 across the compartment between the protrusions is smaller than width d4 of the compartment, and also smaller than width d2 of eyelet 46 of anchor 40. Width d4 of compartment 86 is typically slightly greater than width d2 of eyelet 46, so as to accommodate the eyelet without allowing enough space for the eyelet to move significantly within the compartment. For example, width d4 may be at least 5 percent, less than 30 percent, and/or between 5 and 30 percent greater (e.g., 10-20 percent greater) than width d2.

Tool 80 further comprises an anchor-engaging element 91 comprising one or more (e.g., two) arms 92, each arm defining a proximal stem portion 93 and distal portion 94 (e.g., a distal hook portion), and the arms typically curving inwardly toward each other so as to define a space 96 therebetween (e.g., between respective proximal stem portions). That is, the curve of each arm defines a concavity 103, and the concavity of each arm faces the concavity of the other arm, so as to define at least part of space 96. Alternatively, stem portion 93 may be generally straight. It is to be noted, that even for applications in which stem portion 93 is generally straight, arm 92 would typically still define a concavity at a site 104 where portion 93 meets distal portion 94.

FIGS. 2A-B (and FIG. 3A) show arms in an extended position thereof, in which at least the distal portion of each arm protrudes out of opening 88 and is disposed outside compartment 86, and a gap between the distal portions has a width d6 that is great enough for at least part of bar 44 to move through, into space 96.

Typically, width d6 is greater than thickness d3 of bar 44 of eyelet 46 of anchor 40 (e.g., at least 5 times as great as thickness d3, such as at least 10 times as great as thickness d3, such as at least 20 times as great as thickness d3). Width d6 is further typically greater than width d4 of compartment 86, e.g., at least 1.5 times as great, less than 4 times as great, and/or between 1.5 times and 4 times as great. Arms 92 (e.g., portion 93 and/or portion 94 thereof) have a thickness d7 that is typically less than 0.5 times as great (e.g., less than 0.2 times as great, such as less than 0.1 times as great) as width d6, and/or less than width d4 (e.g., less than 0.5 times as great as width d4, such as less than 0.2 times as great as width d4).

For some applications, a plane a5 on which arms 92 lie is typically disposed at least 20 degrees, up to 90 degrees, and/or between 20 and 90 degrees with respect to a transverse axis a3 between protrusions 90. For example, and as shown in FIG. 2B, plane a5 may be disposed at about 45 degrees with respect to axis a3. This orientation is discussed hereinbelow with respect to FIGS. 6A-E.

In the extended position, stem portion 93 of each arm 92 typically protrudes distally away from housing 82 and outward from a longitudinal axis a2 of tool 80, and distal portion 94 of each arm protrudes from a distal end of the stem portion and inward toward the longitudinal axis. Further typically, distal portion 94 of each arm protrudes from the distal end of stem portion 93 distally away from the housing. Distal portion 94 (e.g., an inner surface thereof) is disposed at an angle alpha_A with respect to longitudinal axis a2, angle alpha_A typically being greater than 40 degrees, less than 85 degrees, and/or between 40 and 85 degrees (e.g., between 50 and 80 degrees, such as between 50 and 70 degrees and/or between 70 and 80 degrees). Due at least in part to these geometries, arms 92 typically do not define effective hooks while in the extended position. It is hypothesized that such a configuration reduces a likelihood of arms 92 inadvertently hooking to tissue or apparatus within the body of the subject.

Arms 92 further have a retracted position in which at least part of distal portion 94 of each arm is typically disposed inside compartment 86, as shown in FIG. 3C. In the retracted position, arms 92 define a loop (e.g., distal portions 94 are in contact with each other), thereby shaping space 96 to define an aperture 97.

FIGS. 3A-C show stages in the transition of arms 92 from the extended position (FIG. 3A) to the retracted position (FIG. 3C). FIG. 3B shows an intermediate position of arms 92 that is partway between the extended position and the retracted position, illustrating that as the arms move from the extended position to the retracted position, the arms form the loop before assuming the retracted position (e.g., before arms 92 completely enter compartment 86).

As arms 92 move from the extended position toward the retracted position, the arms deflect toward each other such that distal portions 94 become closer to each other (e.g., such that a distance between the distal portions is smaller than thickness d3 of bar 44. Typically, distal portions 94 are at least 10 times further (e.g., at least 20 times further) from each other when in the extended position than when in the retracted position. Further typically, in at least the retracted position (and still further typically also in the intermediate position), the distal portion of one arm is in contact with the distal portion of another (e.g., the other) arm. For some applications, each distal portion is shaped to define a beveled edge, so as to facilitate contact (e.g., mating) of the distal portions. For example, when the arms move into the intermediate position and/or the retracted position, at least part of the beveled edge of one arm moves past at least part of the beveled edge of the other arm. The beveled edges and the resulting mating is shown most clearly in FIG. 3B.

As arms 92 move toward the intermediate position and/or the retracted position, the angle at which distal portion 94 is disposed with respect to longitudinal axis a2 approaches, and typically passes, 90 degrees, such that each arm forms a hook (e.g., as shown in FIGS. 3B-C). Typically, this angle at least reaches 90 degrees before distal portions 94 contact each other. It is hypothesized that such a configuration facilitates preliminary coupling (e.g., hooking) of a single arm 92 to eyelet 46 before the arms reach the intermediate and/or retracted position. This may be advantageous, for example, when coupling tool 80 to a tissue anchor that is not disposed close to longitudinal axis a2 of tool 80.

Tool 80 further comprises an extracorporeal controller 110, which comprises a handle 112 and an adjuster 114, such as a switch or a lever. Adjuster 114 is configured to move arms 92 between the extended and retracted states. As described with reference to FIGS. 4A-E, arms 92 are typically moved between the extended and retracted states by moving housing 82 distally while the arms remain stationary (e.g., with respect to anchor 40 and/or tissue of the subject). Such a configuration facilitates coupling of arms 92 to eyelet 46 of the anchor with a reduced likelihood of the arms inadvertently moving away from the eyelet. As described in more detail hereinbelow with reference to FIG. 7, typically (1) adjuster 114 is coupled to housing 82 and is configured to reversibly move the housing further and closer from handle 112, and (2) handle 112 is coupled to arms 92 such that a distance along tool 80 between the handle and the housing is fixed.

As shown in FIGS. 3A-C, adjuster 114 is moved so as to move arms 92 between the extended position and the retracted position (e.g., via the intermediate position). Typically, and as described in more detail with reference to FIG. 7, a tactile and/or visual indicator indicates at least a state of adjuster 114 in which arms 92 are in the intermediate position (as shown in FIG. 3B). Further typically, controller 110 is configured to partially hold adjuster 114 in one or more states, such as in the state in which arms 92 are in the intermediate position.

Reference is made to FIGS. 4A-E, 5A-B, and 6A-E, which are schematic illustrations of a system 100, comprising tissue anchor 40 and tool 80, and of use of the tool to retrieve the anchor from tissue 10 of the subject, in accordance with some applications of the invention. FIG. 4A shows anchor 40 having been previously implanted in tissue 10 (e.g., to facilitate implantation of an implant; not shown in FIG. 4A, but a non-limiting illustrative example is described with reference to FIGS. 9A-10). Tool 80 is advanced toward anchor 40 with arms 92 in the extended position, such that arms 92 pass around bar 44 of eyelet 46 (i.e., such that the bar passes through the gap between the distal portions of the arms and into the space between the arms). Housing 82 is moved distally over at least part of arms 92 (e.g., such that the housing presses on a housing-contacting surface 105 of the arms), such that the arms move into the intermediate position, trapping bar 44 within aperture 97 defined by the loop formed by the arms (FIG. 4B). That is, aperture 97 acts as or defines an eyelet-retention area. It is to be noted that in this state (1) arms 92 are articulatably coupled to eyelet 46, (2) the arms (e.g., the loop defined thereby) and eyelet 46 generally resemble links in a chain (e.g., this state is an articulatably-coupled state), and (3) eyelet 46 inhibits movement of tool 80 (e.g., anchor-engaging element 91 thereof) away from tissue anchor 40.

Typically, aperture 97 (1) defines an area that is at least 10 times greater (e.g., at least 20 times greater, such as at least 40 times greater) than that of a transverse cross-sectional area of bar 44 of anchor 40, (2) has a width d8 (see FIG. 3B; e.g., a smallest width and/or a width transverse to longitudinal axis a2) that is at least 3 times greater (e.g., at least 5 times greater, such as at least 8 times greater) than thickness d3 of bar 44, and/or (3) has a width d8 that is greater (e.g., at least 2 times greater e.g., at least 4 times greater, such as at least 10 times greater) than a depth of the aperture, which is defined by thickness d7 of arms 92. That is, aperture 97 is typically (1) wider than bar 44 (e.g., at least 3 times wider, e.g., at least 5 times wider, such as at least 8 times wider), and/or (2) wider than itself is deep (e.g., at least 2 times wider, e.g., at least 4 times wider, such as at least 10 times greater). These relative dimensions of aperture 97 and bar 44 facilitate the articulatable coupling of tool 80 to eyelet 46, and/or coupling of tool 80 to the eyelet at a wide range of possible angles of attack, e.g., as described hereinbelow.

For some applications, tool 80 (e.g., anchor-engaging element 91 thereof) comprises only one arm, and bar 44 is trapped by the one arm, e.g., by being hooked by the one arm, and/or by being trapped between the one arm and inner surface 84 of compartment 86. For some applications, tool 80 comprises two arms, but only one of the arms defines a concavity. For example, the other one of the arms may be straight, and the space between the arms is shaped to define an asymmetric aperture when distal portion 94 of the arm that defines the concavity comes into contact with a distal portion of the straight arm (e.g., as described with reference to FIG. 21, mutatis mutandis).

It is to be further noted that tool 80 is shown having been advanced toward, and coupled to eyelet 46 with a longitudinal axis a2 of the tool (e.g., of housing 82) at a nonzero angle of attack with respect to longitudinal axis a1 of anchor 40. FIG. 5A more clearly shows that tool 80 is configured to engage (e.g., to be coupled to) eyelet 46 at a variety of angles of attack, including deflection in a plane defined by longitudinal axis a1 of the tissue anchor, and around axis a1. For example, tool 80 may be coupled to eyelet 46 while axis a2 is generally parallel to tissue 10, perpendicular to the tissue, or at any angle of attack therebetween. That is, tool 80 is configured to engage the coupling eyelet at at least 180 degrees of deflection of longitudinal axis a2 with respect to longitudinal axis a1 (e.g., in a plane on which axis a1 lies). Similarly, tool 80 may be coupled to eyelet 46 at at least most (e.g., all) rotational angles of attack around longitudinal axis a1, e.g., at at least 300 degrees of deflection of axis a2 around axis a1. For some applications of the invention, this means that when tool 80 is advanced from a given direction (e.g., due to anatomical and/or other constraints), the tool is couplable to eyelet 46 at at least most (e.g., all) rotational angles of attack of anchor 40 around its longitudinal axis.

The above possible angles of attack of tool 80 may also be translated into three-dimensional terms. For example, the possible angles of attack of tool 80 typically, together, define a three-dimensional angular span of at least 1 steradian (e.g., at least 3 steradians, such as at least 7 steradians) around eyelet 46. Such a span is illustrated schematically, by way of example, as span 102 in FIG. 5B.

While system 100 is in the articulatably-coupled state (e.g., while tool 80 is articulatably coupled to anchor 40), tool 80 is deflectable with respect to anchor 40. Typically, in this state, tool 80 is deflectable into any of the angles described hereinabove as angles of attack. For example, tool 80 is typically deflectable into any angle that lies within the three-dimensional angular span(s) that are described with reference to FIGS. 5A-B, such as span 102 (e.g., a three-dimensional angular span that is at least 1 steradian, such as at least 3 steradians, such as at least 7 steradians).

For some applications, such as when an angle between axes a1 and a2 is relatively large, tool 80 is subsequently manipulated so as to reduce the angle between axes a1 and a2, e.g., to at least in part align the tool and anchor 40 (FIG. 4C). For example, tool 80 may be rotated, pulled slightly proximally (e.g., along axis a2) and/or moved orthogonally with respect to axis a2. Typically, tissue 10 is sufficiently soft and/or flexible that the tissue responsively deforms (e.g., temporarily), allowing anchor 40 to move into a position in which axes a1 and a2 are more closely aligned.

Subsequently, arms 92 are moved into the retracted position, typically by housing 82 being slid over the arms (e.g., while arms 92 remain stationary), and thereby also over at least part of (e.g., most of, or all of) eyelet 46 (FIG. 4D). Housing 82 thereby typically functions as an arm actuator. By moving arms 92 into the retracted position, at least part of eyelet 46 moves into the compartment of housing 82. Although the retracted position is described hereinabove as having at least part of distal portion 94 of each arm typically disposed inside compartment 86, as shown in FIG. 3C, it is to be noted that for some applications, distal portions do not enter compartment 86. For example, in the retracted position, distal portions 94 may remain just outside of compartment 86, e.g., sufficiently close to the compartment that at least part of eyelet 46 moves into the compartment when the arms move into the retracted position.

Housing 82 is configured to receive eyelet 46 at a plurality of rotational positions (e.g., a continuum of rotational positions) with respect to the housing. Portions of bar 44 of eyelet 46 become disposed in a circumferential space between protrusions 90. For example, and as shown in FIG. 6A, which is a cross-sectional view of system 100 with eyelet 46 disposed within compartment 86 of housing 82 (as indicated by section "VIA-VIB" in FIG. 4D), transverse axis a3 between protrusions 90 of the housing may be disposed at a continuum of rotational positions with respect to plane a4 defined by eyelet 46. Typically, this continuum of rotational positions spans at least 90 degrees (e.g., at least 150 degrees, such as almost 180 degrees) around axis a2. For some applications, housing 82 is configured to receive eyelet 46 at one or more continua of rotational positions of plane a4, that span a total of at least 270 degrees around longitudinal axis a2. FIG. 6A schematically shows rotational positions in which eyelet 46 may be disposed, by way of "phantom" portions of bar 44.

Although as described in the above paragraph housing 82 is configured to receive eyelet 46 at a plurality (e.g., a continuum) of rotational positions with respect to the housing, the orientation of arms 92 (e.g., plane a5 thereof) with respect to protrusions 90 (e.g., axis a3 therebetween) may bias the eyelet (e.g., plane a4 thereof) to be oriented in a particular rotational position with respect to the housing. For example, and as shown in FIG. 6A, the arrangement of protrusions may bias plane a4 toward an angular span 99 that is generally centered orthogonally to axis a5. FIG. 6A schematically shows a rotational position of the eyelet (e.g., into which the eyelet is biased) by way of shaded portions of bar 44, disposed generally central within angular span 99. It is hypothesized that such biasing may inhibit axis a4 from aligning with axis a3 (which might otherwise inhibit entry of eyelet 46 into compartment 86 of housing 82). It is further hypothesized that such biasing may advantageously align protrusions 90 and eyelet 46 in advance of rotation of anchor 40 (which is described hereinbelow with reference to FIGS. 4E and 6A-E). FIG. 6B shows, for clarity, the same arrangement of elements as FIG. 6A, but without the "phantom" portions of bar 44, and with less annotation.

As described hereinabove, in the intermediate position, arms 92 are articulatably coupled to eyelet 46. The compartment of housing 82 is typically dimensioned such that the eyelet fits generally snugly therewithin. Thereby movement of eyelet 46 into the compartment of housing 82 typically inhibits articulation of the eyelet with respect to the arms. The state of system 100 shown in FIG. 4D (and FIG. 4E) may thereby, for some applications, be a rigidly-coupled state. Typically, the dimensions and/or shape of eyelet 46 (e.g., of bar 44 thereof), such as those described with reference to FIGS. 1A-B, facilitate entry of the eyelet into the compartment of housing 82, such as by facilitating alignment of anchor 40 with tool 80. For example, curvature of the arch portion of eyelet 46 may facilitate alignment of axes a1 and a2 as the eyelet is moved into the compartment of housing 82.

Subsequently, as shown in FIG. 4E, and as shown in cross section in FIGS. 6C-E, housing 82 is rotated so as to rotate, and thereby unscrew, anchor 40 from tissue 10. Initially, rotation of housing 82 moves protrusions 90 until they engage (e.g., contact and press against) bar 44 of eyelet 46 (FIGS. 6C-D). Further rotation of housing 82 applies a de-anchoring rotational force to eyelet 46, thereby rotating the eyelet and anchor 40 as a whole, and thereby unscrewing the anchor from tissue 10 (FIG. 6E). It is to be noted that, (1) whereas a proximal/pulling force is applied to anchor 40 by a first element of tool 80 (i.e., anchor-engaging element 91, e.g., arms 92 thereof), a rotational/torque force is applied by a second element of the tool (i.e., housing 82, e.g., protrusions 90 thereof). That is, pulling and rotation of anchor 40 are conducted by two distinct elements of tool 80 that are movable (e.g., longitudinally slidable) with respect to each other. It is to be further noted that rotating housing 82 in the reverse direction may screw anchor 40 into tissue 10. For some applications, tool 80 may be used to re-anchor anchor 40 into tissue 10, or may even be used for the initial anchoring of the anchor.

Figure 9A:
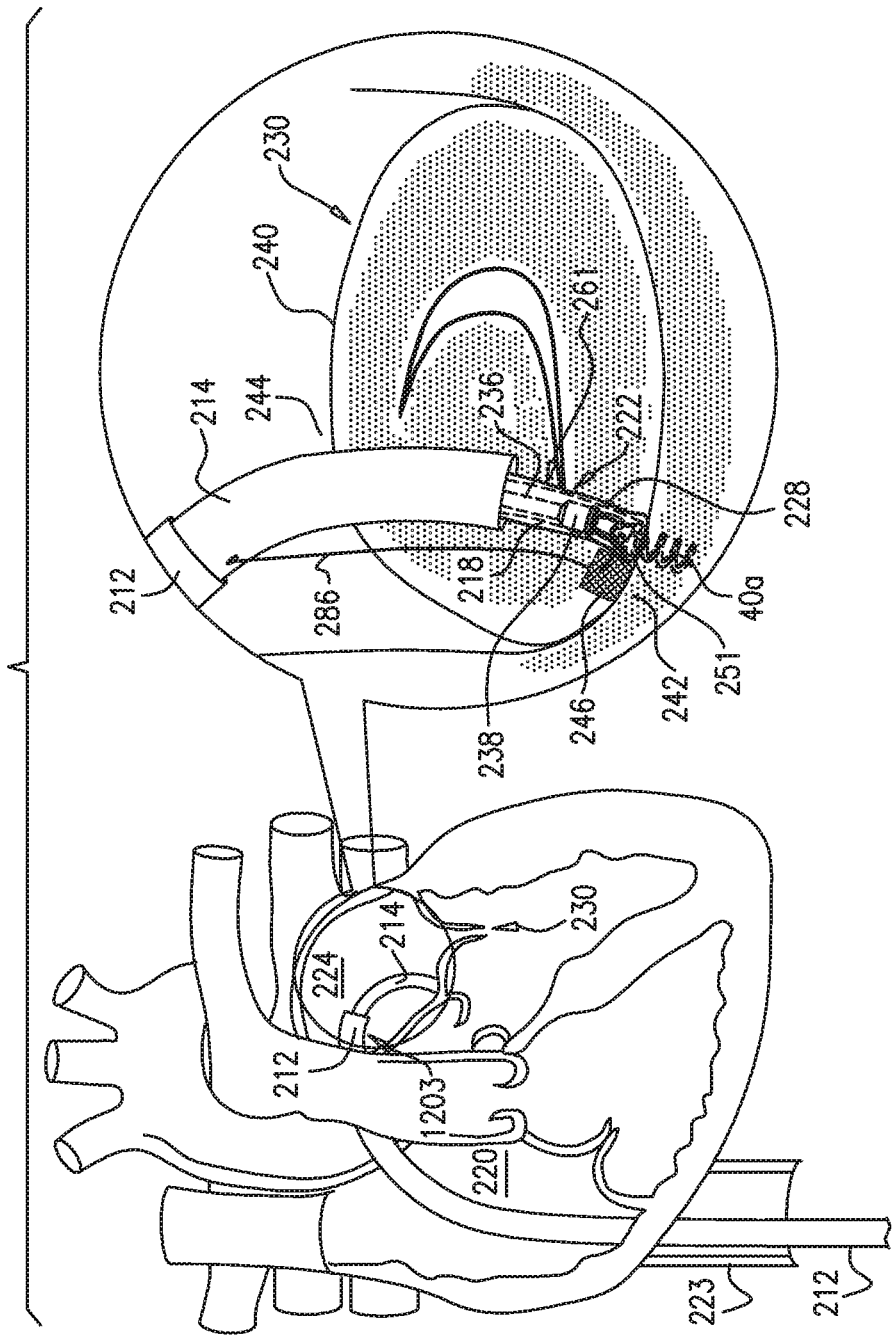

It is to be noted that, although FIGS. 4A-5B show anchor 40 anchored alone to tissue 10, anchor 40 is typically used to anchor another element, such as an implant, to the tissue. For example, and as shown in FIGS. 9A-10 mutatis mutandis, tissue-coupling element 42 may pierce a portion of an implant and penetrate tissue 10, such that base 48 sandwiches the portion of the implant to the tissue.

Reference is made to FIG. 7, which is a schematic illustration of a proximal portion of tool 80, including extracorporeal controller 110, which comprises handle 112 and adjuster 114, in accordance with some applications of the invention. As described briefly hereinabove with reference to FIGS. 3A-C, typically (1) adjuster 114 is coupled to housing 82 and is configured to reversibly move the housing further and closer from handle 112, and (2) handle 112 is coupled to arms 92 such that a distance along tool 80 between the handle and the housing is fixed. For some applications, adjuster 114 is coupled to a tubular longitudinal member 116 (e.g., via a cam 118), the tubular longitudinal member being slidable with respect to handle 112, and a distal end of the tubular longitudinal member being coupled to housing 82. For some applications, the distal portion of tubular longitudinal member 116 comprises and/ or defines housing 82. For such applications, handle 112 is typically coupled (e.g., fixedly coupled) to a longitudinal member 120 (e.g., via a fastener 122, such as a set screw), a distal end of the longitudinal member being coupled (e.g., fixedly coupled) to arms 92, and tubular longitudinal member 116 is slidable over the longitudinal member. Typically, longitudinal member 120 is disposed through tubular longitudinal member 116. Typically, and as shown in FIG. 7, handle 112 is coupled to a proximal end of longitudinal member 120 that is exposed from a proximal end of tubular longitudinal member 116.

Tool 80 is typically used to retrieve anchor 40 percutaneously (e.g., transluminally). Housing 82, tubular longitudinal member 116 and longitudinal member 120 are thereby configured to be percutaneously advanced to a site at which anchor 40 is implanted. For example, when tool 80 is configured to transluminally retrieve anchor 40, housing 82, tubular longitudinal member 116 and longitudinal member 120 are dimensioned to fit within the blood vessel(s) through which they are to be advanced, and the tubular longitudinal member and the longitudinal member are sufficiently flexible to follow the transluminal route.

Typically, extracorporeal controller 110 comprises and/or defines an indicator 124 that indicates a state of adjuster 114, and thereby the position of arms 92. Indicator 124 may comprise a visual indicator, such as markings, and/or may comprise a tactile indicator, such as graduated ridges 126 with which a part of adjuster 114 interfaces. Indicator 124 typically indicates at least a state of adjuster 114 in which arms 92 are in the intermediate position in which they define the loop but are not in the retracted position. Indicator 124 may also indicate one or more states of adjuster 114 in which arms 92 are between the extended position and the intermediate position (e.g., partially closed), e.g., so as to facilitate advancement of tool 80 through a narrow lumen. Indicator 124 (e.g., ridges 126 thereof) may be configured to partially hold adjuster 114 in one or more states, such as in the state in which arms 92 are in the intermediate position.

Reference is again made to FIGS. 4A-E, 5A-B, and 6A-E. For some applications, each arm 92 has a generally sigmoid shape, in which (1) an inwardly convex proximal portion 99 of the arm (e.g., an inwardly convex proximal portion of stem portion 93) curves away from axis a2, and (2) an inwardly concave distal portion 101 of the arm (e.g., distal portion 94, and/or an inwardly convex distal portion of stem portion 93) curves at least in part back toward axis a2, and defines concavity 103 described hereinabove. It is hypothesized that this configuration facilitates at least some of the functionalities described herein. For example:

The outward curvature of portion 99 may facilitate sliding housing 82 thereover, so as to move arms 92 into the intermediate position. That is, portion 99 may have a housing-contacting surface 105 on which housing 82 presses when the housing slides over portion 99. For example, the outward curvature of portion 99 may maintain, during movement of housing 82 over arm 92, a generally constant interface angle alpha_C between the housing and the part of the arm (e.g., the part of surface 105) that is currently in contact with the housing. It is hypothesized that this thereby maintains a constant resistance to movement of housing 82 over arm 92, thereby facilitating control by the operating physician.

The outward curvature of portion 99 and/or the inward curvature of portion 101 may facilitate the arms forming the loop and aperture 97 before assuming the retracted position (e.g., before arms 92 completely enter compartment 86).

Figure 8:
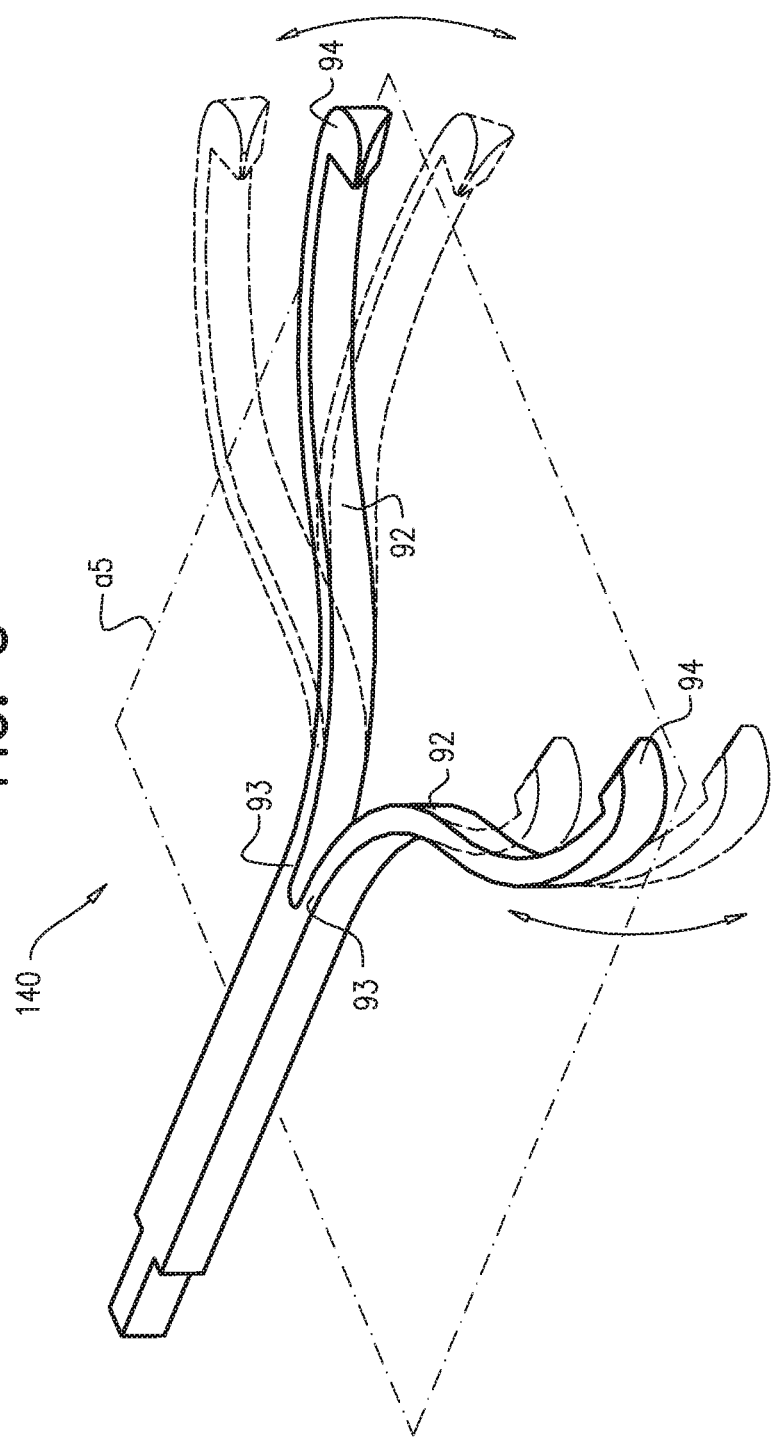
FIG. 8 is a schematic illustration of arms of the tool, in accordance with some applications of the invention.

Reference is made to FIG. 8, which is a schematic illustration of arms 92, in accordance with some applications of the invention. Typically, the proximal stem portion 93 of arms 92 are coupled to each other (e.g., fixedly coupled to each other, or articulatably coupled to each other). For some applications, and as shown in FIG. 8, a forked member 140, comprising a continuous piece of material, defines arms 92 (e.g., each tine of the forked member defining a respective arm). For some applications, arms 92 are biased toward deflecting away from each other, such as by forked member 140 comprising a resilient material. For some such applications, the resilient material allows arms 92 to progressively bend and/or deflect toward each other as the arms are progressively moved into compartment 86 of housing 82 (e.g., as the arms progressively move toward the intermediate and/or retracted position thereof).

Arms 92 are typically disposed on a plane a5 (e.g., when in a relaxed and/or unconstrained state). For some applications, arms 92 are more resistant to bending in plane a5 (i.e., in-plane) than away from plane a5 (i.e., off-plane). For some such applications, when forked member 140 defines arms 92 and comprises a resilient material, the material is more flexible off-plane than it is in-plane. FIG. 8 shows in phantom arms 92 being bent off-plane. It is hypothesized that this relatively high off-plane flexibility of arms 92 facilitates decoupling of arms 92 from an element to which they are coupled (e.g., to which they are inadvertently coupled), such as by moving (e.g., rotating) tool 80 in order to bend and thereby release the arm from the element.

Figure 9B:
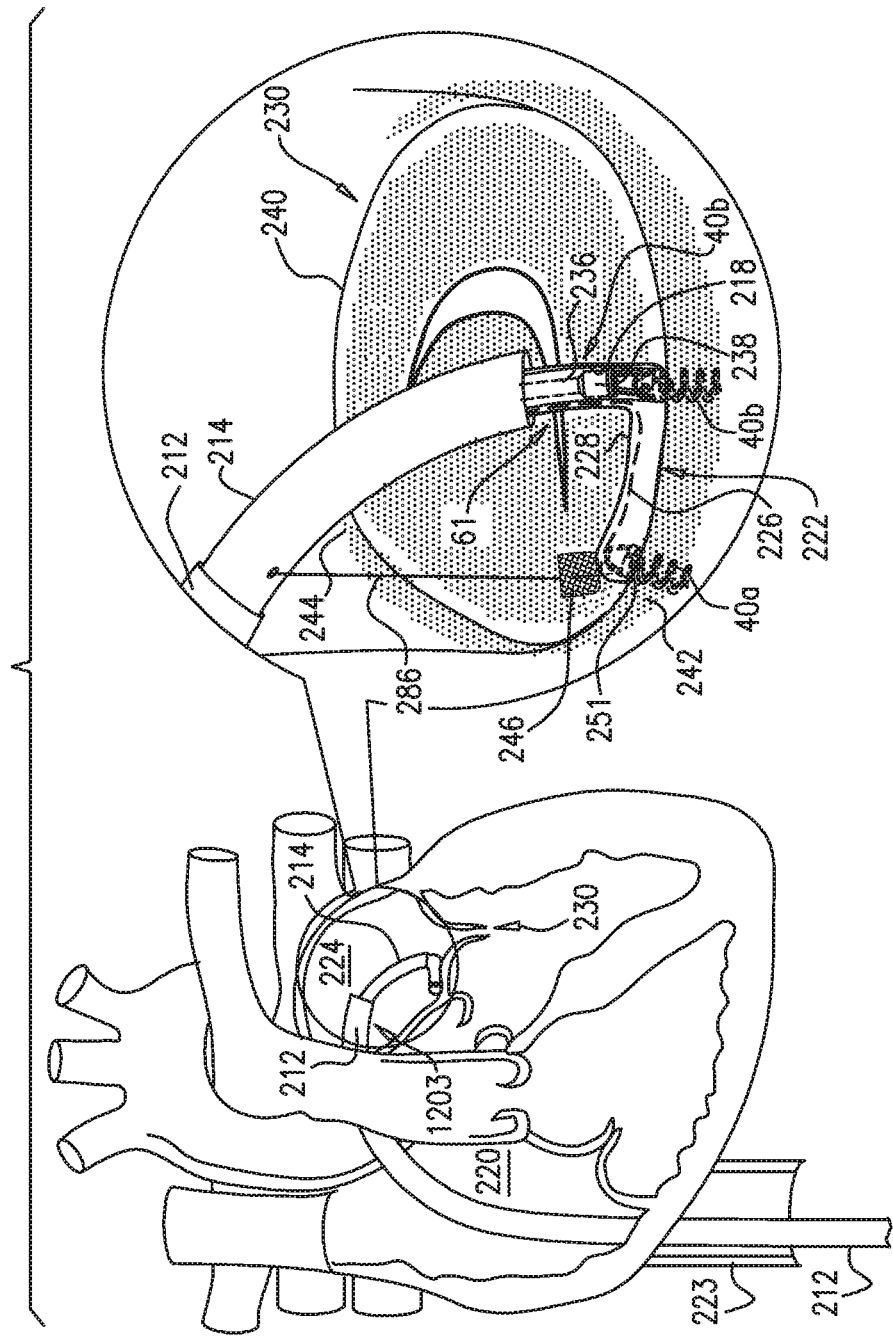

Reference is now made to FIGS. 9A-C, which are schematic illustrations of a procedure for implanting an annuloplasty ring structure 222 to repair a mitral valve 230, in accordance with an application of the present invention. Annuloplasty ring structure 222 is used to repair a dilated valve annulus of an atrioventricular valve, such as mitral valve 230. For some applications, the annuloplasty ring is configured to be placed only partially around the valve annulus (e.g., to assume a C-shape), and, once anchored in place, to be contracted so as to circumferentially tighten the valve annulus. The annuloplasty ring comprises a flexible sleeve 228 and a plurality of anchors 40. An anchor deployment manipulator 261, comprising an anchor driver 236 and a deployment element 238 at a distal end of the anchor driver, is advanced into a lumen of sleeve 228, and, from within the lumen, deploys the anchors through a wall of the sleeve and into cardiac tissue, thereby anchoring the sleeve around a portion of the valve annulus.

For some applications, annuloplasty ring structure 222 is implanted, mutatis mutandis, using techniques described in U.S. application Ser. No. 12/437,103, filed May 7, 2009 which published as US 2010/0286767, and which issued as U.S. Pat. No. 8,715,342, and/or US application Ser. No. 12/689,635, filed Jan. 19, 2010 which published as US 2010/0280604, and which issued as U.S. Pat. No. 8,545,553, both of which are assigned to the assignee of the present application and are incorporated herein by reference.

For some applications, annuloplasty ring structure 222 is implanted, mutatis mutandis, using techniques described in U.S. Provisional Application 61/717,303, which is assigned to the assignee of the present application and is incorporated herein by reference.

Annuloplasty ring structure 222 comprises an adjusting mechanism 246. The adjusting mechanism comprises a rotatable structure, such as a spool, arranged such that rotation of the rotatable structure contracts the implant structure. The implant further comprises a longitudinal member 286, such as a wire, which is coupled to the adjusting mechanism. A rotation tool (not shown) is provided for rotating the rotatable structure. The tool is configured to be guided along (e.g., over, alongside, or through) longitudinal member 286, to engage the rotatable structure, and to rotate the rotatable structure in response to a rotational force applied to the tool.

The procedure typically begins by advancing a semi-rigid guidewire into a right atrium 220 of the patient. The procedure is typically performed with the aid of imaging, such as fluoroscopy, transesophageal echo, and/or echocardiography. The guidewire provides a guide for the subsequent advancement of an outer steerable catheter 212 therealong and into the right atrium. Catheter 212 typically comprises a 14-24 F sheath, although the size may be selected as appropriate for a given patient. Catheter 212 is advanced through vasculature into the right atrium using a suitable point of origin typically determined for a given patient. For example:

catheter 212 may be introduced into the femoral vein of the patient, through an inferior vena cava 223, into right atrium 220, and into a left atrium 224 transseptally, typically through the fossa ovalis;

catheter 212 may be introduced into the basilic vein, through the subclavian vein to the superior vena cava, into right atrium 220, and into left atrium 224 transseptally, typically through the fossa ovalis; or catheter 212 may be introduced into the external jugular vein, through the subclavian vein to the superior vena cava, into right atrium 220, and into left atrium 224 transseptally, typically through the fossa ovalis.

For some applications of the present invention, catheter 212 is advanced through inferior vena cava 223 of the patient (as shown) and into right atrium 220 using a suitable point of origin typically determined for a given patient.

Catheter 212 is advanced distally until the sheath reaches the interatrial septum, and a resilient needle and a dilator (not shown) are advanced through catheter 212 and into the heart. In order to advance catheter 212 transseptally into left atrium 224, the dilator is advanced to the septum, and the needle is pushed from within the dilator and is allowed to puncture the septum to create an opening that facilitates passage of the dilator and subsequently catheter 212 therethrough and into the left atrium. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum. The advancement of catheter 212 through the septum and into the left atrium is followed by the extraction of the dilator and the needle from within catheter 212.

FIG. 9A shows the distal portion of catheter 212 disposed within atrium 224, and a second steerable catheter 214, containing annuloplasty ring structure 222 at a distal end thereof, having been advanced through catheter 212 into left atrium 224. As shown in FIG. 9A, a distal end portion of catheter 214 extends beyond the distal end of catheter 212. The distal end portion of catheter 212 is steerable in a first plane that is parallel to a plane of the annulus of mitral valve 230. The distal end portion of catheter 214 is steerable toward the annulus of valve 230 along a plane that is perpendicular with respect to the steering plane of catheter 212 and that is perpendicular with respect to valve 230. The juxtaposition of the two steering planes, along with the ability to slide catheter 214 distally and proximally through catheter 212, allows structure 222, and portions thereof, to be placed at any site on the annulus of valve 230.

As shown in FIG. 9A, a distal end 251 of sleeve 228 is positioned against an annulus 240 of mitral valve 230, e.g., in a vicinity of a left fibrous trigone 242. (It is noted that for clarity of illustration, distal end 251 of sleeve 228 is shown schematically in the cross-sectional view of the heart, although left trigone 242 is in reality not located in the shown cross-sectional plane, but rather out of the page closer to the viewer.) Alternatively, distal end 251 is positioned in a vicinity of a right fibrous trigone 244 of the mitral valve (configuration not shown). Further alternatively, the distal end of the sleeve is not positioned in the vicinity of either of the trigones, but is instead positioned elsewhere in a vicinity of the mitral valve, such as in a vicinity of the anterior or posterior commissure. Once positioned at the desired site, deployment manipulator 261 deploys a first anchor 40a through the wall of sleeve 228. Typically, the anchor is deployed by penetrating the wall of the sleeve in a direction parallel to a central longitudinal axis of deployment manipulator 261, or anchor driver 236, and/or parallel to central longitudinal axis of the anchor, into cardiac tissue. Typically, base 48 of anchor 40 (shown in FIGS. 1A-B) secures a portion of sleeve 228 by sandwiching the portion of the sleeve against the tissue to which the anchor is anchored.

Typically, a channel 218 is provided disposed snugly within sleeve 228, and anchor driver 236 delivers anchors 40 via the channel. Channel 218 is more rigid than sleeve 228, and is progressively slid out of the sleeve as subsequent anchors 40 are delivered. Anchors 40 are typically deployed from a distal end of manipulator 261 while the distal end is positioned such that a central longitudinal axis through the distal end of manipulator 61 forms an angle with a surface of the cardiac tissue of between about 20 and 90 degrees, e.g., between 45 and 90 degrees, such as between about 75 and 90 degrees, such as about 90 degrees. Typically, anchors 40 are deployed from the distal end of manipulator 261 into the cardiac tissue in a direction parallel to the central longitudinal axis through the distal end of manipulator 261. Such an angle is typically provided and/or maintained by channel 218 being more rigid than sleeve 228. The distal end of channel 218 is typically brought close to the surface of the cardiac tissue (and the wall of sleeve 228 that is disposed against the surface of the cardiac tissue), such that little of each anchor 40 is exposed from the channel before penetrating the sleeve and the tissue. For example, the distal end of channel 218 may be placed (e.g., pushed) against the wall of the sleeve, sandwiching the sleeve against the cardiac tissue.

For some applications, this placement of the distal end of channel 218 against the cardiac tissue (via the wall of the sleeve), stabilizes the distal end during deployment and anchoring of each anchor 40, and thereby facilitates anchoring. For some applications, pushing of the distal end of channel 218 against the cardiac tissue (via the wall of the sleeve) temporarily deforms the cardiac tissue at the site of contact. This deformation may facilitate identification of the site of contact using imaging techniques (e.g., by identifying a deformation in the border between cardiac tissue and blood), and thereby may facilitate correct positioning of the anchor.

For some applications of the present invention, anchors 32 may be deployed from a lateral portion of manipulator 261.

As shown in FIG. 9B, following the deployment of the first anchor, channel 218 is slid proximally out from a distal portion of sleeve 228, typically facilitated by providing a reference pushing force to sleeve 228 using a reference-force tube (not shown). The distal end of channel 218 is repositioned along annulus 240 to another site selected for deployment of a second anchor 40b, and the anchor is deployed.

Typically, the first anchor is deployed most distally in the sleeve (generally at or within a few millimeters of the distal tip of the sleeve), and each subsequent anchor is deployed more proximally, such that the sleeve is gradually decoupled from channel 218 in a distal direction during the anchoring procedure (i e, channel 218 is withdrawn from within sleeve 228, so as to make the successive proximal portion sleeve 228 ready for implantation of a subsequent anchor). The already-deployed first anchor 40a holds the anchored end of sleeve 228 in place, so that the sleeve is drawn from the site of the first anchor towards the site of the second anchor.

As shown in FIG. 9C, deployment manipulator 261 (e.g., deployment element 238 thereof) is repositioned along the annulus to additional sites, at which respective anchors (e.g., including anchors 40c and 40d) are deployed, until the last anchor is deployed in a vicinity of right fibrous trigone 244 (or left fibrous trigone 242 if the anchoring began at the right trigone). Alternatively, the last anchor is not deployed in the vicinity of a trigone, but is instead deployed elsewhere in a vicinity of the mitral valve, such as in a vicinity of the anterior or posterior commissure. Guide member 286 is typically left behind, and an adjustment tool 287 is subsequently threaded over and advanced along the guide member toward adjusting mechanism 246 and is used to rotate the spool of the adjusting mechanism, in order to tighten structure 222 by adjusting a degree of tension of a contracting member 226 disposed therewithin.

FIGS. 9A-C show a guide member 286, coupled to adjusting mechanism 246, and extending proximally through catheter 214 (e.g., into a lateral opening of the catheter, and through a secondary lumen of the catheter). It is to be noted that, for simplicity, rotation tool 287 and deployment element 238 are shown in FIG. 9C as being simultaneously present in the heart of the subject. However, deployment element 238 may be withdrawn from the body of the subject before tool 287 is introduced. For some applications, catheter 214 is also removed, leaving guide member 286 disposed through catheter 212, such that adjustment tool 287 is advanceable through catheter 212, and along the guide member to adjusting mechanism 246.

Once the desired level of adjustment of structure 222 is achieved (e.g., by monitoring the extent of regurgitation of the valve under echocardiographic and/or fluoroscopic guidance), the rotation tool and guide member 286 are removed from the heart. For some applications, a distal portion of guide member 286 may be left within the heart of the patient and the proximal end may be accessible outside the body, e.g., using a port. For such applications, adjusting mechanism 246 may be accessed at a later stage following initial implantation and adjustment of ring structure 222.

For some applications, a re-access wire 288 may be provided, coupled to a proximal portion of the implant (e.g., a portion of the implant that is deployed last), such as to a last anchor (as shown in FIG. 9C), or to the sleeve of the implant. Should it be determined, after implantation (e.g., and after adjustment) of annuloplasty ring structure 222, that one or more anchors 40 requires retrieval, re-access wire 288 facilitates guidance of tool 80 to annuloplasty ring structure 222 and/or into the lumen thereof (described further with reference to FIGS. 10A-B, mutatis mutandis).

Alternatively, annuloplasty ring structure 222 is implanted by right or left thoracotomy, mutatis mutandis.

Reference is made to FIGS. 10A-B, which are schematic illustrations of tool 80 being used to retrieve an anchor 40 from within a lumen 164 of an implant 160, in accordance with some applications of the invention. FIGS. 10A-B show implant 160 comprising an annuloplasty ring structure 161 comprising a sleeve 162 that has been implanted by sequentially delivering a plurality of anchors 40 (e.g., at least anchors 40a, 40b, 40c, and 40d) (1) through lumen 164 defined by the sleeve, (2) through the sleeve wall and (3) into tissue 10. Anchors 40 are typically delivered via a channel 166 that is disposed within sleeve 162 and is slidable progressively out of the sleeve as each anchor is delivered and anchored. For some applications, one or more elements shown in FIG. 10 comprise respective elements of the same name described with reference to FIGS. 9A-C. For example, annuloplasty ring structure 161 may comprise annuloplasty ring structure 222, sleeve 162 may comprise sleeve 228, channel 166 may comprise channel 218, and tissue 10 may comprise annulus 240.

Should it be necessary to remove an anchor, such as anchor 40d, tool 80 may be advanced through channel 166 so as to access lumen 164, and thereby the anchor (e.g., as shown in FIG. 10A). Sleeve 162 typically facilitates this advancing by mechanically guiding (e.g., by partially constraining movement of) tool 80 and/or channel 166. Typically, while tool 80 is being operated (e.g., while arms 92 are being moved between the extended and retracted positions), the arms are exposed out from channel 166 such that the channel does not inhibit movement of the arms. For example, while tool 80 is being operated, the arms may be disposed at least 5 mm, e.g., at least 10 mm, such as at least 50 mm distal to a distal end of channel 166. Once anchor 140d has been unscrewed from tissue 10 (and sleeve 162), tool 80 is used to draw the anchor into channel 166 and out of the body of the subject. For some applications, tool 80 is advanced not via channel 166, and the channel is subsequently advanced over the tool.

For some applications, tool 80 may be guided to annuloplasty ring structure 161 and/or into lumen 164 thereof by being advanced along a re-access wire 288 (shown for structure 222 in FIG. 9C, mutatis mutandis). Re-access wire 288 is coupled to a proximal portion of the implant (e.g., a portion of the implant that is deployed last), such as to a last anchor (as shown in FIG. 9C), or to the sleeve of the implant.

For some applications, should it be necessary to remove an anchor other than the most recently-deployed anchor, tool 80 may be coupled to that anchor by being advanced past more recently-deployed anchors. For example, as shown in FIG. 10B, tool 80 may be advanced past anchors 40d and 40c, and coupled to anchor 40b. Typically, but not necessarily, channel 166 is not advanced past the more recently-deployed anchors, but rather remains proximal to the most recently-deployed anchor. Lumen 164 of sleeve 162 has a transverse cross-sectional width (e.g., diameter) d9. Typically, tool 80 is dimensioned to pass, within the lumen, past the more recently-deployed anchors. Further typically, the flexibility of sleeve 162 facilitates such passage, e.g., by deforming in response to the presence of tool 80.

For some applications, flexibility of tubular longitudinal member 116 facilitates advancement of tool 80 through lumen 164, e.g., past bends in sleeve 162. For example, tool 80 may be advanced distally, and be at least in part guided and/or passively steered by sleeve 162 (e.g., tubular longitudinal member 116 may bend to conform with the direction of the sleeve). Such steering may be supplemented by rotation of tool 80.

While arms 92 of tool 80 are in the extended position, the gap between distal portions 94 of each arm (e.g., width d6; FIG. 2A) is typically at least 20 percent as great (e.g., at least 50 percent as great, such as at least 80 percent as great) as width d9. Such relative dimensions typically facilitate engagement of eyelet 46 by the arms, e.g., by increasing the likelihood of the eyelet becoming disposed between the arms. For some applications, the features of arms 92 (1) not defining effective hooks while in the extended position (described with reference to FIG. 2A) and/or (2) being more flexible off-plane than in-plane (described with reference to FIG. 8) facilitate use of such large relative dimensions because, as described hereinabove, these features are hypothesized to (1) reduce a likelihood of the arms inadvertently hooking to an untargeted tissue or apparatus (e.g., the sleeve, or another anchor), and/or (2) facilitate release of the arms from said untargeted tissue or apparatus. As described hereinabove, for some applications, tool 80 is also configured and/or used to implant anchor 40. For some applications, tool 80 comprises and/or is analogous to deployment manipulator 261 and/or anchor driver 236 described with reference to FIGS. 9A-C (and arms 92 comprise and/are analogous to deployment element 238), mutatis mutandis.

Imaging techniques such as fluoroscopy and/or ultrasound may be used to facilitate the use of tool 80. For example, the position of arms 92 (including the rotational position) with respect to eyelet 46 may be observed using such imaging techniques, and adjusted accordingly. For some applications, fluoroscopy is used, following movement of arms 92 into the intermediate position, to identify successful coupling (e.g., articulatable coupling) of the arms to eyelet 46, such as by identifying the links-in-a-chain arrangement described hereinabove. Similarly, imaging may be used to confirm that another element, such as sleeve 162, has not been engaged by tool 80. Following identification of the links-in-a-chain arrangement, the operating physician may then move the arms into the retracted position. For some applications, radiopaque markings are provided on arms 92, eyelet 46, and/or other components of the apparatus. For example, some elements of the apparatus may comprise tantalum, gold, platinum, or another radiopaque material. For some applications, mechanical guidance, such as that provided by sleeve 162 (as described hereinabove) is used to facilitate advancing of tool 80 (e.g., a distal end thereof) to the vicinity of the anchor, and imaging is used (e.g., only) to facilitate fine manipulation of the tool in order to couple the tool to the anchor.

Throughout the present application various dimensions are mentioned, and the values thereof are typically described with respect to the values of other such dimensions. While not intending to unduly limit the scope of the invention, the following values, which have been determined to be of particular interest to the inventors, are provided:

For some applications, height d1 of eyelet 46 is greater than 1.5 mm and/or less than 7 mm, e.g., greater than 2 mm and/or less than 5 mm, such as greater than 2.3 mm and/or less than 2.6 mm (e.g., between 2.3 mm and 2.6 mm).

For some applications, width d2 of eyelet 46 is greater than 1.5 mm and/or less than 4 mm, e.g., greater than 2 mm and/or less than 3 mm, such as greater than 2.3 mm and/or less than 2.5 mm (e.g., between 2.3 mm and 2.5 mm).

For some applications, thickness d3 of bar 44 is greater than 0.15 mm and/or less than 1.5 mm, e.g., greater than 0.2 mm and/or less than 1 mm, such as greater than 0.25 mm and/or less than 0.4 mm (e.g., between 0.25 mm and 0.4 mm).

For some applications, transverse width d4 of compartment 86 is greater than 1.2 mm and/or less than 3.5 mm, e.g., greater than 1.5 mm and/or less than 2.6 mm, such as greater than 2 mm and/or less than 2.4 mm (e.g., between 2 mm and 2.4 mm).

For some applications, distance d5 between protrusions 90 is greater than 0.8 mm and/or less than 3 mm, e.g., greater than 1 mm and/or less than 2.2 mm, such as greater than 1.5 mm and/or less than 2 mm (e.g., between 1.5 mm and 2 mm).

For some applications, width d6 of the gap between distal portions 94 of arms 92 is greater than 2 mm and/or less than 9 mm, e.g., greater than 3 mm and/or less than 8 mm, such as greater than 5 mm and/or less than 7 mm (e.g., between 5 mm and 7 mm).

For some applications, thickness d7 of arms 92 is greater than 0.15 mm and/or less than 1.2 mm, e.g., greater than 0.2 mm and/or less than 0.8 mm, such as greater than 0.3 mm and/or less than 0.5 mm (e.g., between 0.3 mm and 0.5 mm).

For some applications, width d8 of the area defined by aperture 97 is greater than 1 mm and/or less than 3.5 mm, e.g., greater than 1.5 mm and/or less than 2.6 mm, such as greater than 2 mm and/or less than 2.4 mm (e.g., between 2 mm and 2.4 mm).

For some applications, width d9 of lumen 164 of sleeve 162 is greater than 1.8 mm and/or less than 9 mm, e.g., greater than 2.1 mm and/or less than 6 mm, such as greater than 2.5 mm and/or less than 4 mm (e.g., between 2.5 mm and 4 mm).

Reference is made to FIGS. 11A-E, which are schematic illustrations of a tool 380 and techniques for use with a tissue anchor such as tissue anchor 40, in accordance with some applications of the invention. Similarly to tool 80, tool 380 is also typically configured, and used, to retrieve anchor 40 from tissue of the subject (e.g., after the anchor has been previously implanted and/or used to facilitate implantation of an implant). Also similarly to tool 80, may alternatively or additionally be configured and/or used to implant anchor 40.

Tool 380 comprises a housing 382 that has an inner surface 384 that defines a generally cylindrical compartment 386 that has a transverse width (e.g., a diameter), as shown in FIG. 2B as width d4 of compartment 86, mutatis mutandis. An opening 388 at a distal end of the housing provides fluid communication between compartment 386 and the outside of the housing. For some applications, one or more protrusions 390 (seen in FIG. 11C) protrude radially inward from inner surface 384 into compartment 386. A distance across the compartment between the protrusions (as shown in FIG. 2B as width d5 of compartment 86, mutatis mutandis) is smaller than the transverse width of the compartment, and also smaller than width d2 of eyelet 46 of anchor 40. The transverse width of compartment 386 is typically slightly greater than width d2 of eyelet 46, so as to accommodate the eyelet without allowing enough space for the eyelet to move significantly within the compartment. For example, the transverse width may be at least 5 percent, less than 30 percent, and/or between 5 and 30 percent greater (e.g., 10-20 percent greater) than width d2. Housing 382 is typically similar to, and for some applications is identical to, housing 82, described hereinabove with reference to FIGS. 1A-10.

Tool 380 further comprises an anchor-engaging element 391 comprising at least one curved arm 392. Typically, arm 392 is shaped to define a distal hook portion 394 which, for some applications is helical. Arm 392 is rotatable, independently of housing 382, around a longitudinal axis a6 of the housing (or of tool 380) by rotating a longitudinal member 383 that extends from the arm out of the body of the subject. Arm 392 is also slidable, independently of housing 382, along axis a6 such that the arm (e.g., hook portion 394 thereof) is slidable into and out of the housing.

FIG. 11A shows arm 392 in an extended position thereof, in which at least hook portion 394 thereof protrudes out of opening 388 and is disposed outside compartment 386. Arm 392 further has a retracted position in which at least part of hook portion 394 is typically disposed inside compartment 386, as shown in FIG. 11C.

Tool 380 further comprises an extracorporeal controller (not shown), which comprises a handle and an adjuster, such as a switch or a lever, coupled to housing 382 via a tubular longitudinal member 393. For some applications, the controller of tool 380 is similar to, or comprises, controller 110 described hereinabove with reference to tool 80. The adjuster is configured to move arm 392 between the extended and retracted states. As described for tool 80 (e.g., with reference to FIG. 7), mutatis mutandis, arm 392 is typically moved between the extended and retracted states by using tubular longitudinal member 393 to move housing 382 while the arm remains stationary (e.g., with respect to anchor 40 and/or tissue of the subject). Such a configuration facilitates coupling of arm 392 to eyelet 46 of the anchor with a reduced likelihood of the arm inadvertently moving away from the eyelet.

FIG. 11A shows anchor 40 having been previously implanted in tissue 10 (e.g., to facilitate implantation of an implant; not shown in FIG. 11A, but a non-limiting illustrative example is described with reference to FIGS. 9A-10). Tool 380 is advanced toward anchor 40 with arm 392 in the extended position (or the arm is moved into the extended position after advancing the tool toward the anchor).

Arm 392 is rotated around axis a6, typically while housing 382 does not rotate. Hook portion 394 hooks through eyelet 46 of anchor 40, preliminarily coupling tool 380 to the anchor (FIG. 11B). In this state, tool 380 may be articulatably coupled to eyelet 46 (e.g., this state may be an articulatably-coupled state), e.g., as described hereinabove for tool 80, mutatis mutandis. It is to be noted that in this state, eyelet 46 inhibits movement of tool 380 (e.g., anchor-engaging element 391 thereof) proximally away from tissue anchor 40.

For some applications of the invention, tool 380 (e.g., the extracorporeal controller thereof) is configured to detect resistance to rotation of arm 392, and in response thereto, to provide an indication of this resistance, and/or to stop rotation of the arm. Typically, such resistance is due to successful hooking of eyelet 46, and the indication and/or stopping of rotation may indicate to the operator to continue with the subsequent steps of the procedure. Alternatively, such resistance may be due to engagement of an undesirable structure, such as tissue of the subject or part of an implant, in which case the indication and/or stopping of rotation may indicate to the operator to reverse the rotation and/or to reposition arm 392.

It is to be noted that tool 380 is shown having been advanced toward, and coupled to eyelet 46 with a longitudinal axis a6 of the tool (e.g., of housing 82) at a nonzero angle of attack with respect to longitudinal axis a1 of anchor 40. Tool 380 is configured to engage (e.g., to be coupled to) eyelet 46 at a variety of angles of attack, including deflection in a plane defined by longitudinal axis a1 of the tissue anchor, and around axis a1, e.g., as described for tool 80 with reference to FIGS. 5A-B, mutatis mutandis.

For example, tool 380 may be coupled to eyelet 46 while axis a6 is generally parallel to tissue 10, perpendicular to the tissue, or at any angle of attack therebetween. That is, tool 380 is configured to engage the coupling eyelet at at least 180 degrees of deflection of longitudinal axis a6 with respect to longitudinal axis a1 (e.g., in a plane on which axis a1 lies). Similarly, tool 380 may be coupled to eyelet 46 at at least most (e.g., all) rotational angles of attack around longitudinal axis a1, e.g., at least 300 degrees of deflection of axis a6 around axis a1. For some applications of the invention, this means that when tool 380 is advanced from a given direction (e.g., due to anatomical and/or other constraints), the tool is couplable to eyelet 46 at at least most (e.g., all) rotational angles of attack of anchor 40 around its longitudinal axis.

The above possible angles of attack of tool 380 may also be translated into three-dimensional terms. For example, the possible angles of attack of tool 380 typically, together, define a three-dimensional angular span of at least 1 steradian (e.g., at least 3 steradians, such as at least 7 steradians) around eyelet 46.

While tool 380 is articulatably coupled to anchor 40, the tool is deflectable with respect to the anchor. Typically, in this state, tool 380 is deflectable into any of the angles described hereinabove as angles of attack.

For some applications, such as when an angle between axes a1 and a6 is relatively large, tool 380 is subsequently manipulated so as to reduce the angle between axes a1 and a6, e.g., to at least in part align the tool and anchor 40 (e.g., as described for tool 80 with reference to FIG. 4C, mutatis mutandis). For example, tool 380 may be rotated, pulled slightly proximally (e.g., along axis a6) and/or moved orthogonally with respect to axis a6. Typically, tissue 10 is sufficiently soft and/or flexible that the tissue responsively deforms (e.g., temporarily), allowing anchor 40 to move into a position in which axes a1 and a6 are more closely aligned.

Subsequently, arm 392 is moved into the retracted position, typically by housing 382 being slid over the arm (e.g., while the arm remains stationary), and thereby also over at least part of (e.g., most of, or all of) eyelet 46 (FIG. 11C). Thus, by moving arm 392 into the retracted position, at least part of eyelet 46 moves into compartment 386.

Housing 382 is configured to receive eyelet 46 at a plurality of rotational positions (e.g., a continuum of rotational positions) with respect to the housing, such that portions of bar 44 of eyelet 46 become disposed in a circumferential space between protrusions 390, e.g., as described hereinabove for housing 82, mutatis mutandis.

As described hereinabove, the preliminary coupling of arm 392 to eyelet 46 is an articulatable coupling. Compartment 386 is typically dimensioned such that the eyelet fits generally snugly therewithin. Thereby movement of eyelet 46 into compartment 386 typically inhibits articulation of the eyelet with respect to the arm. The state of tool 380 and anchor 40 shown in FIG. 11C (and FIGS. 11D-E) may thereby, for some applications, be a rigidly-coupled state. Typically, the dimensions and/or shape of eyelet 46 (e.g., of bar 44 thereof), such as those described with reference to FIGS. 1A-B, facilitate entry of the eyelet into the compartment 386, such as by facilitating alignment of anchor 40 with tool 380. For example, curvature of the arch portion of eyelet 46 may facilitate alignment of axes a1 and a6 as the eyelet is moved into the compartment.

Subsequently, as shown in FIGS. 11D-E, housing 382 is rotated so as to rotate, and thereby unscrew, anchor 40 from tissue 10. Initially, rotation of housing 382 moves protrusions 390 until they engage (e.g., contact and press against) bar 44 of eyelet 46 (e.g., as described for tool 80 with reference to FIGS. 6C-D, mutatis mutandis). Further rotation of housing 382 applies a de-anchoring rotational force to eyelet 46, thereby rotating the eyelet and anchor 40 as a whole, and thereby unscrewing the anchor from tissue 10 (e.g., as described for tool 80 with reference to FIG. 6E, mutatis mutandis). It is to be noted that rotating housing 382 in the reverse direction may screw anchor 40 into tissue 10. For some applications, tool 380 may be used to re-anchor anchor 40 into tissue 10, or may even be used for the initial anchoring of the anchor.

It is to be noted that, although FIGS. 11A-E show anchor 40 anchored alone to tissue 10, anchor 40 is typically used to anchor another element, such as an implant, to the tissue. For example, and as described hereinabove with reference to FIGS. 9A-10 mutatis mutandis, tissue-coupling element 42 may pierce a portion of an implant and penetrate tissue 10, such that base 48 sandwiches the portion of the implant to the tissue. Similarly, tool 380 may be used to retrieve an anchor 40 from within a lumen of an implant, as described with reference to FIG. 10, mutatis mutandis.

Reference is made to FIGS. 12A-E, which are schematic illustrations of a tool 480 and techniques for use with a tissue anchor such as tissue anchor 40, in accordance with some applications of the invention. Similarly, to tool 80 and tool 380, tool 480 is also typically configured, and used, to retrieve anchor 40 from tissue of the subject (e.g., after the anchor has been previously implanted and/or used to facilitate implantation of an implant). Tool 480 comprises an anchor-engaging element 491 comprising at least one curved arm 492, typically coupled at a proximal end thereof to a mount 482. Typically, arm 492 is generally helical, and is shaped to define a distal hook portion 494. For some applications, portion 494 is simply the distal-most portion of the helix of arm 492. For some applications, distal hook portion 494 has a smaller helix pitch than more proximal portions of the helix of arm 492. For example, and as shown in the "optional" bubble of FIG. 12D, the pitch may be close to zero, such that distal hook portion 494 is disposed generally orthogonal to axis a7 of tool 480, e.g., defining a planar arc.

FIG. 12A shows anchor 40 having been previously implanted in tissue 10 (e.g., to facilitate implantation of an implant; not shown in FIG. 12A, but a non-limiting illustrative example is described with reference to FIGS. 9A-10). Tool 480 is advanced toward anchor 40, and anchor-engaging element 491 (e.g., arm 492) is rotated around a longitudinal axis a7 of the tool (e.g., by rotating a longitudinal member 483 that extends out of the body of the subject). Hook portion 494 hooks through eyelet 46 of anchor 40, preliminarily coupling tool 480 to the anchor (FIG. 12B). In this state, arm 492 may be articulatably coupled to eyelet 46 such (e.g., this state may be an articulatably-coupled state) such as described hereinabove for tool 80 and/or tool 380, mutatis mutandis. It is to be noted that in this state, eyelet 46 inhibits movement of tool 480 (e.g., anchor-engaging element 491 thereof) proximally away from tissue anchor 40.

It is to be noted that tool 480 is shown having been advanced toward, and coupled to eyelet 46 with longitudinal axis a7 of the tool at a nonzero angle of attack with respect to longitudinal axis a1 of anchor 40. Tool 480 is configured to engage (e.g., to be coupled to) eyelet 46 at a variety of angles of attack, including deflection in a plane defined by longitudinal axis a1 of the tissue anchor, and around axis a1, e.g., as described for tool 80 with reference to FIGS. 5A-B, mutatis mutandis.

For example, tool 480 may be coupled to eyelet 46 while axis a7 is generally parallel to tissue 10, perpendicular to the tissue, or at any angle of attack therebetween. That is, tool 480 is configured to engage the coupling eyelet at at least 180 degrees of deflection of longitudinal axis a7 with respect to longitudinal axis a1 (e.g., in a plane on which axis a1 lies). Similarly, tool 480 may be coupled to eyelet 46 at at least most (e.g., all) rotational angles of attack around longitudinal axis a1, e.g., at at least 300 degrees of deflection of axis a7 around axis a1. For some applications of the invention, this means that when tool 480 is advanced from a given direction (e.g., due to anatomical and/or other constraints), the tool is couplable to eyelet 46 at at least most (e.g., all) rotational angles of attack of anchor 40 around its longitudinal axis.

The above possible angles of attack of tool 480 may also be translated into three-dimensional terms. For example, the possible angles of attack of tool 480 typically, together, define a three-dimensional angular span of at least 1 steradian (e.g., at least 3 steradians, such as at least 7 steradians) around eyelet 46.

While tool 480 is articulatably coupled to anchor 40, the tool is deflectable with respect to the anchor. Typically, in this state, tool 480 is deflectable into any of the angles described hereinabove as angles of attack.

At some point during rotation of tool 480, anchor 40 provides resistance to further rotation of the tool. For example, hook portion 494 may abut base 48 of anchor 40, and/or crest 43 of eyelet 46 of the anchor may abut a mount 482 to which anchor-engaging element 491 is coupled. For some applications of the invention, tool 480 (e.g., the extracorporeal controller thereof) is configured to detect resistance to rotation of anchor-engaging element 491 (e.g., arm 492), and in response thereto, to provide an indication of this resistance, and/or to stop rotation of the arm (e.g., to provide the physician with an opportunity to decide whether to continue rotating the anchor-engaging element).

Once this resistance is met, further rotation of anchor-engaging element 491 (e.g., arm 492) applies a de-anchoring rotational force to eyelet 46, thereby rotating the eyelet and anchor 40 as a whole, and thereby unscrewing the anchor from tissue 10 (FIGS. 12D-E). It is to be noted that the helix defined by tool 480 has an opposite handedness to the helix defined by tissue-coupling element 42 of anchor 40. This allows continued rotation of anchor-engaging element 491 in one direction to (1) couple tool 480 to anchor 40, and (2) unscrew the anchor from tissue 10.

For some applications, such as when an angle between axes a1 and a7 is relatively large, tool 480 is manipulated so as to reduce the angle between axes a1 and a7, e.g., to at least in part align the tool and anchor 40 (e.g., as described for tool 80 with reference to FIG. 4C, mutatis mutandis). For example, tool 480 may be rotated, pulled slightly proximally (e.g., along axis a7) and/or moved orthogonally with respect to axis a7. Typically, tissue 10 is sufficiently soft and/or flexible that the tissue responsively deforms (e.g., temporarily), allowing anchor 40 to move into a position in which axes a1 and a7 are more closely aligned (FIG. 12D). Such manipulation of tool 480 may be performed before or after unscrewing of anchor 40 has begun.

As described hereinabove, for some applications, distal hook portion 494 has a smaller helix pitch than more proximal portions of the helix of arm 492. Such a configuration is hypothesized to facilitate alignment of tool 480 and anchor 40, by becoming disposed flat against base 48 of the anchor (e.g., as shown in the "optional" bubble of FIG. 12D). For such applications, portion 494 becoming disposed flat against base 48 inhibits articulation of tool 480 with respect to anchor 40.

Reference is made to FIGS. 13A-D, which are schematic illustrations of an anchor driver 500 and techniques for use with a tissue anchor such as tissue anchor 40, in accordance with some applications of the invention. Driver 500 comprises an anchor-engaging head 502 at a distal end of the driver, and a shaft 504 proximal to the anchor-engaging head. Shaft 504 is flexible, advanceable (e.g., transcatheterally) through vasculature of a subject, and typically has a length greater than 20 cm, and/or less than 2 m, such as greater than 50 cm and/or less than 1.5 m, e.g., between 90 cm and 1.2 m. For some applications, driver 500 comprises a handle 506 at a proximal end of shaft 504, the handle comprising an adjuster 508 (e.g., a switch or a lever) configured to actuate engaging head 502.

Engaging head 502 is configured to be reversibly couplable to tissue anchor 40 (e.g., to the engaging head thereof), so as to facilitate driving of the anchor into tissue of the subject, and subsequent release of the anchor and withdrawal of driver 500 from the subject. Actuation of engaging head 502 by adjuster 508 typically transitions the engaging head between (i) a closed state in which the engaging head is coupled (e.g., locked) to anchor 40, and (ii) an open state in which the engaging head is configured to release the anchor.

Engaging head 502 comprises a casing 514 that defines a slot 520 and a recess 518 and further comprises a detent 510 that is reversibly movable (e.g., deflectable) within the casing, such as being movable into and out of the recess. Typically, (1) detent 510 is biased toward being disposed within recess 518, such as by at least part of the detent (e.g., a stem portion 516) comprising an elastically-deformable material, and (2) the detent is moved out of the recess by a controller, such as a rod 512, applying a force to the detent, such as by being slid by adjuster 508 into at least part of the recess.

Slot 520 is dimensioned to facilitate coupling of driver 500 to anchor 40 by receiving at least part of eyelet 46 of the anchor. For some applications of the invention, driver 500 is provided pre-coupled to anchor 40 (e.g., a kit is provided comprising a plurality of drivers, each driver coupled to a respective anchor). For some applications, driver 500 is coupled to anchor 40 by the operating physician or an assistant thereof.

Movement of detent 510 out of recess 518 transitions engaging head 502 into a closed state thereof in which eyelet 46 is inhibited from exiting slot 520 and therefore in which anchor 40 is coupled to the engaging head. Movement of detent 510 into recess 518 transitions engaging head 502 into an open state thereof in which eyelet 46 is slidable out of slot 520 and thereby in which anchor 40 is decouplable from the engaging head.

Figures 13A, 13B, 13C, 13D:
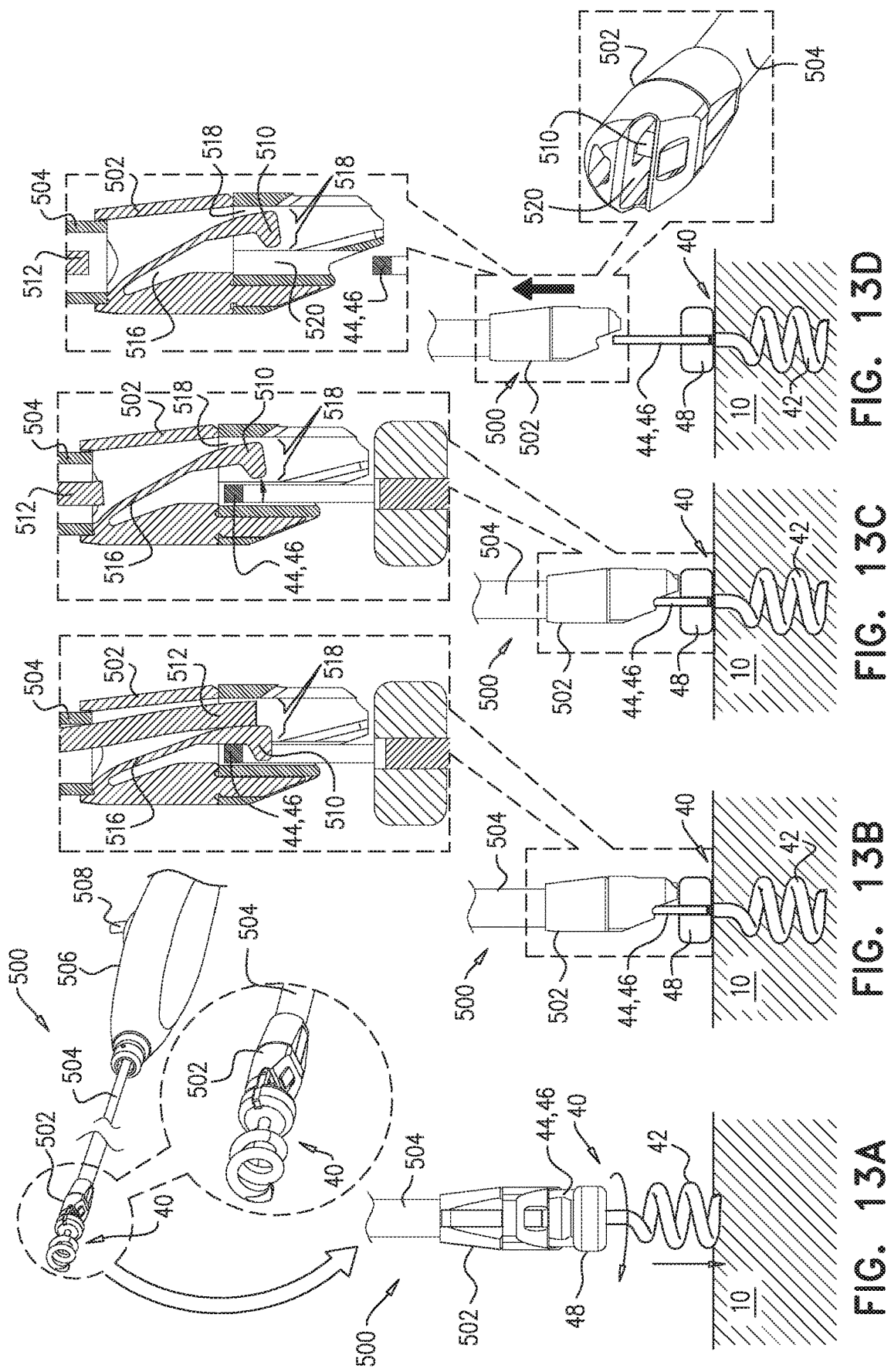
FIGS. 13A-D are schematic illustrations of an anchor driver and techniques for use with a tissue anchor, in accordance with some applications of the invention.

Driver 500 is advanced through vasculature of the subject while engaging head 502 is coupled to an anchor 40 as described hereinabove. Driver 500 is advanced toward tissue 10, and the driver (e.g., at least the engaging head thereof) is rotated so as to screw tissue-coupling element 42 of anchor 40 into the tissue (FIG. 13A). It is to be noted that, although FIGS. 13A-D show driver 500 being used to anchor anchor 40 to tissue 10 alone, as described hereinabove (e.g., with reference to Figs. with reference to FIGS. 4A-5B, and 11A-E, anchor 40 is typically used to anchor another element, such as an implant, to the tissue. For example, and as shown in FIGS. 9A-10 mutatis mutandis, tissue-coupling element 42 may pierce a portion of an implant and penetrate tissue 10, such that base 48 sandwiches the portion of the implant to the tissue. For some applications, anchor driver 500 comprises anchor driver 236, described hereinabove with reference to FIGS. 9A-C, and/or is used as described for anchor driver 236, mutatis mutandis.

Driver 500 (e.g., engaging head 502 thereof) typically rotates anchor 40 until base 48 of the anchor is firmly disposed against tissue 10 (FIG. 13B), or against a portion of an implant that is being anchored to the tissue using the anchor. For example, base 48 may sandwich sleeve 228 and/or sleeve 162 described hereinabove against tissue 10 (e.g., as shown in FIGS. 9A-10, mutatis mutandis).

Subsequently, rod 512 is moved out of recess 518 (e.g., by being withdrawn proximally), and detent 510 responsively moves into the recess, thereby transitioning driver 500 (e.g., engaging head 502) into the open state thereof (FIG. 13C). Once in the open state, driver 500 is withdrawn proximally such that eyelet 46 slides out of slot 520, leaving anchor 40 coupled to tissue 10 (FIG. 13D).

For some applications, anchor driver 500 is subsequently discarded, and any additional anchor is delivered and anchored using a respective additional anchor driver. For some applications, additional anchors are delivered and anchored using the same anchor driver.

Figure 14:
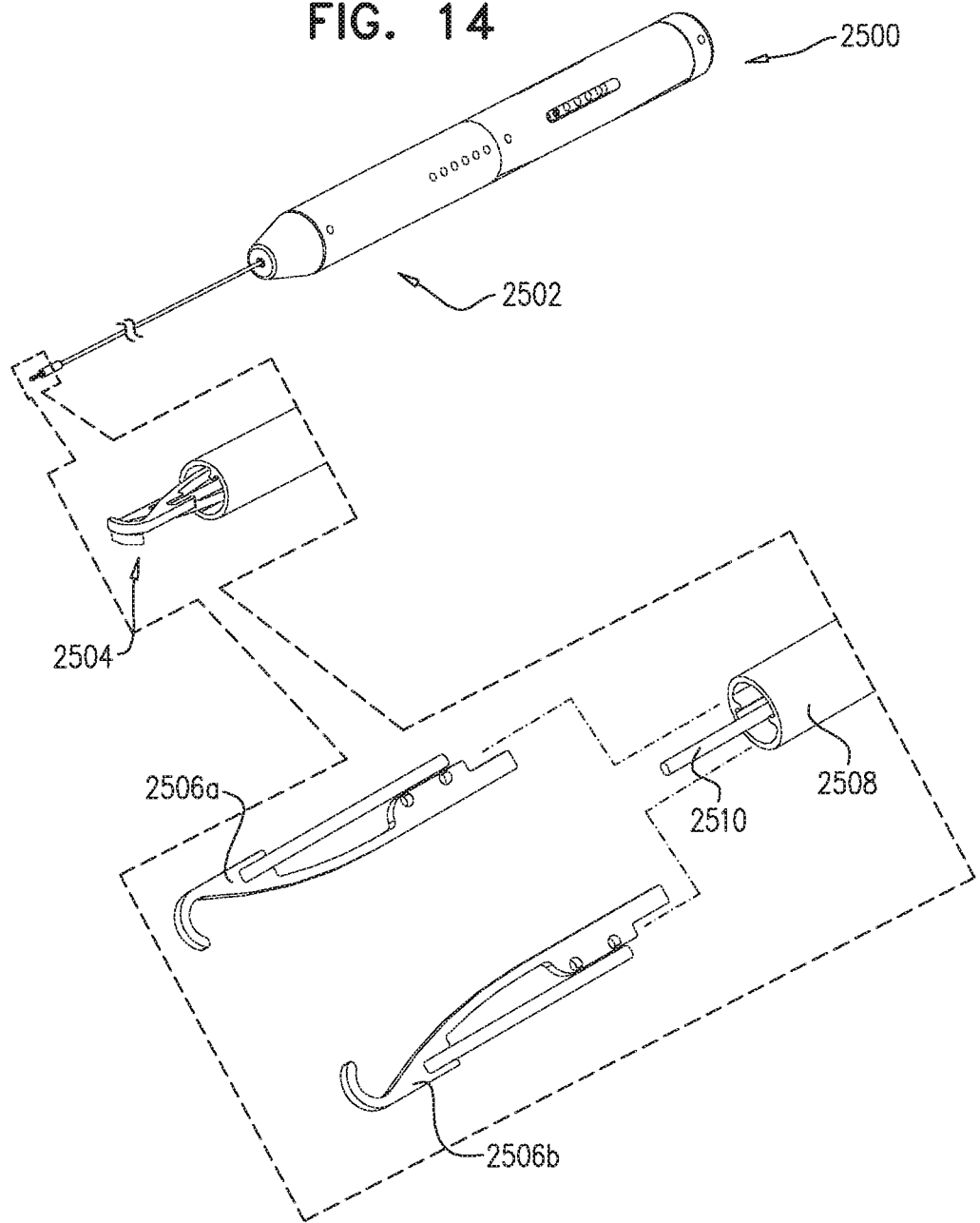

Reference is made to FIGS. 14-15C, which are schematic illustrations of a system 2500 for engaging an already-implanted anchor and facilitating extraction (e.g., retrieval) of the anchor from tissue, in accordance with some applications of the invention. For some applications of the invention, system 2500 comprises elements of, and/or has similar features to, system 100, described hereinabove. For some applications, system 2500 is used with techniques described in U.S. Provisional Application 61/717,303, which is assigned to the assignee of the present application, and is incorporated herein by reference. System 2500 comprises an anchor-manipulation tool 2502, comprising an anchor-engaging element 2504, comprising two or more arms 2506 (e.g., arm 2506a and arm 2506b), and a housing 2508. Arms 2506 are typically curved inwardly toward each other, as shown in FIGS. 35-37.

FIGS. 15A-C show tool 2502 being coupled to a tissue anchor 2532, e.g., prior to extraction of the anchor. Anchor 2532 comprises a tissue-coupling element 2536 (e.g., a helical tissue coupling element, as shown, or a screw), and a coupling head 2534 which defines, or is coupled to, a coupling eyelet 2538, which typically forms a closed loop. For some applications, tissue anchor 2532 comprises tissue anchor 40, described hereinabove. For some applications, system 2500 comprises one or more anchors 2532 (e.g., tool 2502 and anchors 2532 are specifically manufactured to be used together).

Tool 2502 is advanced toward anchor 2532 while anchor-engaging element 2504 is in an open position in which arms 2506 are held away from each other (FIG. 15A), such that eyelet 2538 of the anchor moves between the arms. Subsequently, element 2504 is closed by moving arms 2506 toward each other. Typically, in the closed configuration, arms 2506 form a closed loop, such that element 2504 and eyelet 2538 generally resemble two links in a chain. For some applications, element 2504 is closed by moving housing 2508 distally, and thereby pushing arms 2506 together (FIG. 15B). Alternatively or additionally, arms 2506 may be controlled via a control rod 2510 (shown in FIG. 14).

Housing 2508 is slid further distally, such that at least part of eyelet 2538 is disposed within the housing (FIG. 15C). This "pushing" movement is typically facilitated by a counterforce (e.g., a "pulling" force) provided by element 2504 on anchor 2532. Housing 2508 is shaped to define one or more (e.g., two) protrusions 2512, which typically protrude from an inner surface of the housing, into a lumen of the housing. When eyelet 2538 is moved into the housing, portions of the eyelet are disposed in circumferential spaces between protrusions 2512, as shown in state (i) of section A-A of FIG. 36C. Housing 2508 is subsequently rotated, such that protrusions 2512 engage eyelet 2538, as shown in state (ii) of section A-A of FIG. 36C. In this state, further rotation of tool 2502 (e.g., simultaneous rotation of element 2504 and housing 2508) rotates anchor 2532, and thereby facilitates extraction of the anchor from the cardiac tissue.

System 2500 is typically used in a similar manner to that in which system 100 is used. For some applications, system 2500 is used as described for system 100 with reference to FIG. 10, mutatis mutandis.

Reference is again made to FIGS. 14-15C. It should be noted that tool 2502 may engage eyelet 2538 of anchor 2532 at a nonzero angle, due to the chain-link nature of the coupling therebetween. It should be further noted that the use of protrusions 2512 advantageously facilitates the entry of eyelet 2538 into housing 2508 (1) initially at a nonzero angle with respect to the longitudinal axis of the housing, and (2) at a range of rotational positions with respect to the rotational position of the housing, due to the circumferential spaces between the protrusions. Purely for illustrative purposes, this configuration may be contrasted with a hypothetical system in which portions of eyelet 2538 slide into respective slits in the housing, and in which the portions of the eyelet must typically be aligned with the slits before entering the housing.

For some applications, tool 2502 may be used to redeploy tissue anchor 2532 into tissue. For yet other applications, tool 2502 may be used to initially deploy anchor 2532 into tissue. For example, sleeve 228 and/or sleeve 162 described hereinabove may be preloaded with a plurality of anchors 2532, and tool 2502 may be used to sequentially deploy each anchor into tissue in order to anchor the sleeve to the tissue. For such an application, during the deploying of the plurality of anchors, tool 2502 may also unscrew a given anchor 2532 if the physician determines that the anchor is not positioned correctly.

Typically, but not necessarily, anchor 2532 comprises a biocompatible material such as stainless steel 316 LVM. For some applications, anchor 2532 comprises nitinol. For some applications, anchor 2532 is coated with a non-conductive material.

Reference is now made to FIGS. 16-19, which are schematic illustrations of a system 1800 for engaging an already-implanted anchor and facilitating extraction (e.g., retrieval) of the anchor from tissue, in accordance with some applications of the invention. System 1800 comprises an anchor-manipulation tool 1802 comprising a tissue-anchor-engaging element 1803 comprising a distal tapered, cone-shaped anchor-engaging tip 1808, a plunger 1820, and one or more engaging structures 1810 disposed adjacently to plunger 1820. System 2500 is typically used in a similar manner to that in which system 100 is used. For some applications, system 1800 is used as described for system 100 with reference to FIG. 10, mutatis mutandis. For some applications, system 1800 is used with techniques described in U.S. Provisional Application 61/717,303 and/or in an International Patent Application entitled, "Controlled steering functionality for implant-delivery tool," to Sheps et al., filed on even date herewith, which was assigned International Application Number PCT/IL2013/050860, and which published as WO 2014/064694, both of which are assigned to the assignee of the present application and are incorporated herein by reference. Two engaging structures 1810 are shown by way of illustration and not limitation. Any suitable number of structures 1810 may be used (e.g., 1-4 structures). FIG. 16 shows an exploded view of tool 1802 in order to illustrate the relationship among the components of tool 1802. FIG. 17 shows tool 1802 in an assembled state.

Figure 18B:
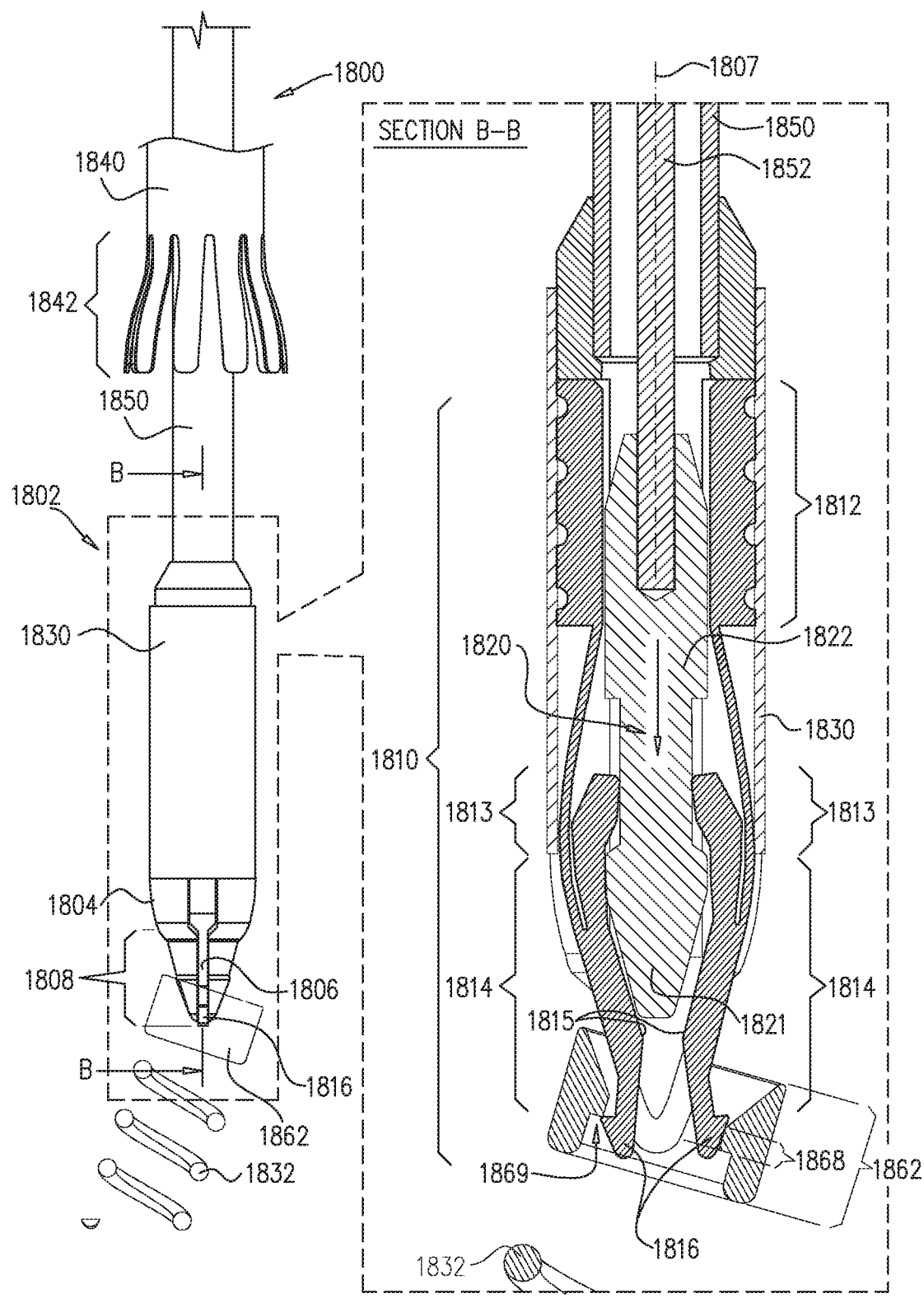
Figure 18C:
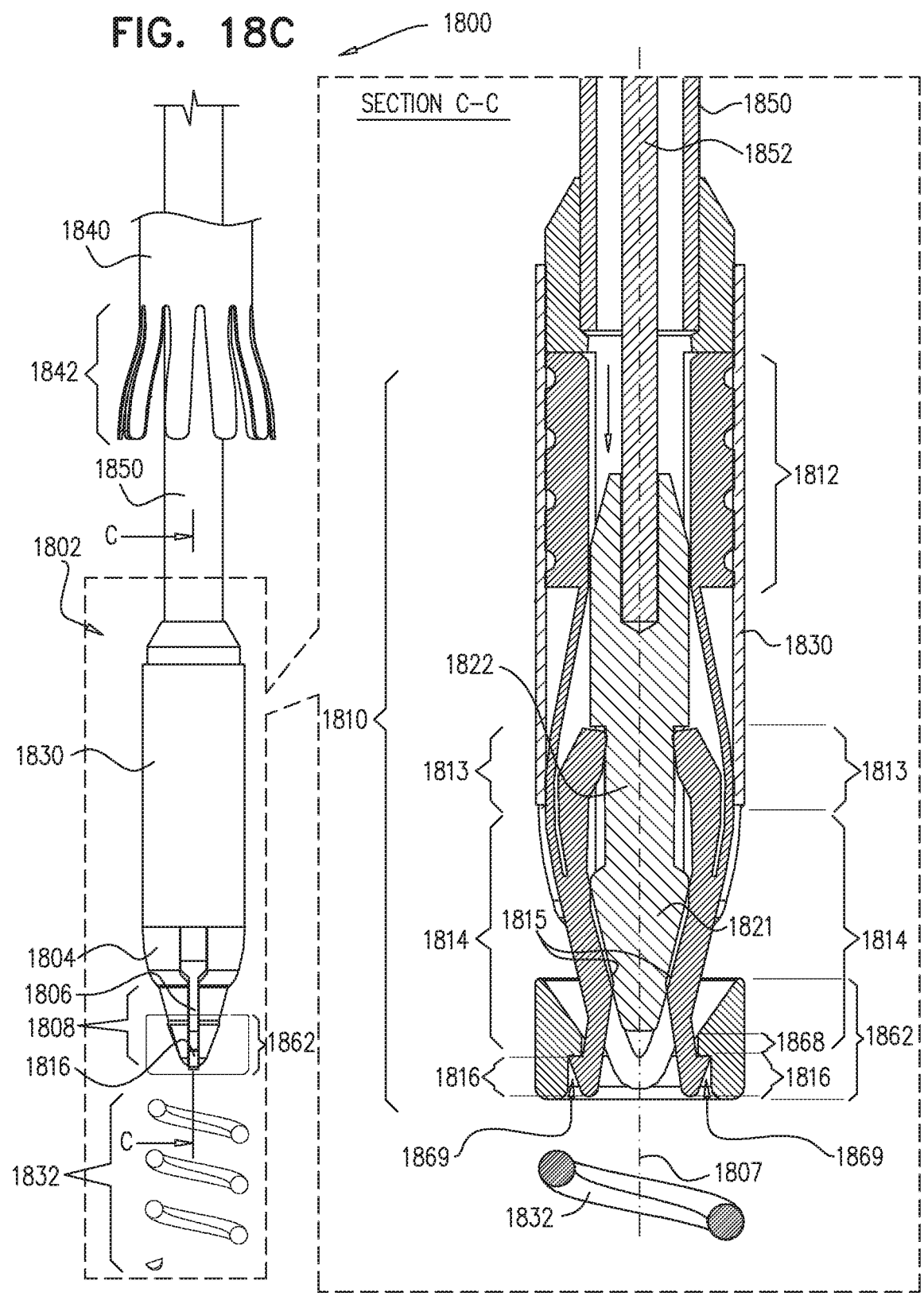

As shown in FIGS. 18A-C in the cross-sectional images, each structure 1810 comprises a curved arm 1811 having an inner surface 1815 which defines (1) a proximal portion 1813 which curves toward a longitudinal axis 1807 of tool 1802 (and toward the other arm), and (2) a central curved portion 1814 which curves away from axis 1807. Each arm 1811 is shaped so as to define and comprises a distal hook 1816 that is moveable in response to movement of arm 1811. Arm 1811 is moveable in response to proximal and distal movement of plunger 1820 along axis 1807. Thereby, plunger 1820 functions as an arm actuator (and therefore as an anchor-engaging-element actuator). As shown in FIG. 16, plunger 1820 comprises (1) a distal tapered force applicator 1821 having a proximal portion that is wider than a distal portion of force applicator 1821, and (2) a proximal longitudinal element 1822 coupled to the proximal portion of force applicator 1821. Longitudinal element 1822 is narrower than the proximal portion of force applicator 1821.

Arms 1811 are disposed within an anchor-engaging housing 1804. Housing 1804 is shaped so as to define one or more (e.g., two) slits 1806. Each slit 1806 facilitates movement of at least a portion of each arm 1811 radially away from axis 1807. Housing 1804 is shaped so as to define distal tapered anchor-engaging tip 1808 which is configured to engage an engaging head 1862 of a tissue anchor 1832 (FIGS. 18B-C) by being received within an opening of head 1862.

As shown in FIG. 18A, in a resting state of tool 1802, plunger 1802 is disposed in a proximal position in which the proximal portion of force applicator 1821 pushes against inner surface 1815 at proximal portion 1813 of arm 1811 such that a force is applied to proximal portion 1813 which keeps arm 1811 and thereby distal hooks 1816 in a closed state. In such a manner, when plunger 1802 is disposed in the proximal position, the proximal portion of applicator 1821 applies a force against proximal portion 1813 of arm 1811 in order to push proximal portions 1813 of each arm 1811 radially outward away from axis 1807, and to thereby keep hooks 1816 close together, as shown in Section A-A. For some applications, each structure 1810 has a proximal-most portion 1812 which is coupled (e.g., by being welded) to a proximal portion of an outer covering 1830. When plunger 1802 is disposed in the proximal position, the proximal portion of applicator 1821 applies a force against proximal portion 1813 of arm 1811, the proximal portion of outer covering 1830 applies a counterforce against structure 1830 to further maintain hooks 1816 in the closed state. Additionally, a distal portion of covering 1830 partially covers slits 1806 and applies additional counterforce against proximal portion 1813 of arm 1811.

Reference is now made to FIG. 18B which shows tool 1802 being manipulated into engaging head 1862 of tissue anchor 1832. As shown, anchor-engaging tip 1808 is advanced within an opening of engaging head 1862. Engaging head 1862 provides a wall shaped to define the opening, which is shaped to define a wide funnel having a wide proximal end and a narrower distal end. Engaging head 1862 is shaped so as to define an undercut 1868 and one or more recesses 1869 in a vicinity of undercut 1868. Each recess 1869 is configured to receive a respective hook 1816 of arm 1811 of tool 1802. For some applications, head 1868 provides up to 15 recesses 1869.

As shown in Section B-B, plunger 1820 is coupled at a proximal portion thereof to a plunger-manipulating element 1852. Element 1852 is slidable within a tube 1850, which is coupled at a distal end thereof to respective proximal-most portions 1812 of structures 1810. As indicated by the arrow, element 1852 is advanced distally by sliding within tube 1850, and thereby, element 1852 pushes plunger 1820 distally in a manner in which the proximal portion of force applicator 1821 is pushed beyond proximal portion 1813 of arm 1811 and force applicator 1821 is disposed adjacently to inner surface 1815 of arm 1811 at central curved portion 1814. As shown in FIGS. 16 and 18B, plunger 1820 comprises a proximal longitudinal element 1822 coupled to the proximal portion of force applicator 1821. Longitudinal element 1822 is narrower than the proximal portion of force applicator 1821 such that upon distal advancement of plunger 1820, and thereby, distal advancement of the proximal portion of force applicator 1821 beyond proximal portion 1813 of arm 1811, proximal portions 1813 of arms 1811 incline toward longitudinal element 1822 of plunger 1820. Responsively, curved central portions 1814 move radially away from axis 1807, arm 1811 moves, and, responsively to movement of arm 1811, hooks 1816 are distanced from each other by moving radially away from axis 1807.

Each hook 1816 moves within a respective slit 1806. As hooks 1816 move, the proximal portion of outer covering 1830 applies a counterforce against structure 1830 to further maintain hooks 1816 in the closed state. Additionally, a distal portion of covering 1830 partially covers slits 1806 and applies additional counterforce against proximal portion 1813 of arm 1811.

Figure 19:
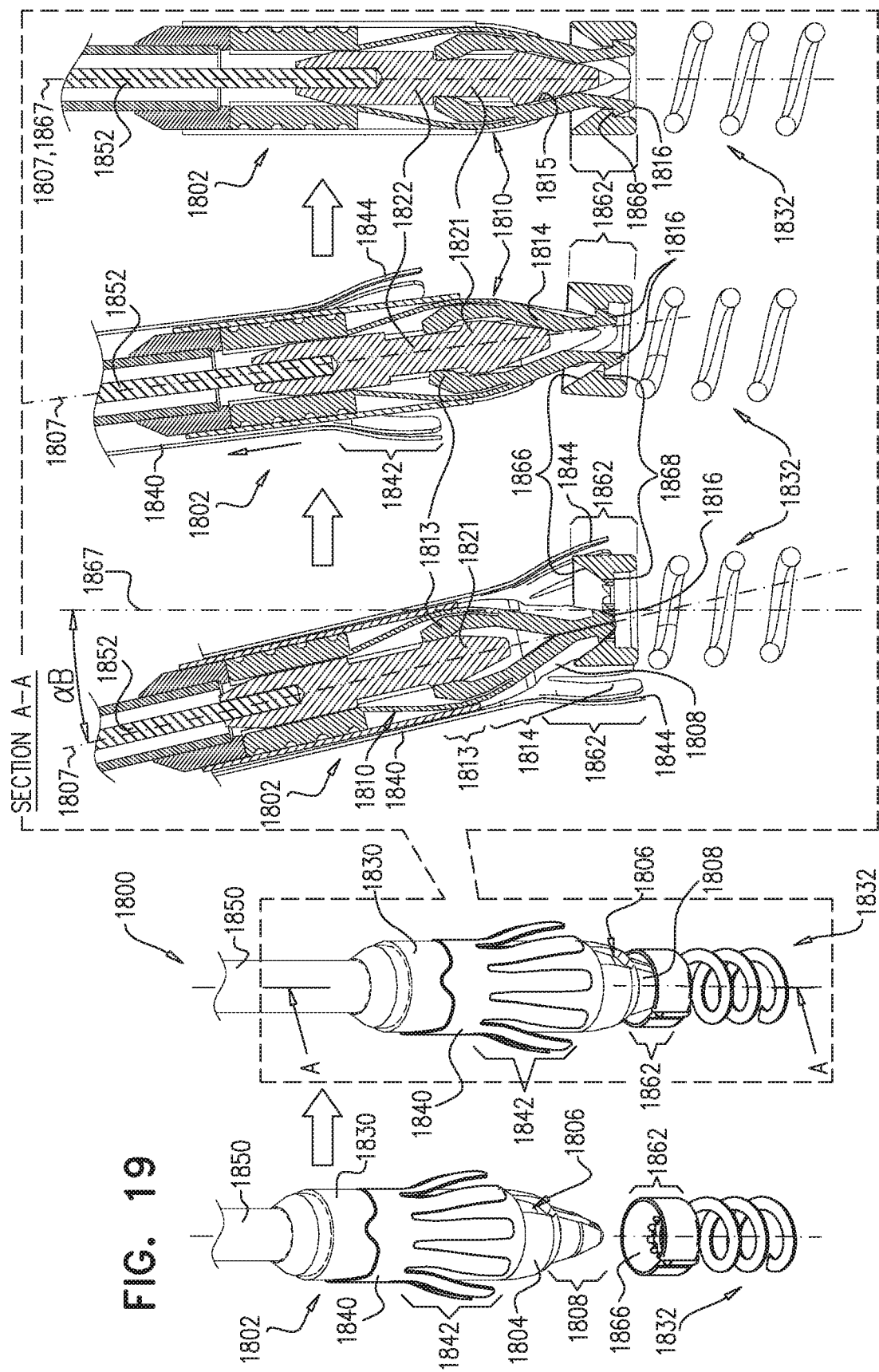

Reference is now made to FIGS. 18B and 19. As shown in Section B-B of FIG. 18B and in FIG. 19, at least one hook 1816 engages engaging head 1862 of anchor 1832, e.g., by hooking around a portion of the head, such as undercut 1868. In such a configuration, hooks 1816 have not yet been spread apart as far as possible, since force applicator 1821 of plunger 1820 has not yet been moved as far distally as possible. Thus, hooks 1816 are flexible enough to move radially inward and outward in a manner in which tool 1802 may be angled by the operating physician to optimally engage hooks 1816 with recesses 1869 in the vicinity of undercut 1868. As shown, tool 1802 is disposed at a nonzero angle with respect to engaging head 1862 of anchor 1832. Thus, the funnel shape of wall 1866 of engaging head 1862 and the cone-shape of anchor-engaging tip, together with hooks 1816 in their non-fully-deployed state (e.g., intermediate position), enable engaging of tool 1802 with engaging head 1862 of anchor 1832 at an angle alpha_B (section A-A of FIG. 19) which is between 0 and 45 degrees, e.g., between 20 and 30 degrees. Angle alpha_B is the angle between (1) longitudinal axis 1807 of tool 1802, and (2) a longitudinal axis 1867 of tissue anchor 1832.

In such a configuration of hooks 1816 with respect to undercut 1868 in FIG. 18B, tool 1802 is capable of angular movement in order to optimize engaging of hooks 1816 with undercut 1868. Once the physician is satisfied with the engaging of hooks 1816 with undercut 1868, the physician pushes down on plunger 1820 by pushing plunger-manipulating element 1852.

FIG. 18C shows additional radial movement of hooks 1816 in response to additional distal advancement of plunger 1820. Upon further distal advancement, the distal portion of force applicator 1821 applies a force against inner surface 1815 of central curved portion 1814. In response, force applicator 1821 pushes additionally on surface 1815 of curved portions 1816 of arms 1811 such that hooks 1816 are additionally pushed radially outwardly, such that they firmly engage undercut 1868, as shown in Section C-C. Plunger 1820 may then be locked into place in order to ensure hooks 1816 remain locked in place under undercut 1868 of engaging head 1862 of anchor 1832. In such a configuration, axis 1807 of tool 1802 is aligned with the longitudinal axis of anchor 1832. Once tool 1802 is positioned as shown in FIG. 18C, tool 1802 firmly engages anchor 1832 and is then rotated in order to unscrew the already-deployed tissue anchor 1832 from the tissue. For some applications, tool 1802 may be used to redeploy tissue anchor 1832 into tissue.

For yet other applications, tool 1802 may be used to initially deploy anchor 1832 into tissue. For example, sleeve 228 and/or sleeve 162, described hereinabove, may be preloaded with a plurality of anchors 1832, and tool 1802 may be used to sequentially deploy each anchor 1832 into tissue in order to anchor the sleeve to tissue. For such an application, during the deploying of the plurality of anchors, tool 1802 may also unscrew a given anchor 1832 if the physician determines that the anchor is not positioned correctly.

Typically, but not necessarily, anchor 1832 comprises a biocompatible material such as stainless steel 316 LVM. For some applications, anchor 1832 comprises nitinol. For some applications, anchor 1832 is coated with a non-conductive material.

Reference is now made to FIGS. 17 and 19. Typically (as shown), but not necessarily, tool 1802 comprises an annular (or tubular) element 1840 which is slidable around tube 1850 and comprises an annular-positioning guide 1842. Guide 1842, as shown, comprises a plurality of radially-branched tines 1844. Collectively, tines 1844 typically define a circumference having a diameter of between 4 and 5 mm (e.g., 4.5 mm) which is typically at least 1.2 times (e.g., 1.5 times) greater than a largest cross-sectional diameter of tool 1802. FIG. 19 shows the guided positioning of tool 1802 using guide 1842 of annular element 1842. Tines 1844 are configured to surround engaging head 1862 of anchor 1832 in a manner which guides tool 1802 and centralizes (e.g., aligns) anchor-engaging tip 1808 within the opening of engaging head 1862. As shown in the left-most cross-sectional image of Section A-A of FIG. 19, when tool 1802 initially engages engaging head 1862, annular element 1840 is slid distally in order to surround at least a portion of engaging head 1862. Once tool 1802 has initially engaged engaging head 1862, as shown in the middle cross-sectional image of Section A-A, annular element 1840 may be slid proximally away from engaging head 1862 of anchor 1832.

System 1800 is typically used in a similar manner to that in which system 100 and/or system 2500 is used. For some applications, system 1800 is used as described for system 100 with reference to FIG. 10, mutatis mutandis. For some applications, annular element 1840 is used to increase a working diameter for tool 1802 by opening a portion of the sleeve 228 and/or sleeve 162, e.g., a kinked portion of the sleeve. Additionally, and as described hereinabove, in response to the distal pushing of annular element 1840, annular-positioning guide 1842 helps centralize (e.g., align) anchor-engaging tip 1808 within engaging head 1862 of anchor 1832.

Figure 20A:
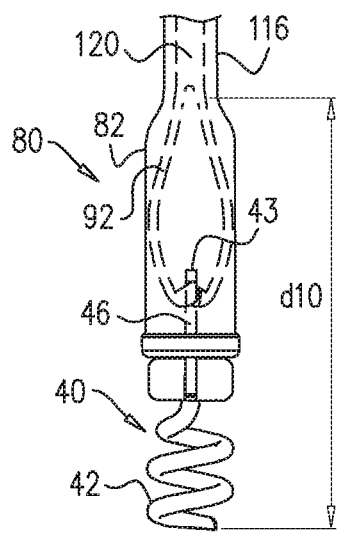
FIGS. 20A-C are schematic illustrations of a technique for use with a tool and a tissue anchor, in accordance with some applications of the invention.
Figure 20B:
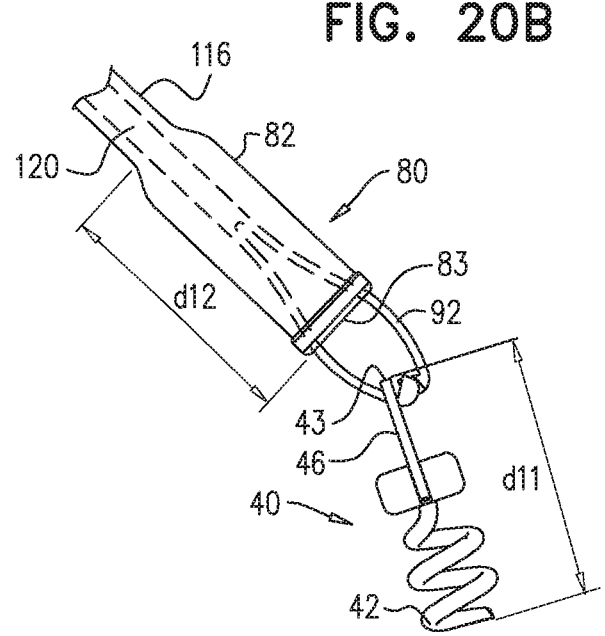
Figure 20C:
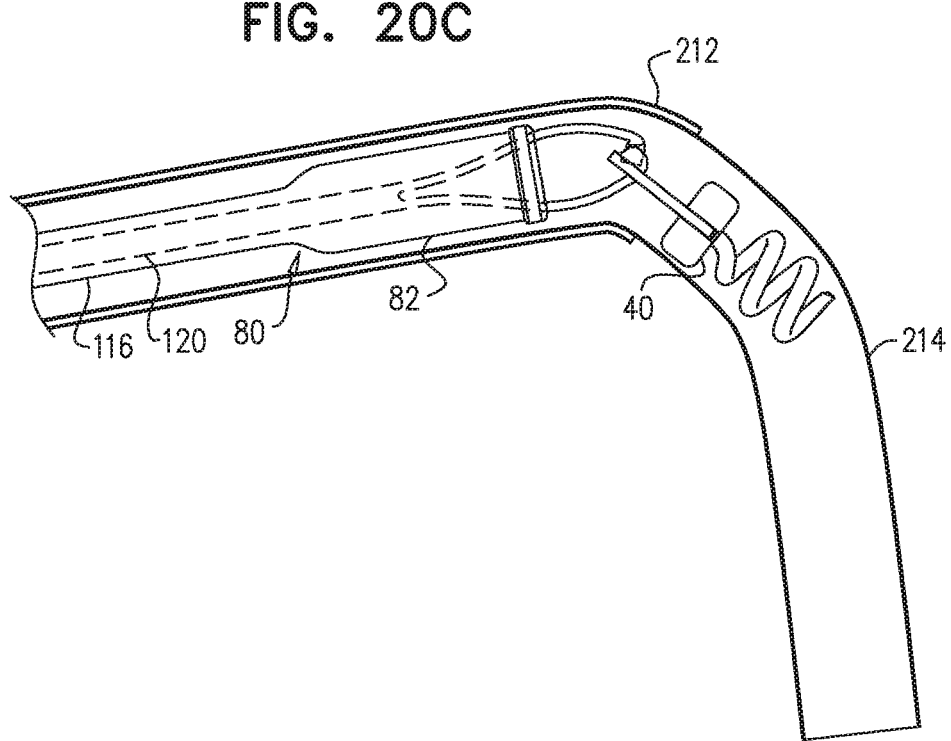

Reference is made to FIGS. 20A-C, which are schematic illustrations of a technique for use with a tool 80 and anchor 40, in accordance with some applications of the invention. As described hereinabove, tools 80 and 380 are configured to be articulatably coupled to anchor 40, to subsequently inhibit this articulation, and to subsequently de-anchor and remove the anchor. For example, FIGS. 4E and 11E show anchor 40 being withdrawn proximally by tool 80 and tool 380, respectively, while this articulation is inhibited (e.g., in a rigidly-coupled state). FIGS. 10A-C utilize tool 80 as an illustrative example, but the same techniques are applicable to tool 380, mutatis mutandis.

FIG. 20A shows eyelet 46 of anchor 40 disposed within housing 82 of tool 80, while arms 92 are in the retracted position thereof. Thereby, housing 82 inhibits articulation between tool 80 and anchor 40 (e.g., the tool and anchor are rigidly coupled to each other). In this state, a rigid length d10 is defined between (1) the distal end of tissue-engaging element 42 of anchor 40, and (2) a part of tool 80 (e.g., a part of housing 82) that is proximal to crest 43 of eyelet 46 of the anchor. Typically, rigid length d10 is defined between the distal end of tissue-engaging element 42, and a part of tool 80 that is proximal to most or all of arms 92, such as between the distal end of the tissue-engaging element and a proximal end of housing 82.

FIG. 20B shows eyelet 46 of anchor 40 disposed outside of housing 82 of tool 80, while arms 92 are in the intermediate position thereof, i.e., in the articulatably-coupled state described hereinabove. In this state, a rigid length d11 is defined between (1) the distal end of tissue-engaging element 42 of anchor 40, and (2) crest 43 of eyelet 46 of the anchor. Typically, a second rigid length d12 is defined between distal end 83 of housing 82, and a part of tool 80 that is proximal to most or all of arms 92, such as between the distal end of the housing and a proximal end of the housing. For some applications, rigid length d12 is defined between a distal end of arms 92 and the part of tool 80 that is proximal to most or all of arms 92. Typically, both rigid length d11 and rigid length d12 are smaller than rigid length d10.

It is hypothesized that, for some applications, it is advantageous to move tool 80 and anchor 40 through at least some parts of a catheter (e.g., catheter 214) while in the articulatably-coupled state. For example, and as shown in FIG. 20C, because this articulation provides shorter rigid lengths (as described with reference to FIGS. 20A-B), housing 82 and anchor 40 are able to traverse more greatly-bent portions of catheter 14 than they would in the rigidly-coupled state. Transcatheter movement of tool 80 and anchor 40 while articulatably coupled to each other may be used to facilitate both delivery and retrieval of anchors.

For some applications, tool 80 may be configured to maintain the tool and anchor 40 in the articulatably-coupled state (e.g., to prevent rigid coupling therebetween). For example, tool 80 may comprise a stopper, configured to prevent eyelet 46 from entering (e.g., fully entering) compartment 86. Alternatively, housing 82 may be configured (e.g., shaped) not to receive eyelet 46 (e.g., the housing may be configured to receive only arms 92 and not eyelet 46).

Reference is again made to FIGS. 2A-7, and reference is also made to FIGS. 21A-C, which are schematic illustrations of a tool 680 for use with tissue anchor 40, in accordance with some applications of the invention. As described hereinabove, for some applications, only one of the arms of tool 80 defines a concavity. Such a configuration is illustrated by tool 680. Typically, tool 680 and components thereof are identical to tool 80 and identically-named components thereof, except where noted. Similarly, techniques described herein for use with tool 80 may typically be used with tool 680, mutatis mutandis. Tool 680 is typically configured, and used, to retrieve anchor 40 from tissue of the subject (e.g., after the anchor has been previously implanted and/or used to facilitate implantation of an implant). For some applications, tool 680 is also configured and/or used to implant anchor 40.

Tool 680 comprises a housing 682 that has an inner surface that defines a generally cylindrical compartment 686 that has an opening 688 at a distal end 683 of the housing. Tool 80 further comprises an anchor-engaging element 691 comprising one or more (e.g., two) arms 692 (e.g., a first arm 692a and a second arm 692b) that define a space 696 therebetween. At least one arm is shaped (e.g., curved) to define a concavity 703. For example, and as shown in FIGS. 21A-C, first arm 692a may be shaped to define concavity 703. For some applications, arm 692a comprises arm 92 described hereinabove. Arm 692b is not shaped to define a concavity, and is typically generally straight. For some applications, a distal portion 694b of arm 692b deflects outward from a longitudinal axis of the tool, e.g., so as to facilitate movement of the arm around bar 44 of eyelet 46 of anchor 40.

Movement of housing 682 with respect to arms 692 moves the arms between an extended position (FIG. 21A), an intermediate position (FIG. 21B), and a retracted position (FIG. 21C), e.g., as described for tool 80 with reference to FIGS. 3A-C, mutatis mutandis. FIGS. 21A-C show stages in the transition of arms 692 from the extended position (FIG. 21A) to the retracted position (FIG. 21C). FIG. 21B illustrates that as the arms move from the extended position to the retracted position via the intermediate position, the arms form a loop before assuming the retracted position (e.g., before the completely enter compartment 86), e.g., as described for tool 80 with respect to FIGS. 3A-C, mutatis mutandis. In the intermediate position, the arms form a loop that shapes space 696 to define an aperture 697, e.g., as described for tool 80 with respect to FIGS. 3A-C, mutatis mutandis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method, comprising:
transluminally advancing a distal portion of an anchor-manipulation tool to an anchor that is intracorporeally implanted in a subject, a tissue-coupling element of the anchor being anchored within tissue of the subject, and the anchor-manipulation tool including:
at the distal portion, an anchor-engaging element and an actuator, the actuator configured to actuate the anchor-engaging element,
at an extracorporeal proximal portion of the anchor-manipulation tool, a controller, and
a flexible longitudinal member extending between the proximal portion and the distal portion;
subsequently, engaging the anchor-engaging element with an eyelet defined by a head of the anchor;
subsequently, using the controller to transition the tool into an articulatably-coupled state in which:
the eyelet at least in part inhibits movement of the anchor-engaging element away from the anchor, and
the distal portion of the anchor-manipulation tool is deflectable with respect to the anchor; and
subsequently, de-anchoring the anchor by unscrewing the tissue-coupling element from the tissue by using the anchor-manipulation tool to apply a de-anchoring rotational force to the eyelet.

2. The method according to claim 1, wherein de-anchoring the anchor comprises de-anchoring the anchor while the tool is in the articulatably-coupled state.

3. The method according to claim 1, further comprising, prior to de-anchoring the anchor, using the controller to transition the tool into a rigidly-coupled state in which the distal portion of the anchor-manipulation tool is inhibited from deflecting with respect to the tissue anchor.

4. The method according to claim 3, wherein using the controller to transition the tool into the rigidly-coupled state comprises using the controller to transition the tool from the articulatably-coupled state into the rigidly-coupled state.

5. The method according to claim 3, wherein de-anchoring the anchor comprises de-anchoring the anchor while the tool is in the rigidly-coupled state.

6. The method according to claim 3, wherein de-anchoring the anchor comprises de-anchoring the anchor while the tool is in the articulatably-coupled state.

7. The method according to claim 3, wherein:
the actuator is a housing that defines a compartment, and
using the controller to transition the tool into the rigidly-coupled state comprises using the controller to transition the tool into the rigidly-coupled state by sliding the eyelet into the compartment.

8. The method according to claim 7, wherein sliding the eyelet into the compartment comprises sliding the eyelet into the compartment such that a central longitudinal axis of the anchor becomes axially aligned with the distal portion of the tool.

9. The method according to claim 7, wherein:
the eyelet is dimensioned to fit snugly within the compartment, and
using the controller to transition the tool into the rigidly-coupled state by sliding the eyelet into the compartment comprises using the controller to transition the tool into the rigidly-coupled state by sliding the eyelet snugly into the compartment.

10. The method according to claim 7, wherein:
the housing includes one or more protrusions that protrude radially inward into the compartment, and
using the controller to transition the tool into the rigidly-coupled state by sliding the eyelet into the compartment comprises using the controller to transition the tool into the rigidly-coupled state by sliding the eyelet into the compartment such that the eyelet becomes disposed in a circumferential space between the one or more protrusions.

11. The method according to claim 10, wherein using the anchor-manipulation tool to apply the de-anchoring force to the eyelet comprises pressing the one or more protrusions against the eyelet by rotating the housing with respect to the anchor.

12. The method according to claim 7, wherein:
the eyelet has an arch portion that has a generally parabolic shape, and
sliding the eyelet into the compartment comprises sliding, into the compartment, the arch portion that has the generally parabolic shape.

13. The method according to claim 7, wherein:
the eyelet has an arch portion that has a height and a width, the height being at least 50% greater than the width, and
sliding the eyelet into the compartment comprises sliding, into the compartment, the arch portion that has the height that is at least 50% greater than the width.

14. The method according to claim 7, wherein:
the eyelet has an arch portion that is defined by a bar that has a thickness of between 0.25 mm and 0.4 mm, and
sliding the eyelet into the compartment comprises sliding, into the compartment, the arch portion that is defined by the bar that has the thickness of between 0.25 mm and 0.4 mm.

15. The method according to claim 1, wherein:
the articulatably-coupled state is an articulatably-coupled state in which the distal portion of the anchor-manipulation tool is rotatable with respect to the anchor, and
using the controller to control the actuator to transition the tool into the articulatably-coupled state comprises using the controller to control the actuator to transition the tool into the articulatably-coupled state in which the distal portion of the anchor-manipulation tool is rotatable with respect to the anchor.

16. The method according to claim 1, wherein:
the articulatably-coupled state is an articulatably-coupled state in which the distal portion of the anchor-manipulation tool is deflectable in at least 1 steradian with respect to the tissue anchor, and
using the controller to control the actuator to transition the tool into the articulatably-coupled state comprises using the controller to control the actuator to transition the tool into the articulatably-coupled state in which the distal portion of the anchor-manipulation tool is deflectable in at least 1 steradian with respect to the tissue anchor.

17. The method according to claim 16, wherein:
the articulatably-coupled state is an articulatably-coupled state in which the distal portion of the anchor-manipulation tool is deflectable in at least 3 steradians with respect to the tissue anchor, and
using the controller to control the actuator to transition the tool into the articulatably-coupled state comprises using the controller to control the actuator to transition the tool into the articulatably-coupled state in which the distal portion of the anchor-manipulation tool is deflectable in at least 3 steradians with respect to the tissue anchor.

18. The method according to claim 17, wherein:
the articulatably-coupled state is an articulatably-coupled state in which the distal portion of the anchor-manipulation tool is deflectable in at least 7 steradians with respect to the tissue anchor, and
using the controller to control the actuator to transition the tool into the articulatably-coupled state comprises using the controller to control the actuator to transition the tool into the articulatably-coupled state in which the distal portion of the anchor-manipulation tool is deflectable in at least 7 steradians with respect to the tissue anchor.

19. The method according to claim 1, wherein:
an implant includes a sleeve that defines a lumen and a proximal opening that provides access to the lumen,
the anchor that is intracorporeally implanted in the subject is anchoring the implant to the tissue, with:
the eyelet disposed within the lumen, and
the tissue-engaging element extending through the sleeve and into the tissue within which the tissue-engaging element is anchored,
transluminally advancing the distal portion of the anchor-manipulation tool to the anchor comprises transluminally advancing the distal portion of the anchor-manipulation tool through the opening and into the lumen, and
engaging the anchor-engaging element with the eyelet comprises engaging the anchor-engaging element with the eyelet within the lumen.

20. The method according to claim 19, wherein:
the anchor is a target anchor of a plurality of anchors, each of the anchors anchoring a respective longitudinal site of the sleeve to the tissue, with:
the eyelet of each of the anchors disposed within the lumen, and
the tissue-engaging element of each of the anchors extending through the sleeve and into the tissue within which the tissue-engaging element is anchored,
a proximal one of the anchors is disposed between the target anchor and the opening, and
transluminally advancing the distal portion of the anchor-manipulation tool to the anchor comprises transluminally advancing the distal portion of the anchor-manipulation tool through the opening, into the lumen, past the proximal one of the anchors, and to the target anchor.

21. The method according to claim 1, further comprising implanting the anchor in the subject by driving the tissue-coupling element into the tissue.

22. The method according to claim 21, wherein implanting the anchor in the subject comprises implanting the anchor in the subject using the anchor-manipulation tool.

23. A method, comprising:
transluminally advancing a distal portion of an anchor-manipulation tool to an anchor that is intracorporeally implanted in a subject, a tissue-coupling element of the anchor being anchored within tissue of the subject, and the anchor-manipulation tool including:
at the distal portion, an anchor-engaging element and an actuator, the actuator configured to actuate the anchor-engaging element,
at an extracorporeal proximal portion of the anchor-manipulation tool, a controller, and
a flexible longitudinal member extending between the proximal portion and the distal portion;
subsequently, engaging the anchor-engaging element with an eyelet defined by a head of the anchor;
subsequently, using the controller to transition the tool into an articulatably-coupled state in which:
the eyelet at least in part inhibits movement of the anchor-engaging element away from the anchor, and
the distal portion of the anchor-manipulation tool is deflectable with respect to the anchor;
subsequently, while the anchor remains intracorporeally implanted in the subject, using the controller to transition the anchor-manipulation tool into a rigidly-coupled state in which the distal portion of the anchor-manipulation tool is inhibited from deflecting with respect to the tissue anchor; and
subsequently, and facilitated by the anchor-manipulation tool being in the rigidly-coupled state, de-anchoring the anchor by removing the tissue-coupling element from the tissue by using the anchor-manipulation tool to apply a de-anchoring force to the eyelet.

24. A method, comprising:
transluminally advancing a distal portion of an anchor-manipulation tool to an anchor that is intracorporeally implanted in a subject, a tissue-coupling element of the anchor being anchored within tissue of the subject, and the anchor-manipulation tool including:
at the distal portion, an anchor-engaging element and an actuator, the actuator configured to actuate the anchor-engaging element,
at an extracorporeal proximal portion of the anchor-manipulation tool, a controller, and
a flexible longitudinal member extending between the proximal portion and the distal portion;
subsequently, engaging the anchor-engaging element with an eyelet defined by a head of the anchor;
subsequently, using the controller to transition the tool into an articulatably-coupled state in which:
the eyelet at least in part inhibits movement of the anchor-engaging element away from the anchor, and
the distal portion of the anchor-manipulation tool is deflectable with respect to the anchor;

subsequently, while the anchor remains intracorporeally implanted in the subject, using the controller to transition the anchor-manipulation tool into a rigidly-coupled state in which the distal portion of the anchor-manipulation tool is inhibited from deflecting with respect to the tissue anchor; and while the anchor-manipulation tool remains in the rigidly-coupled state, de-anchoring the anchor by removing the tissue-coupling element from the tissue by using the anchor-manipulation tool to apply a de-anchoring force to the eyelet.

\* \* \* \* \*